United States Patent
McCarroll et al.

(10) Patent No.: US 11,613,786 B2
(45) Date of Patent: *Mar. 28, 2023

(54) CLONAL HAEMATOPOIESIS

(71) Applicants: President and Fellows of Harvard College, Cambridge, MA (US); The Broad Institute, Inc., Cambridge, MA (US)

(72) Inventors: Steven A. McCarroll, Cambridge, MA (US); Giulio Genovese, Cambridge, MA (US)

(73) Assignees: President and Fellows of Harvard College, Cambridge, MA (US); The Broad Institute, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/858,085

(22) Filed: Apr. 24, 2020

(65) Prior Publication Data
US 2021/0123105 A1 Apr. 29, 2021

Related U.S. Application Data

(63) Continuation of application No. 15/528,807, filed as application No. PCT/US2015/062187 on Nov. 23, 2015, now Pat. No. 10,683,552.

(60) Provisional application No. 62/084,112, filed on Nov. 25, 2014.

(51) Int. Cl.
*C12Q 1/6886* (2018.01)
*C12Q 1/6883* (2018.01)

(52) U.S. Cl.
CPC ......... *C12Q 1/6886* (2013.01); *C12Q 1/6883* (2013.01); *C12Q 2600/118* (2013.01); *C12Q 2600/156* (2013.01); *G01N 2333/91017* (2013.01)

(58) Field of Classification Search
None
See application file for complete search history.

(56) References Cited

U.S. PATENT DOCUMENTS

| | | |
|---|---|---|
| 9,574,241 B2 | 2/2017 | Ferrando et al. |
| 10,683,552 B2 | 6/2020 | McCarroll et al. |
| 2003/0092019 A1 | 5/2003 | Meyer et al. |
| 2009/0093543 A1 | 4/2009 | Xue et al. |
| 2010/0197518 A1 | 8/2010 | Xu et al. |
| 2014/0127690 A1 | 5/2014 | Bejar et al. |
| 2015/0031641 A1 | 1/2015 | Levine et al. |
| 2018/0010185 A1 | 1/2018 | Ebert et al. |

FOREIGN PATENT DOCUMENTS

| | | |
|---|---|---|
| JP | 2005151854 A | 6/2005 |
| WO | WO-2006/026074 A2 | 3/2006 |

OTHER PUBLICATIONS

Hou et al. Blood. Jan. 2012. 119(2): 559-568 (Year: 2012).*
Chan et al Int J Hematol. 2013. 98)6): 648-657 (Year: 2013).*
Jan et al Sci Translational Medicine. 2012. 4: 149ra118 and Supplementary Materials, 44 pages (Year: 2012).*
Shlush et al Nature. Feb. 2014. 506(7488): 328-333 (Year: 2014).*
Al-Zahrani et al., "Fludarabine-Based Conditioning Chemotherapy for Allogeneic Hematopoietic Stem Cell Transplantation in Acquired Severe Aplastic Anemia," Biol Blood Marrow Transplant, 17:717-722 (2011).
Anonymous: "ASXL1 Gene—GeneCards," GeneCards: https://www.genecards/org/cgi-bin/carddisp.pl?gene=ASXL1&keywords=asxl1 (2020).
Bonnefond et al., "Association between large detectable clonal mosaicism and type 2 diabetes with vascular complications," Nat Genetics, 45:1040-1043 (2013).
Extended European Search Report for EP Application No. 19195023.7 dated Apr. 14, 2020.
Genovese et al., "Clonal Hematopiesis and Blood-Cancer Risk Inferred from Blood DNA sequence," New Engl J Med, 371(26):2477-2487 (2014).
Hansson., "Inflammation, Atherosclerosis, and Coronary Artery Disease," The New England Journal of Medicine, 352(16): 1685-1695 (2005).
International Preliminary Report on Patentability for International Application No. PCT/US2015/062787 dated May 30, 2017.
International Search Report and Written Opinion for International Application No. PCT/US2015/062187 dated May 15, 2016.
International Search Report and Written Opinion for International Application No. PCT/US2015/62787 dated May 4, 2016.
Jaiswal et al., Age-Related Clonal Hematopiesis Associated with Adverse Outcomes, New Engl J Med, 371(26):2488-2498 (2014).
Jaiswal et al., "Age-Related Clonal Hematopoiesis Associated with Adverse Outcomes—Online Supplementary Appendix," New England Journal of Medicine, 371(26): 2488-2498 (2014).
Kulasekararaj et al., "Somatic mutations identify a subgroup of aplastic anemia patients who progress to myelodysplastic syndrome," Blood, 124(17):2698-2704 (2014).
Leifert, Anaemia and cigarette smoking, Int J Lab Hem, 30(3):177-184 (2008).
Louw et al., "Guideline for the treatment of myelodysplastic syndromes (MDS) in South Africa," S Afr Med J, 101:900-906 (2011).
Muenlein et al., "Occurrence of the JAK2 V617F mutation in patients with peripheral aterial disease," Am J Hemtaol, 90(1):E17-E21 (2014).

(Continued)

*Primary Examiner* — Carla J Myers
(74) *Attorney, Agent, or Firm* — Foley Hoag LLP; Brendan T. Jones

(57) ABSTRACT

The present invention relates to clonal expansion of somatic cells in subjects, and acquired selective advantage of cell clones during the lifetime of a subject. In particular, the invention relates to methods for predicting the development of cancer based on the observation of specific genetic mutations in somatic cell clones, as well as to methods for treating or preventing cancer in a subject, in which clonal expansion of cells comprising specific modifications is observed.

18 Claims, 20 Drawing Sheets

Specification includes a Sequence Listing.

(56) References Cited

OTHER PUBLICATIONS

Mummidi et al., "Evolution of Human and Non-human Primate CC Chemokine Receptor 5 Gene and mRNA," Journal of Biological Chemistry, 275(25):18946-18961 (2000).
Park et al., "Reciprocal regulation of LXRa activity by ASXLI and ASXL2 in lipogenesis," Biochemical and Biophysical Research Communications, 443(2): 489-494 (2013).
Partial European Search Report for EP application No. EP19195023 dated Dec. 10, 2019.
Thol et al., "Incidence and Prognostic Influence of DNMT3A Mutations in Acute Myeloid Leukemia," Journal of Clinical Oncology, 29(21):2889-2896 (2011).
Thol et al., "Rare Occurene of DNMT3A Mutations in Myelodysplastic Syndromes," Haematologica, 96(2):1870-1873 (2011).
Tong et al., "A Meta-Analysis of the Relationship between Cigarette Smoking and Incidence of Myelodysplastic Syndromes," PLoS ONE, 8(6):e67537 (2013).
Xie et al., "Age-related mutations associated with clonal hematopoietic expansion and malignancies," Nat Med, 20:1472-1478 (2014).
Yaghootkar et al., "Genetic Evidence for a Normal-Weight 'Metabolically Obese' Phenotype Linking Insulin Resistance, Hypertension, Coronary Arterty Disease, and Type 2 Diabetes," Diabetes 63(12):4369-4377 (2014).

\* cited by examiner

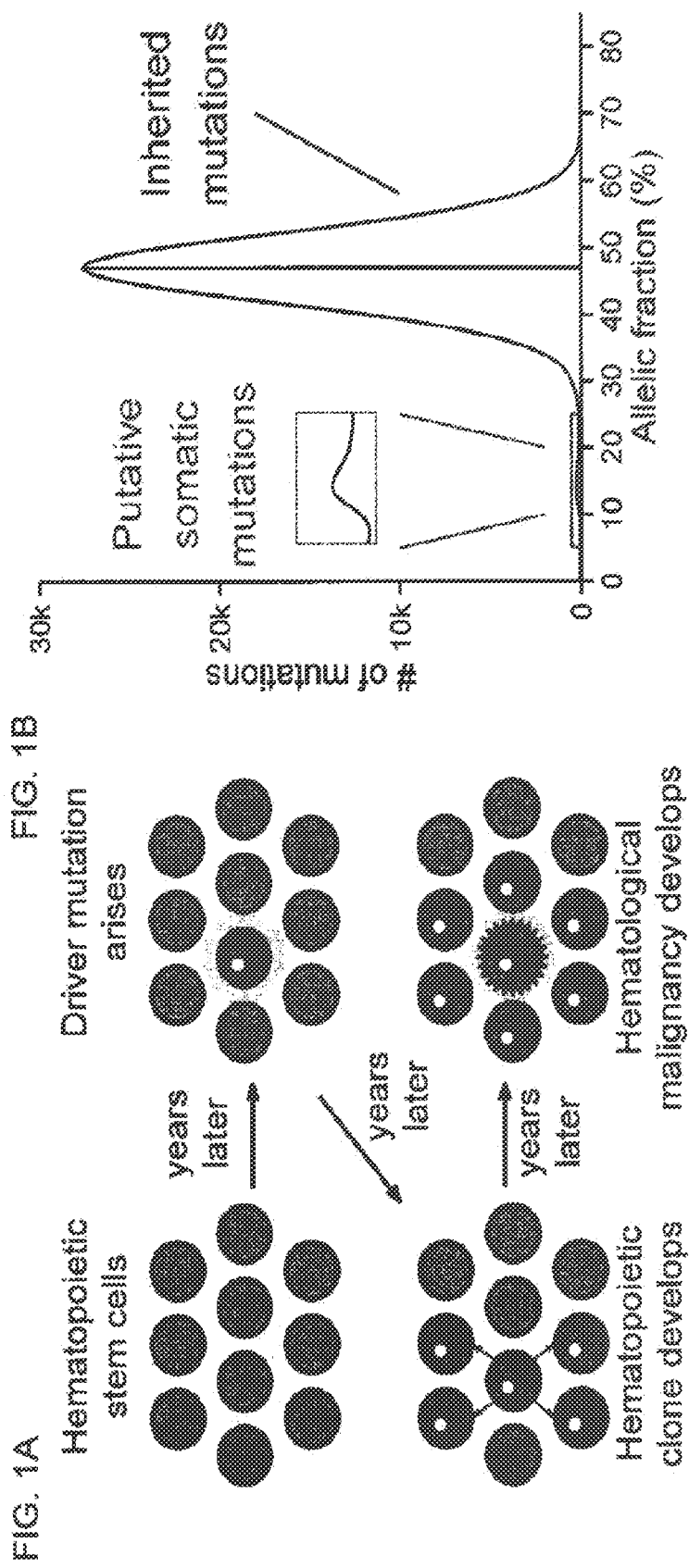

FIG. 2A
| Gene | Disruptive | Missense | Synonymous | P-value |
|---|---|---|---|---|
| All genes | 5.5% | 63.7% | 30.8% | NA |
| DNMT3A | 33 | 46 | 1 | $4.4 \times 10^{-26}$ |
| TET2 | 20 | 2 | 2 | $8.8 \times 10^{-15}$ |
| ASXL1 | 15 | 4 | 0 | $6 \times 10^{-13}$ |
| PPM1D | 10 | 0 | 0 | $7 \times 10^{-9}$ |
| Other genes | NA | NA | NA | $> 10^{-4}$ |
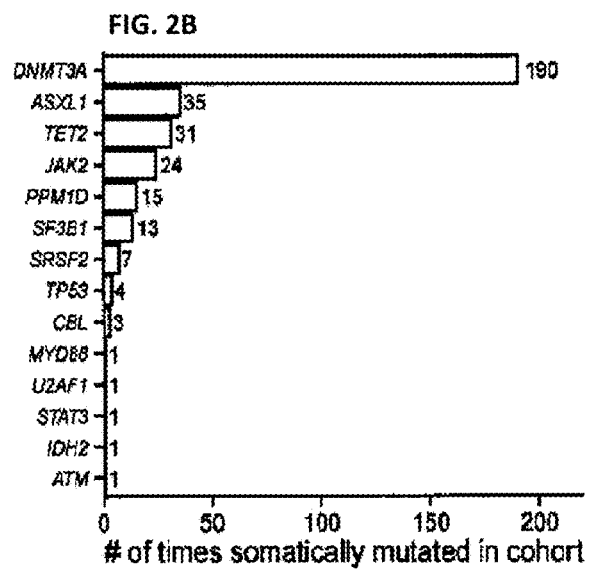
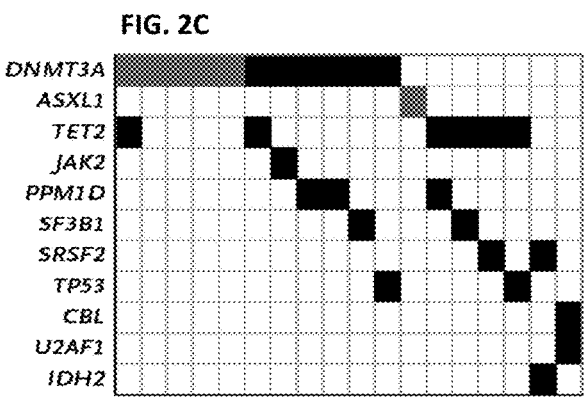
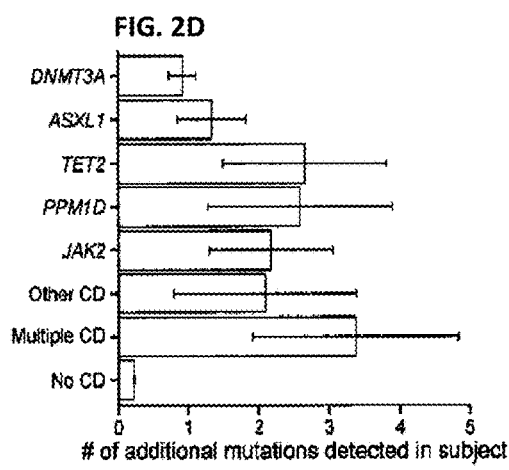
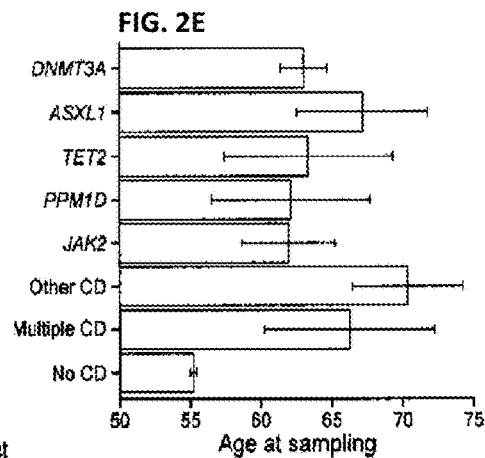

FIG. 5A
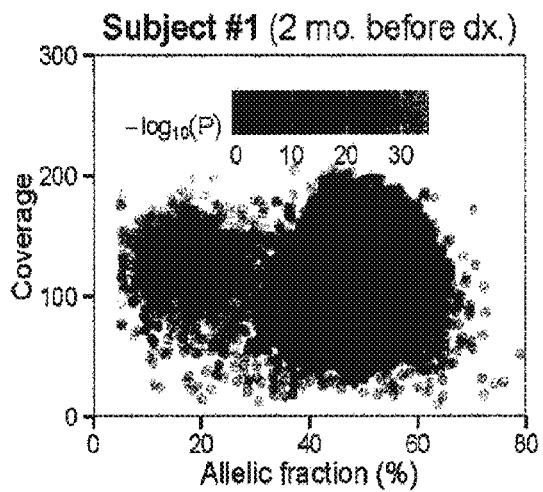
FIG. 5B
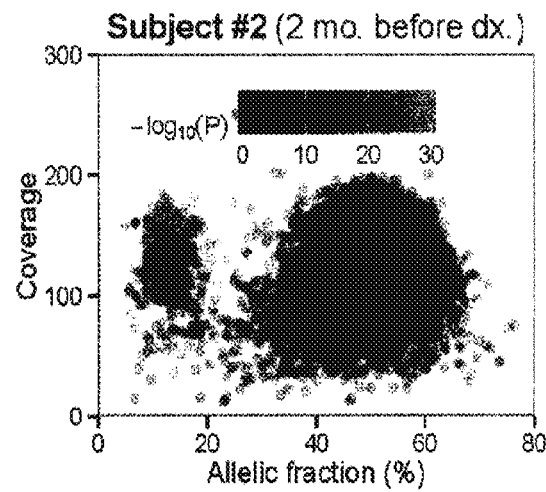
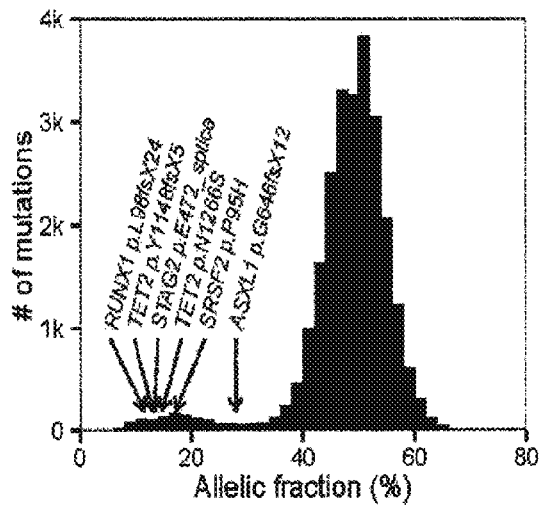
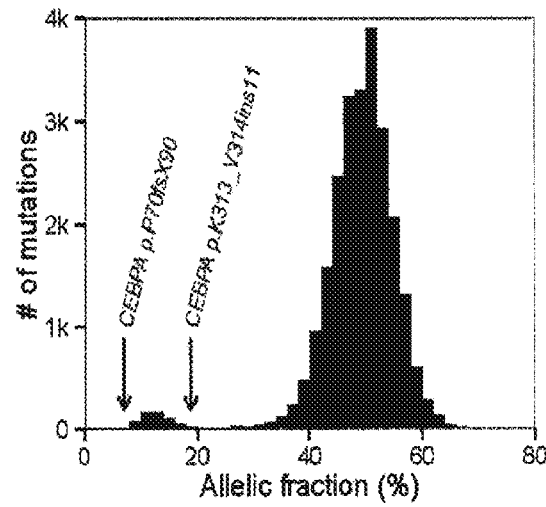
FIG. 5C
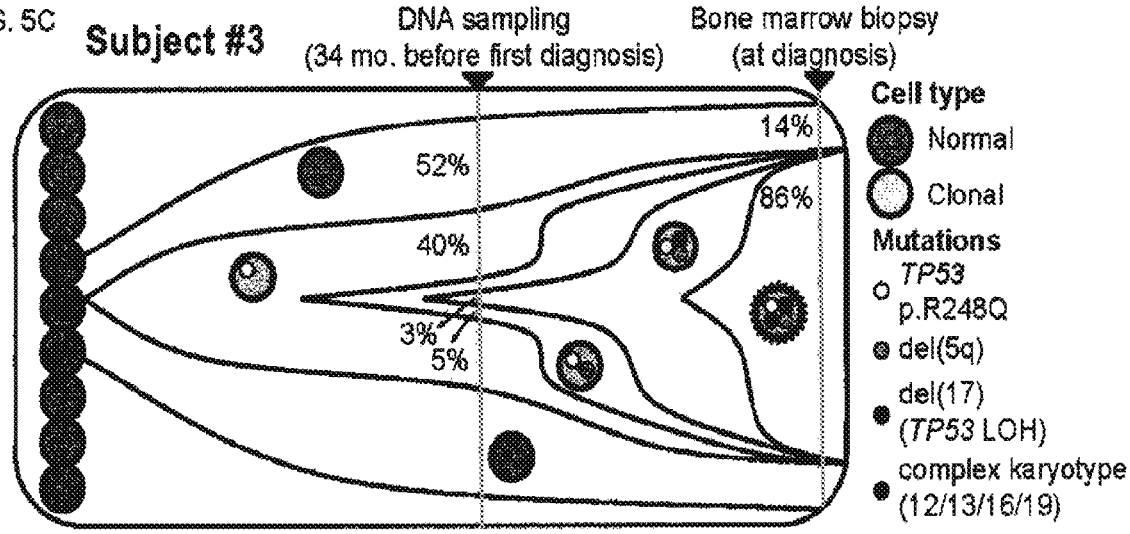

Minor allele count one

A->C (49177)
A->G (181668)
A->T (40776)
C->A (83360)
C->G (85872)
C->T (420120)

Putative somatic

A->C (175)
A->G (527)
A->T (176)
C->A (274)
C->G (315)
C->T (1644)

Inclusive somatic

A->C (2327)
A->G (5926)
A->T (1629)
C->A (4596)
C->G (5080)
C->T (20910)

Inclusive somatic in Wave1

A->C (946)
A->G (446)
A->T (120)
C->A (455)
C->G (210)
C->T (484)

Inclusive somatic in Wave2

A->C (664)
A->G (487)
A->T (2832)
C->A (407)
C->G (327)
C->T (1075)

Inclusive somatic in outlier

A->C (3)
A->G (6)
A->T (44)
C->A (999)
C->G (55)
C->T (85)

FIG. 10
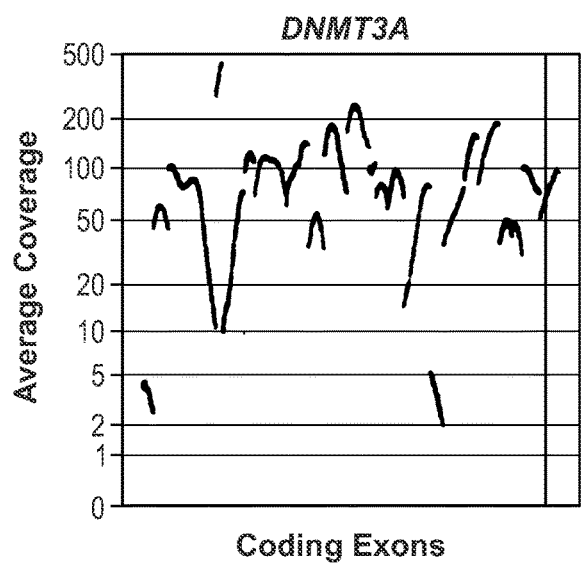
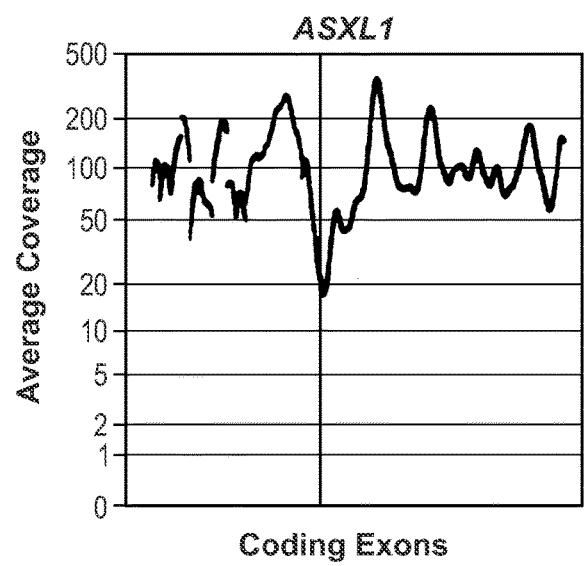
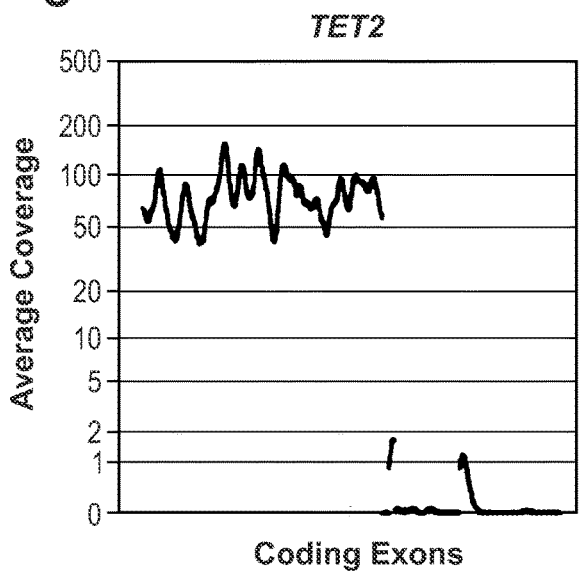
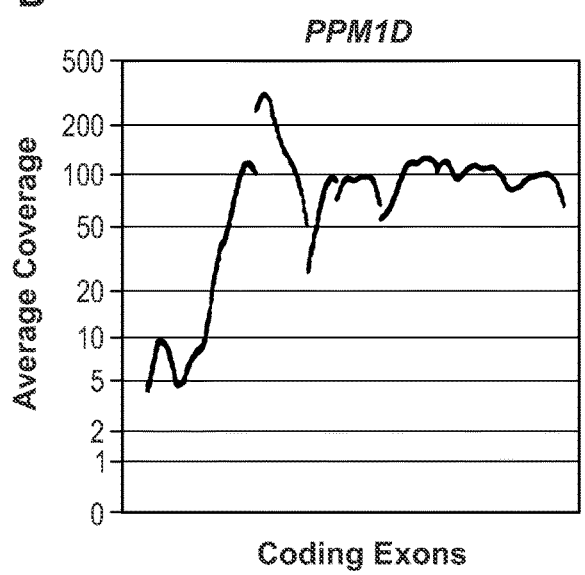

FIG. 15
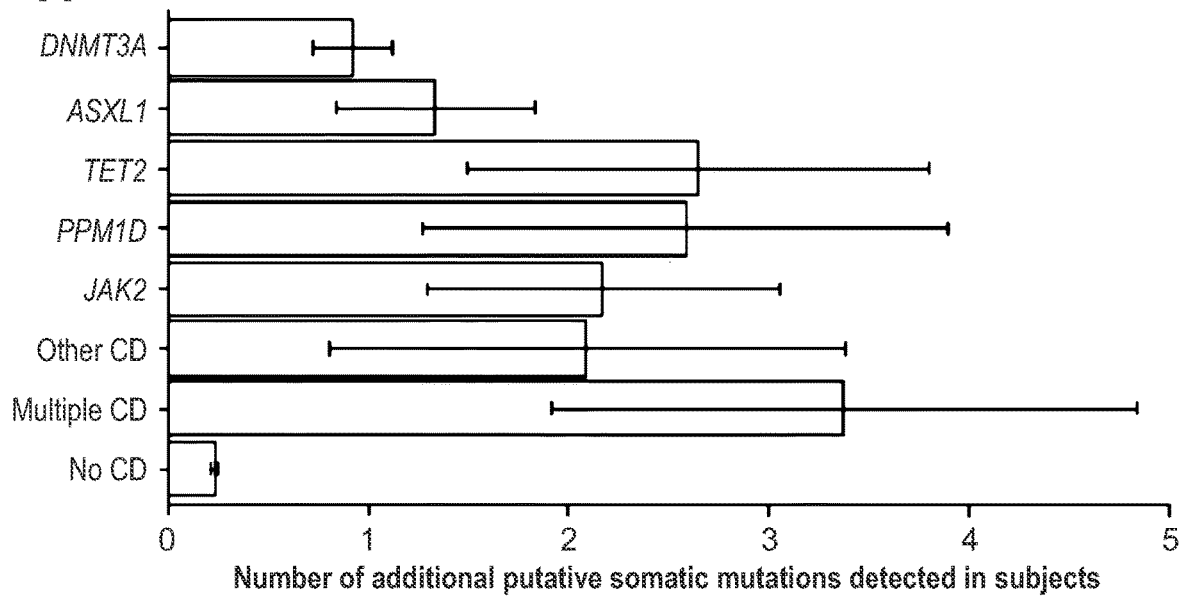
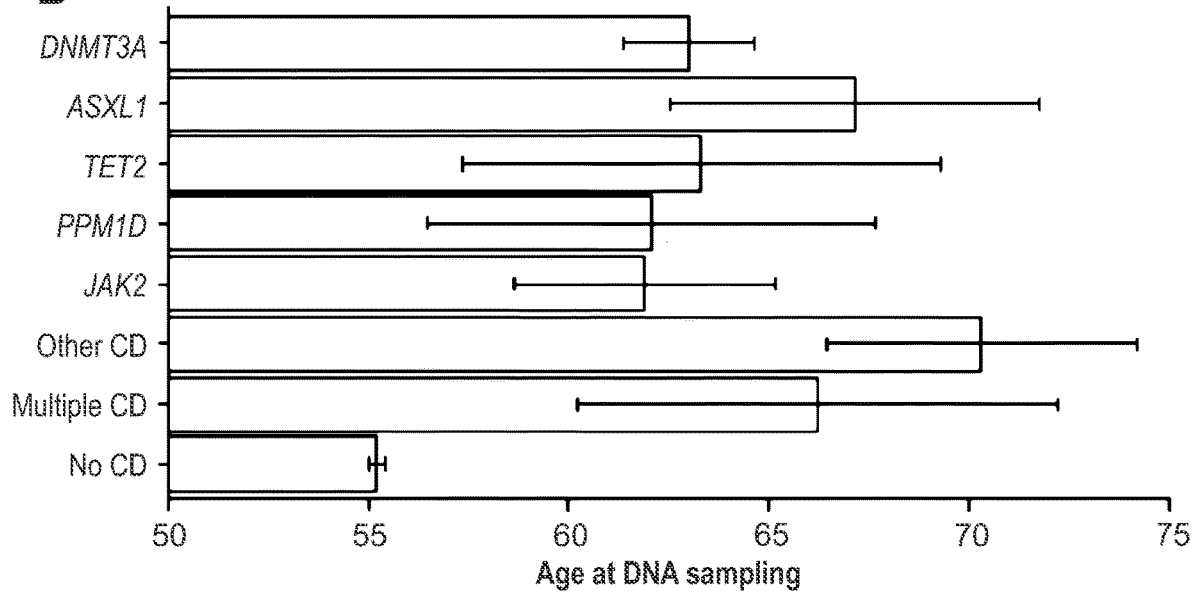

SEQUENCE LISTING

<160> NUMBER OF SEQ ID NOS: 5

<210> SEQ ID NO 1
<211> LENGTH: 15
<212> TYPE: DNA
<213> ORGANISM: Homo sapiens

<400> SEQUENCE: 1
gagaaatcgc gagat                                                    15

<210> SEQ ID NO 2
<211> LENGTH: 25
<212> TYPE: DNA
<213> ORGANISM: Homo sapiens

<400> SEQUENCE: 2
cggcggctgt ggtgtgagtc cgggg                                         25

<210> SEQ ID NO 3
<211> LENGTH: 24
<212> TYPE: DNA
<213> ORGANISM: Homo sapiens

```
<400> SEQUENCE: 3
tcaccactgc catagagagg cggc                                          24

<210> SEQ ID NO 4
<211> LENGTH: 34
<212> TYPE: DNA
<213> ORGANISM: Homo sapiens

<400> SEQUENCE: 4
accttctgct gcgtctccac gttgcgctgc ttgg                               34

<210> SEQ ID NO 5
<211> LENGTH: 34
<212> TYPE: DNA
<213> ORGANISM: Homo sapiens

<400> SEQUENCE: 5
ccaagcagcg caacgtggag acgcagcaga aggt                               34
```

CLONAL HAEMATOPOIESIS

RELATED APPLICATIONS AND INCORPORATION BY REFERENCE

This application is a continuation of U.S. U.S. patent application Ser. No. 15/528,807, filed May 23, 2017, which is a § 371 of national-stage application based on PCT/US2015/062187 filed Nov. 23, 2015, which claims the benefit of and priority to U.S. provisional patent application Ser. No. 62/084,112, filed Nov. 25, 2014.

The foregoing applications, and all documents cited therein or during their prosecution ("appln cited documents") All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT REGARDING FEDERALLY SPONSORED RESEARCH

This invention was made with government support under grant numbers HG003067, HG006855 and MH077139 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 19, 2020, is named BRB00702_SL.txt and is 1,096 bytes in size.

FIELD OF THE INVENTION

The present invention relates to clonal expansion of somatic cells in subjects, and acquired selective advantage of cell clones during the lifetime of a subject. In particular, the invention relates to methods for predicting the development of cancer based on the observation of specific genetic mutations in somatic cell clones, as well as to methods for treating or preventing cancer in a subject, in which clonal expansion of cells comprising specific modifications is observed.

BACKGROUND OF THE INVENTION

Myeloid malignancies are clonal diseases of haematopoietic stem or progenitor cells. They result from genetic and epigenetic alterations that perturb key processes such as self-renewal, proliferation and differentiation. They comprise chronic stages such as myeloproliferative neoplasms (MPN), myelodysplastic syndromes (MDS) and chronic myelomonocytic leukemia (CMML) and acute stages, i.e. acute myeloid leukemia (AML). AML can occur de novo (~80% of the cases) or follow a chronic stage (secondary AML). According to the karyotype, AMLs can be subdivided into AML with favourable, intermediate or unfavourable cytogenetic risk. MPNs comprise a variety of disorders such as chronic myeloid leukemia (CML) and non-CML MPNs such as polycythemia vera (PV), essential thrombocythemia (ET) and primary myelofibrosis (PMF).

It is widely accepted that initiation and progression of tumours are the results of clonal evolution, where acquired mutations promote the selection of mutant cell clones with progressively increased fitness.

Haematopoietic stem cells (HSCs) and Progenitor cells (HPCs) divide to produce blood cells by a continuous regeneration process. As the cells divide, they are prone to accumulating mutations that generally do not affect function. However, some mutations confer advantages in self-renewal, proliferation or both, resulting in clonal expansion of the cells comprising the mutations in question. Although these mutations are not necessarily carcinogenic, the accumulation of mutations in preferred clones can, eventually, lead to a carcinogenic phenotype. The frequency of such events appears to increase with age.

It has been observed that mutations in certain genes are associated with proliferating somatic clones, such as DNMT3A, TET2, JAK2, ASXL1, TP53, GNAS, PPM1D, BCORL1 and SF3B1 (Xie et al., Nature Medicine, published online 19 Oct. 2014; doi:10.1038/nm.3733). However, the relationship between the presence of clones comprising disruptive mutations in these genes have only been identified in 5-7% of human subjects over 70 years of age. The influence of non-disruptive mutations has not been separately analysed.

We have analysed data from whole-exome sequencing of peripheral blood cell-derived DNA from 12,380 individuals, unselected for cancer or haematological phenotypes. We identified somatic mutations based on alleles present at unusual frequencies. We used data from a Swedish national patient register to follow health outcomes for 2-7 years after DNA sampling.

Citation or identification of any document in this application is not an admission that such document is available as prior art to the present invention.

SUMMARY OF THE INVENTION

In a first aspect, there is provided a method for predicting the likelihood of progression of a subject to a cancerous state, comprising the steps of:
  (a) sequencing at least part of the subject's genome, and
  (b) identifying from said sequencing a missense mutation in gene DNMT3A in exons 7 to 23, wherein presence said mutation indicates an increased risk of developing cancer.

Clonal haematopoiesis with somatic mutations was observed in 10% of individuals over 65 years and 1% of individuals younger than 50. Detectable clonal expansions most frequently involved somatic mutations in three genes previously implicated in myeloid malignancies (DNMT3A, ASXL1, and TET2).

Although the observed mutations, including those in DNMT3A, are mostly of a disruptive nature (frameshift, nonsense, or splice-site disruption) strongly tending to disrupt protein sequence, we have found that the presence of non-disruptive missense mutations is strongly associated with clonal expansion and the subsequent development of a cancerous condition.

In embodiments, there is provided a method for predicting the likelihood of progression of a subject to a cancerous state and addressing same and hence providing a personalized medicine method, said method comprising the steps of (a) sequencing at least part of the subject's genome,
(b) identifying from said sequencing a missense mutation in gene DNMT3A, wherein presence said mutation indicates an increased risk of developing cancer, and
(c) initiating a treatment or monitoring regimen for cancer to the subject.

Clonal haematopoiesis was a strong risk factor for subsequent haematological malignancy (hazard ratio [HR] 13; 95% confidence interval [CI] 5.8 to 29). Some 42% of haematological malignancies in this cohort arose in individuals who had DNA-detectable clonality at the time of DNA sampling, 6-36 months before first malignancy diagnosis. Analysis of bone-marrow biopsies from two patients later diagnosed with acute myeloid leukemia revealed that their malignancies arose from the earlier clones. Accordingly, the present invention is based on solid evidence for the association between specific mutations in clonal haematopoietic cells and the onset of cancer.

The sample analysed in the methods of the invention is, in embodiments, a blood sample. One or more blood cells may be analysed; the invention comprises methods for analysis of pooled blood cells, as well as single-cell sequencing of single blood cells.

The missense mutation in DNMT3A is a mutation in exons 7 to 23. Such mutations are prevalent and potentially exert a dominant-negative effect on the tetrameric DNMT3A protein complex. Alternatively, the mutation is in DNMT3A isoform uc002rgb.4. In further embodiments, the method of the preceding aspects and embodiments of the invention may be combined with a method comprising identifying at least one of:
(i) one or more disruptive mutations in gene ASXL1;
(ii) one or more disruptive mutations in gene TET2;
(iii) one or more disruptive mutations in gene PPM1D;
(iv) one or more occurrences of the missense mutation JAK2 p.V617F; or
(v) one or more mutations reported at least seven times in the haematopoietic and lymphoid malignancies in the Catalogue of Somatic Mutations in Cancer (COSMIC) v69 with the exception of mutations identified in Table 2;
wherein the presence of any one of (i) to (v) indicates an increased risk of developing cancer.

Certain sequences, such as those with high GC content, repetitive elements and/or low sequence complexity are prone to sequencing errors and false positive creation due to artifacts caused by enzyme slippage and other reading errors. Hence, care must be taken to ensure that any sequence changes observed in these regions are real and not artifact. Examples of these regions include, e.g., ASXL1 p.G646fsX12 and p.G645fsX58. In certain embodiments, the disruptive mutations found at ASXL1 p.G646fsX12 and p.G645fsX58 are excluded. When observed as the sole change in a subject, we have observed these mutations to be unreliable, e.g., as a result of potential PCR slippage errors due to the presence of a G homopolymer run at these locations in ASXL1.

In embodiments, there is provided a method for predicting the likelihood of progression of a subject to a cancerous state, comprising the steps of:
(a) screening a blood sample from a subject in accordance with any one of preceding aspects and embodiments identified hereinabove that none of the conditions thereof is satisfied;
(b) determining if the sample comprises at least one of:
(i) 3 or more exomic putative somatic mutations;
(ii) 0.1 putative somatic mutation per megabase of sequenced DNA; or
(iii) 50 putative somatic mutations per genome;
wherein the presence of at least one of (i) to (iii) above indicates an increased risk of developing cancer. In embodiments, two of (i) to (iii), or all three thereof, are present.

In a further aspect, there is provided a method for predicting the likelihood of progression of a subject to a cancerous state, and addressing same and hence providing a personalized medicine method, said method comprising the steps of:
(a) screening a blood sample from a subject in accordance with any one of the preceding embodiments identified hereinabove and determining that none of the conditions of said embodiments is satisfied;
(b) determining if the sample comprises at least one of:
(i) 3 or more exomic putative somatic mutations;
(ii) 0.1 putative somatic mutation per megabase of sequenced DNA; or
(iii) 50 putative somatic mutations per genome; wherein the presence of at least one of (i) to (iii) indicates an increased risk of developing cancer, and
(c) initiating a treatment or monitoring regimen for cancer to the subject.

In a further aspect, there is provided a method for predicting the likelihood of progression of a subject to a cancerous state, comprising determining if the sample comprises at least one of:
(i) 3 or more exomic putative somatic mutations;
(ii) 0.1 putative somatic mutation per megabase of sequenced DNA; or
(iii) 50 putative somatic mutations per genome;
wherein the presence of at least one of (i) to (iii) indicates an increased risk of developing cancer.

In a still further aspect, there is provided a method for predicting the likelihood of progression of a subject to a cancerous state, and addressing same and hence providing a personalized medicine method, said method comprising determining if the sample comprises at least one of:
(i) 3 or more exomic putative somatic mutations;
(ii) 0.1 putative somatic mutation per megabase of sequenced DNA; or
(iii) 50 putative somatic mutations per genome; wherein the presence of at least one of (i) to (iii) indicates an increased risk of developing cancer, and
(iv) initiating a treatment or monitoring regimen for cancer to the subject.

In embodiments of the foregoing aspects, in section (iii), 100, 150, 200, 250 or 300 putative somatic mutations per genome are required as an indicator of clonal hematopoiesis.

In embodiments of the foregoing aspects, in section (ii), at least 0.1 mutations per megabase of sequenced DNA are required to indicate the presence of a somatic clone. On average, AML has 0.4 mutations per megabase (see Alexandrov et al., (2013) Nature 500, 415-421).

In general, a somatic mutation is a mutation that is not inherited from a parent. Hence, a somatic mutation is a genetic change that occurs in any cell after the first cell division, wherein the mutation is replicated in all cells that descend from the mutated cell. The somatic cells that descend from the original mutated cell comprise a clonal variant within the body of the subject. Where these mutation are present in cells of somatic origin and not present in the germline, they are often called a somatic cell mutation or an acquired mutation.

In embodiments, a putative somatic mutation can be detected by assessing the frequency of a mutation in a cohort of individuals. In embodiments, a somatic mutation can be defined as a mutation satisfying the following criteria:
  a) the mutation is a SNV;
  b) the mutation results in a disruptive change in the encoded polypeptide or regulation of the gene;
  c) the mutation has an allelic fraction above 10%; and
  d) the mutation includes changes in regions other than those identified as being prone to errors and artifacts, including but not limited to, e.g., low sequence complexity, high GC content, repetitive elements, and the like.

For example, in a cohort of 10,000 or more individuals, a somatic mutation can be defined as a mutation satisfying the following criteria:
  a) the mutation is a SNV;
  b) the mutation is observed once or twice in the cohort, having a minor allele frequency less than 0.01% in less than 1 in 5000 individuals;
  c) the mutation has an allelic fraction above 10%; and
  d) the mutation fails the hypothesis that the alternate mutated allelic count was distributed as a binomial process with mean 45% with a designed false positive rate of 10-5.

In embodiments, a treatment in accordance with aspects of the present invention can comprise:
  (a) treating said subject by reducing the incidence of haematopoietic clones comprising said mutation in the subject's blood; or
  (b) repeating the method as to the subject monthly, bi-monthly or quarterly and treating said subject by reducing the incidence of haematopoietic clones comprising said mutation in the subject's blood; or
  (c) including the subject as a candidate to receive a bone marrow transplant; or
  (d) administering to the subject a bone marrow transplant; or
  (e) transfusing the subject with blood in which said mutations are absent.

Accordingly, according to a further aspect there is provided a method of treating a subject at risk of developing cancer, comprising the steps of:
  (a) sequencing at least part of the genome of one or more cells in a blood sample of a subject in need of treatment;
  (b) identifying in said blood sample a mis-sense mutation in gene DNMT3A in exons 7 to 23, wherein the presence of said mutation indicates an increased risk of developing cancer; and
  (c) treating said subject by reducing the incidence of haematopoietic clones comprising said mutation in the subject's blood.

In embodiments, the method further comprises identifying in said blood sample at least one of:
  (i) one or more disruptive mutations in gene ASXL1;
  (ii) one or more disruptive mutations in gene TET2;
  (iii) one or more disruptive mutations in gene PPM1D;
  (iv) one or more occurrences of the missense mutation JAK2 p.V617F; or
  (v) one or more mutations reported at least seven times in haematopoietic and lymphoid malignancies in the Catalogue of Somatic Mutations in Cancer (COSMIC) v69 with the exception mutations identified in Table S2;
  wherein the presence of any one of (i) to (v) indicates an increased risk of developing cancer, and treating said subject by reducing the incidence of haematopoietic clones comprising said mutation in the subject's blood.

In embodiments, disruptive mutations ASXL1 p.G646fsX12 and p.G645fsX58 are excluded.

In embodiments, the incidence of haematopoietic clones comprising said mutation(s) in the subject's blood is reduced by transfusing the subject with blood in which said mutations are absent, or administering a bone marrow transplant.

For example, the subject is transfused with autologous blood.

Alternatively, or additionally, the subject is transfused with allogenic blood.

The invention provides a method for diagnosing and monitoring, and therefore treating, cancer, in which no comparison is required or is made with known cancer tissues. Thus, the method is independent of a cancer-positive control.

In the various embodiments of the invention, the mutation(s) identified can be present at an allelic fraction of less than 50%.

Generally, in the methods of the invention, a positive result indicates the presence of clonal haematopoiesis in the subject, for example the presence of an elevated proportion of blood cell clones in the subject's blood when compared to a subject in which the result is negative.

In embodiments, a prediction of a predisposition to cancer is valid for at least two years, in embodiments three years, and in further embodiments four years.

The method of the invention provides an indication of the probability of a subject developing cancer. The invention provides, for the first time, an association between observed clonal expansion of mutated cells and the onset of cancer. In embodiments, the probability of a subject testing positive in accordance with said method developing a cancerous condition is at least 0.5% per year.

In various embodiments and aspects of the invention, the subject is for example a mammal, such as a human.

The incidence of mutations in subjects has been demonstrated to increase significantly from 50 years of age. Therefore, it is proposed that analyses in accordance with the present invention are initiated in subjects of about or at least 50 years of age.

In other embodiments, or in addition, the subject is a subject undergoing therapy for cancer, such as chemotherapy.

In other embodiments, the subject can be selected form a group which is susceptible to developing cancer, but is not necessarily over 50 years of age or undergoing cancer therapy. For example, the subject is or has been exposed to a human carcinogen in sufficient amount and/or frequency for such carcinogen to be a potential cause of cancer.

The carcinogen can be a tobacco product, for example tobacco smoke.

The carcinogen can be an organic solvent. For example, the organic solvent is one used in a textile dye, a paint, or an ink.

A solvent can also be benzene, gasoline, a herbicide or a fertilizer. See Strom, S. S., Gu, Y., Gruschkus, S. K., Pierce, S. A. & Estey, E. H. Risk factors of myelodysplastic syndromes: a case-control study. Leukemia 19, 1912-1918 (2005); Strom, S. S., Oum, R., Elhor Gbito, K. Y., Garcia- Manero, G. & Yamamura, Y. De novo acute myeloid leukemia risk factors: a Texas case-control study. Cancer 118, 4589-4596 (2012).

In other examples, the carcinogen is a virus.

In still further examples, the carcinogen is a compound found in red meat, for example grilled red meat; the carcinogen is ionizing radiation; or the carcinogen is lead or a lead compound.

In the aspects and embodiments of the invention, the cancer may be any cancer, but for example the cancer is a haematological malignancy, such as a myeloproliferative neoplasm, a myelodysplastic syndrome, acute myeloid leukaemia or chronic lymphocytic leukaemia.

The invention can be applied to determining the presence of clonal haematopoiesis in a subject. Therefore, there is provided a method for determining the presence of clonal haematopoiesis in a subject, comprising the steps of:
(a) sequencing at least part of the genome of one or more cells in a blood sample of the subject;
(b) identifying in said blood sample at least one of:
  (i) one or more mis-sense mutations in gene DNMT3A in exons 7 to 23;
  (ii) one or more disruptive mutations in gene ASXL1;
  (iii) one or more disruptive mutations in gene TET2;
  (iv) one or more disruptive mutations in gene PPM1D;
  (v) one or more occurrences of the missense mutation JAK2 p.V617F; or
  (vi) one or more mutations reported at least seven times in haematopoietic and lymphoid malignancies in the Catalogue of Somatic Mutations in Cancer (COSMIC) v69 with the exception mutations identified in Table S2;
(c) if step (b) does not produce a positive result, determining if the sample comprises at least one of:
  (i) 3 or more exomic putative somatic mutations;
  (ii) 0.1 putative somatic mutation per megabase of sequenced DNA; or
  (iii) 50 putative somatic mutations per genome; wherein the presence of any one of (i) to (ix) indicates an the presence of clonal haematopoiesis.

In embodiments, the mis-sense mutation in DNMT3A is a mutation in exons 7 to 23.

In embodiments, disruptive mutations ASXL1 p.G646fsX12 and p.G645fsX58 are excluded.

A putative somatic mutation is, for example, a somatic mutation as defined above. In embodiments, a somatic mutation is a mutation satisfying the following criteria:
a) the mutation is a SNV;
b) the mutation results in a disruptive change in the encoded polypeptide or regulation of the gene;
c) the mutation has an allelic fraction above 10%; and
d) the mutation includes changes in regions other than those identified as being prone to errors and artifacts, including but not limited to, e.g., low sequence complexity, high GC content, repetitive elements, and the like.

In embodiments, in a cohort of 10,000 individuals, a somatic mutation is a mutation satisfying the following criteria:
a) the mutation is a SNV;
b) the mutation is observed once or twice in the cohort, having a minor allele frequency less than 0.01% in less than 1 in 5000 individuals;
c) the mutation has an allelic fraction above 10%; and
d) the mutation fails the hypothesis that the alternate allelic count was distributed as a binomial process with mean 45% with a designed false positive rate of 10-5.

The method of the invention can, in embodiments, further comprise initiating a treatment or monitoring regimen as to said haematopoiesis to the subject.

For example, (a) the treatment comprises treating said subject by reducing the incidence of presence of clonal haematopoiesis in the subject's blood or (b) the treatment or monitoring includes repeating the method as to the subject monthly, bi-monthly or quarterly and treating said subject by reducing the incidence of presence of clonal haematopoiesis in the subject's blood or (c) the treatment or monitoring comprises including the subject as a candidate to receive a bone marrow transplant, or (d) the treatment or monitoring includes administering to the subject a bone marrow transplant, or (e) transfusing the subject with blood in which said clonal haematopoiesis is absent.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE FIGURES

The following detailed description, given by way of example, but not intended to limit the invention solely to the specific embodiments described, may best be understood in conjunction with the accompanying drawings.

FIG. 1A-1B Clonal expansion and allelic fractions. Panel A shows a model for the expansion of a single haematopoietic stem cell or progenitor cell into a clonal population, under the influence of a somatic mutation, and the potential conversion of the clone into a malignancy through subsequent mutation. Mutations present in the founder cell would be present at an appreciable allelic fraction (though less than 50%) in blood-derived genomic DNA. Panel B shows the distribution of allelic fractions observed in sequencing data for high-confidence, ultra-rare variants ascertained in 12,380 individuals; the small left bump in this distribution represents putative somatic mutations.

FIGS. 2A-2E Candidate driver somatic mutations and subjects carrying them. Panel A shows all genes identified as carrying a statistically significant excess of disruptive (non-sense, frameshift, and splice-site) somatic mutations among 11,845 subjects with sequence data of sufficient quality for detection of somatic mutations. Panel B shows the contribution of individual genes to the total number of candidate driver somatic mutations observed. Panel C shows a co-mutation plot for subjects with multiple candidate driver somatic mutations, with subjects represented by columns, black rectangles representing genes with a single mutation, and red rectangles represent genes with two separate mutations. Panel D and panel E show respectively average number of additional putative somatic mutations and average age for individuals carrying candidate driver somatic mutations (CD), together with 95% confidence intervals, in the most commonly mutated genes DNMT3A, ASXL1, TET2, PPM1D, JAK2, and other candidate driver genes grouped together. Subjects with multiple candidate driver somatic mutations or with no such mutations are separately indicated.

FIGS. 5A-5C Haematopoietic clones and evolution in subjects subsequently diagnosed with malignancies. Panels A and B show allelic fraction for heterozygous variants in Subjects #1 and #2, each diagnosed with AML two months after DNA sampling. Whole genome sequence data were generated to an average coverage of 108 times for each base pair of the genome. Each point represents a heterozygous variant that is rare in the general population. Blue shade indicates the strength of evidence that a mutation was somatically acquired by virtue of being observed at an allelic fraction less than 50%. Mutations in black were initially ascertained in exome sequencing data. Mutations in red represent candidate driver mutations for malignancy. The histograms show the overall distribution of allelic fractions, with the candidate driver mutations shown in red. Panel C shows progression from clonal haematopoiesis to frank malignancy for Subject #3, for whom DNA was sampled 34 months before AML diagnosis and again at diagnosis.

FIG. 10A-10D Average sequencing coverage across the coding regions for genes (A) DNMT3A, (B) ASXL1, (C) TET2, and (D) PPM1D across sequencing data from the 12,380 subjects from this study. Libraries were enriched with Agilent SureSelect Human All Exon v.2 Kit. Consecutive exons are displayed with alternating colors. Vertical gray lines show the localization of recurrent mutations DNMT3A p.R882H and ASXL1 p.G646fsX12. For DNMT3A, exon 2 (amino acids 1-24) and exon 16 (amino acids 618-646) were sequenced on average less than 5 times per subject. The eight base-pair mononucleotide guanine nucleotide repeat giving rise to the recurrent ASXL1 p.G646fsX12 frameshift mutation was sequenced on average less than 20 times per subject. For TET2, only exon 3 (amino acids 1-1166) shows coverage, most likely because only the TET2 short isoform (NM_017628) was baited but not the TET2 long isoform (NM_001127208).

FIG. 15A-15B Subjects with candidate driver somatic mutations. Panel A and panel B show, respectively, average number of additional putative somatic mutations and average age for individuals carrying candidate driver somatic mutations (CD), together with 95% confidence intervals, in the most commonly mutated genes DNMT3A, ASXL1, TET2, PPM1D, JAK2, and other candidate driver genes grouped together. Subjects with multiple candidate driver somatic mutations or with no such mutations are separately indicated.

DETAILED DESCRIPTION OF THE INVENTION

Figure 3A:
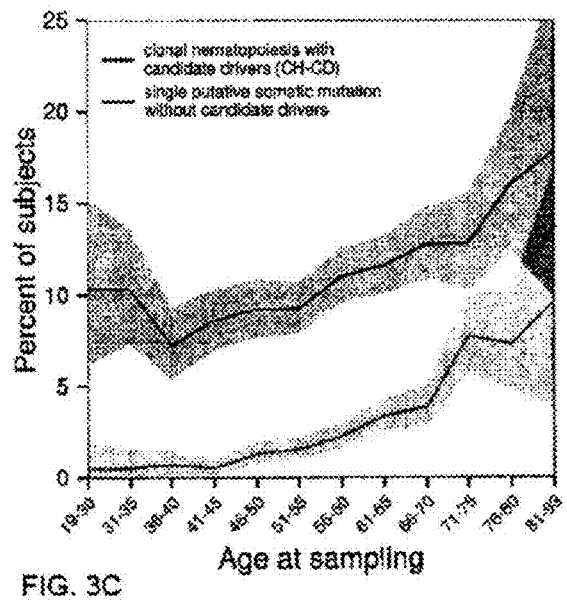
FIG. 3A-3D Prevalence of detectable putative somatic mutations as a function of age. Panel A shows estimates for subjects carrying at least one candidate driver mutation (CH-CD) and subjects carrying exactly one putative somatic mutation and no candidate drivers. Panel B shows estimates for CH-CD subjects and subjects with exactly two putative somatic mutations and no candidate drivers. Panel C shows estimates for CH-CD subjects and subjects with three or more detectable somatic mutations (our threshold for CH-UD) and no candidate drivers. Panel D shows combined estimates for subjects with clonal haematopoiesis with candidate or unknown drivers (CH-CD or CH-UD). Colored bands represent 95% confidence intervals (see Table S5 in for counts).

The development of disease often involves dynamic processes that begin years or decades before disease onset. However, the process of pathogenesis often goes undetected until after the patient develops symptoms and presents with advanced disease.

Cancer arises due to the combined effects of multiple somatic mutations, which are likely to be acquired at different times (Nowell, P. C. The clonal evolution of tumor cell populations. Science 194, 23-28 (1976)). Early mutations may be present in an individual's body many years before disease develops. In some models of cancer development, early mutations lead to clonal expansions by stem cells or other progenitor cells (Reya, T., Morrison, S. J., Clarke, M. F. & Weissman, I. L. Stem cells, cancer, and cancer stem cells. Nature 414, 105-111 (2001)). Such clonal expansions might create a favourable context for the selection of later, cooperating mutations while simultaneously increasing the likelihood that later mutations will affect cells that already contain the earlier, initiating mutations. To understand the pathogenesis of proliferative diseases, it is important to know the extent to which clonal expansions occur and precede malignancies.

Several lines of evidence suggests that haematopoietic stem cell (HSC) population dynamics may precede many haematological malignancies including myeloproliferative neoplasms (Jamieson, C. H. M. et al. The JAK2 V617F mutation occurs in hematopoietic stem cells in polycythemia vera and predisposes toward erythroid differentiation. Proc. Natl. Acad. Sci. U.S.A 103, 6224-6229 (2006)), myelodysplastic syndromes (Jaiswal, S. & Ebert, B. L. MDS Is a Stem Cell Disorder After All. Cancer Cell 25, 713-714 (2014)), acute myeloid leukaemia (AML) (Potter, N. E. & Greaves, M. Cancer: Persistence of leukaemic ancestors. Nature 506, 300-301 (2014); Vasanthakumar, A. & Godley, L. A. On the origin of leukemic species. Cell Stem Cell 14, 421-422 (2014)), and chronic lymphocytic leukemia (Damm, F. et al. Acquired initiating mutations in early hematopoietic cells of CLL patients. Cancer Discov. (2014). doi:10.1158/2159-8290.CD-14-0104). For example, in some patients, stem cells carrying a subset of the mutations present in the cancer cells are able to survive chemotherapy; subsequently, these cells acquire novel mutations, triggering relapse (Ding, L. et al. Clonal evolution in relapsed acute myeloid leukaemia revealed by whole-genome sequencing. Nature 481, 506-510 (2012); Shlush, L. I. et al. Identification of pre-leukaemic haematopoietic stem cells in acute leukaemia. Nature 506, 328-333 (2014); Corces-Zimmerman, M. R., Hong, W.-J., Weissman, I. L., Medeiros, B. C. & Majeti, R. Preleukemic mutations in human acute myeloid leukemia affect epigenetic regulators and persist in remission. Proc. Natl. Acad. Sci. U.S.A 111, 2548-2553 (2014)).

Clonal mosaicism for large chromosomal abnormalities, reflecting expansion of a specific cellular clone, appears to arise in about 2% of healthy aging individuals and is a risk factor for later haematopoietic cancers (Laurie, C. C. et al. Detectable clonal mosaicism from birth to old age and its relationship to cancer. *Nat. Genet.* 44, 642-650 (2012); Jacobs, K. B. et al. Detectable clonal mosaicism and its relationship to aging and cancer. *Nat. Genet.* 44, 651-658 (2012); Schick, U. M. et al. Confirmation of the reported association of clonal chromosomal mosaicism with an increased risk of incident hematologic cancer. *PloS One* 8, e59823 (2013)). In principle, clonal expansion among HSCs—a phenomenon termed clonal haematopoiesis—could be much more common, if only a minority of cases are accompanied by large chromosomal abnormalities (similarly to AML14).

Many studies today sequence blood-derived DNA from thousands of individuals to identify inherited risk factors for common diseases. The inventors reasoned that such data offered the opportunity to test the hypothesis that clonal haematopoiesis may be common and associate with subsequent cancer and mortality in its common form, and to identify the genes in which mutations drive clonal expansions.

The inventors therefore analysed the exome sequences from 12,380 individuals and identified 3,111 putative somatic mutations based on their presence at unusual allelic fractions, corresponding to an average of approximately one putative somatic mutation for every four subjects. For 65 of 65 mutations tested, molecular validation confirmed that the mutant allele was present at a low allelic fraction (significantly less than 50%) and thus could not have been inherited.

Figure 3B:
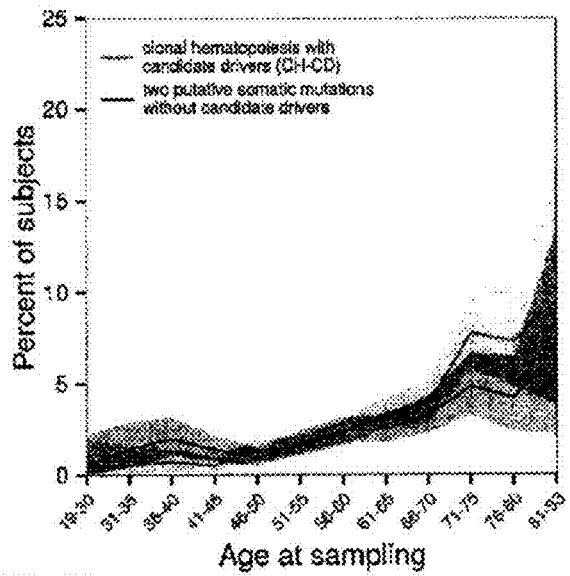
Figure 3C:
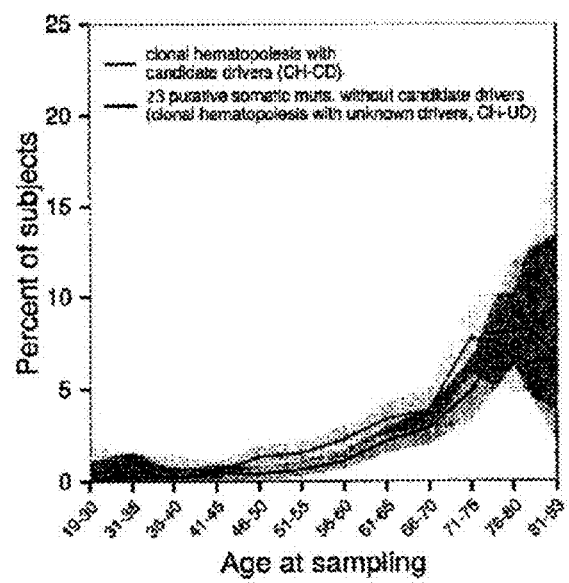
Figure 3D:
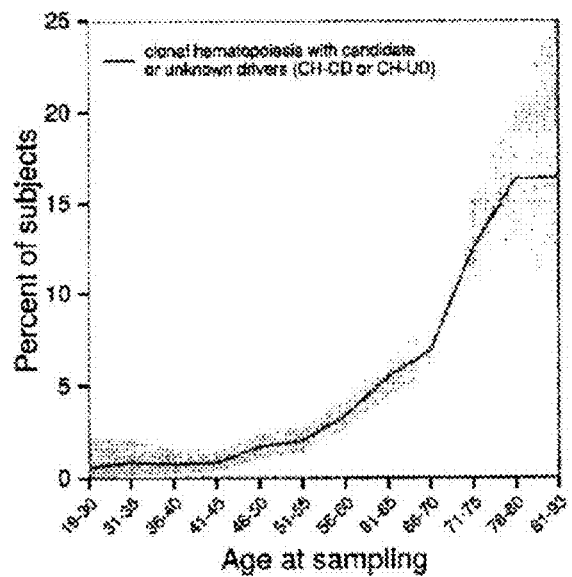
Figure 16:
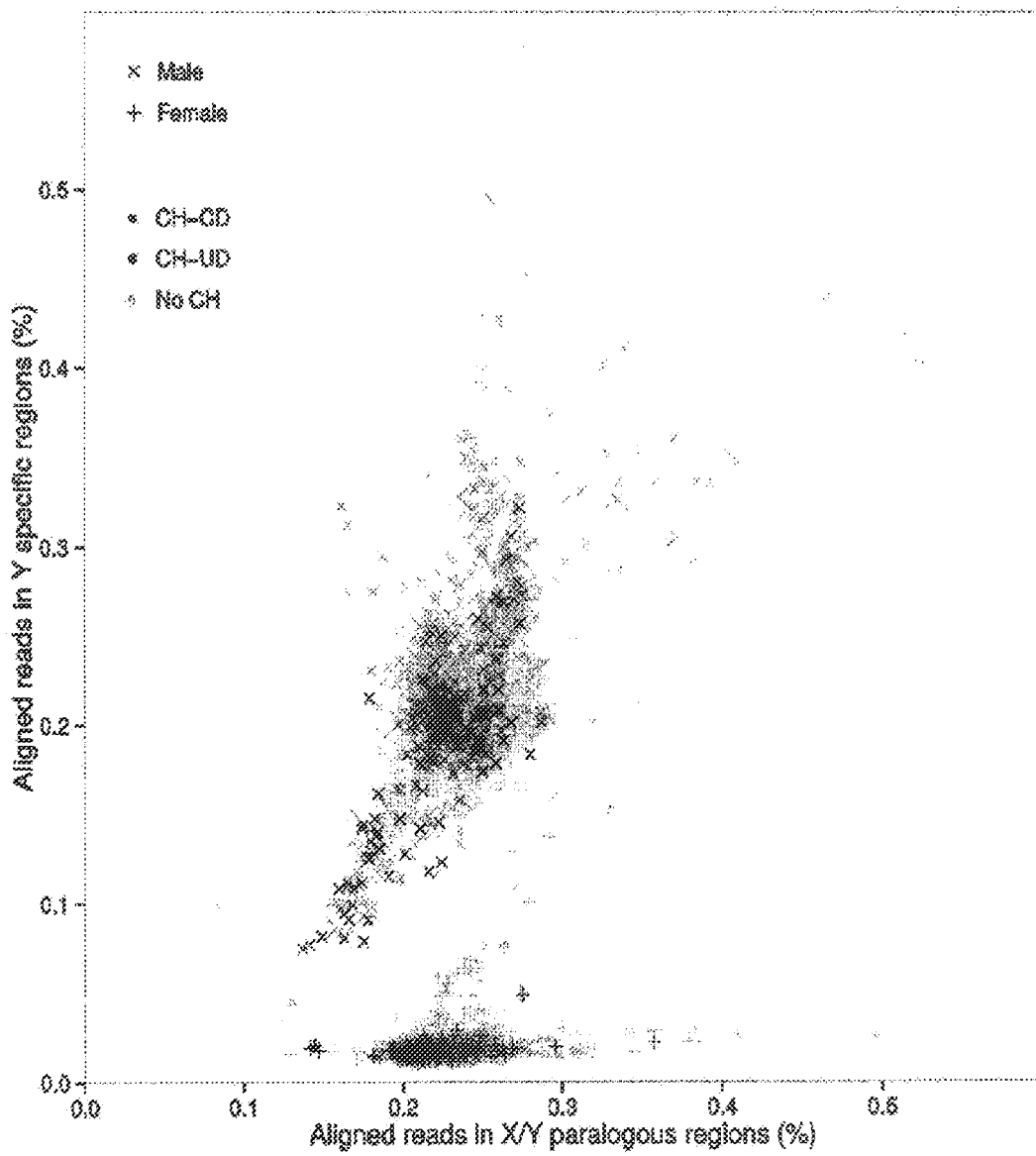
FIG. 16 Scatterplot for sequencing reads coverage over Y chromosome. For each subject we plotted the percentage of reads aligned to the paralogous regions of the X and Y chromosomes against the percentage of reads uniquely aligned to the Y chromosome. Subjects with clonal haematopoiesis with candidate drivers (CH-CD) and with unknown drivers (CH-UD) are colored, respectively, in red and black.

The inventors have found that clonal haematopoiesis with somatic mutations affects at least 10% of the elderly and increases in frequency with advancing age (FIG. 3D and FIG. 16). Most such clonal expansions appear to involve specific driver genes and mutations, which are also driver mutations in haematological cancer (FIG. 2A,B). The inventors found the presence of such clones to be a risk factor for subsequent haematological malignancies (HR 13; 95% CI 5.8 to 29, FIG. 4A) and mortality (HR 1.4; 95% CI 1.03 to 1.8, FIG. 4D).

The method of the invention involves analysis of at least part of the genome of a sample from a subject. The sample can contain one more cells, which for example can be haematopoietic stem cells (HSCs), committed myeloid progenitor cells having long term self-renewal capacity or mature lymphoid cells having long term self-renewal capacity.

In some embodiments the part of the genome that is sequenced may be limited to specific genes, the whole exome or parts of an exome. For example, the sequencing may be whole exome sequencing (WES).

In an advantageous embodiment, the subject is a human. In another advantageous embodiment, the human may be at least 50 years of age. In other embodiments, the human may exhibit one or more risk factors of being a smoker, undergoing therapy for cancer, or having been exposed to a solvent as defined herein.

Most clonal haematopoiesis appears to be driven by mutations in a specific subset of the genes recognized as drivers of blood malignancies (Shih, A. H., Abdel-Wahab, O., Patel, J. P. & Levine, R. L. The role of mutations in epigenetic regulators in myeloid malignancies. *Nat. Rev. Cancer* 12, 599-612 (2012)), such as DNMT3A, ASXL1, and TET2 (FIG. 2A). Other common mutational drivers of such malignancies—for example, activating mutations in FLT3 and NPM1 (Lawrence, M. S. et al. Discovery and saturation analysis of cancer genes across 21 tumour types. *Nature* 505, 495-501 (2014))—were not observed in these subclinical clonal expansions. Such data support a model in which mutations in DNMT3A, ASXL1, and TET2 are often early, initiating mutations that remain in subclinical states for long periods of time; FLT3 and NPM1 mutations may tend to be later, cooperating events. Such an inference would align with data emerging from studies of cancer patients and biological models. In several AML patients, the same DNMT3A mutations present in the cancer cells are also detectable in their HSCs, in which clonal expansion could have preceded AML (Shlush, L. I. et al. Identification of pre-leukaemic haematopoietic stem cells in acute leukaemia. *Nature* 506, 328-333 (2014)). Functional experiments have shown that loss of DNMT3A impairs HSC differentiation, resulting in an expansion of HSC numbers in the bone marrow (Challen, G. A. et al. Dnmt3a is essential for hematopoietic stem cell differentiation. *Nat. Genet.* 44, 23-31 (2012)), and that loss of TET2 results in increased HSC self-renewal and competitive growth advantage (Busque, L. et al. Recurrent somatic TET2 mutations in normal elderly individuals with clonal hematopoiesis. *Nat. Genet.* 44, 1179-1181 (2012)).

Many if not most haematological malignancies appear to be preceded by an extended period during which a haematopoietic clone with somatic mutations could be detected simply by sequencing the DNA in peripheral blood. Such clones were detected in 42% of the subjects who were diagnosed with malignancies 6-36 months later (FIG. 4C), and such clones were a strong risk factor for these malignancies (HR 13; 95% CI 5.8 to 29, FIG. 4A).

Appropriate perspective should be exercised when cancer-associated mutations are observed as an incidental finding in other studies or diagnostic tests: our results suggest that such findings may be common and do not justify a diagnosis of haematological malignancy. However, the present data show that defined somatic mutations are associated with particularly elevated risk; studies of large numbers of elderly individuals identify those somatic mutations with greatest likelihood of subsequent malignancy.

As used herein, an increased likelihood of progression means that the subject is more likely, in embodiments is statistically more likely, to develop cancer than a subject in which the mutations referred to herein have not been detected. For example, the subject has a higher likelihood of developing cancer when expressed as a percentage of subjects who develop cancer, as opposed to those who do not, within a defined time period. A defined time period can be from as little as six months or less, to 1, 1.5, 2, 2.5, 3, 4, 5, 6, 7, 8, 9, 10 years or more.

Statistical significance can mean that the associated p-value is 0.05 or less.

In embodiments, the increase in likelihood can be expressed as the increase in likelihood over one year. For example, the increase in likelihood can be 0.25%, 0.5%, 0.75%, 1%, 1.25%, 1.5%, 1.75%, 2% or more over one year.

Progression to a cancerous state denotes the development of a novel cancer, or malignancy, in the subject. A cancer is, in embodiments, a haematological malignancy. Examples of such cancers include myeloproliferative neoplasms (MPN), myelodysplastic syndromes (MDS) and chronic myelomonocytic leukemia (CMML), as well as acute stages, i.e. acute myeloid leukemia (AML). MPNs can comprise a variety of disorders such as chronic myeloid leukemia (CML) and non-CML MPNs such as polycythemia vera (PV), essential thrombocythemia (ET) and primary myelofibrosis (PMF).

The invention requires sequencing of at least part of the genome of a subject. Sequencing can be carried out according to any suitable technique, many of which are generally known in the art. Many proprietary sequencing systems are available commercially and can be used in the context of the present invention, such as for example from Illumina, USA. Single-cell sequencing methods are known in the art, as noted for example by Eberwine et al., Nature Methods 11, 25-27 (2014) doi:10.1038/nmeth.2769 Published online 30 Dec. 2013; and especially single-cell sequencing in microfluidic droplets (Nature 510, 363-369 (2014) doi:10.1038/nature13437).

Sequencing can be of specific genes only, specific parts of the genome, or the whole genome. Where specific genes are sequenced, the gene(s) sequences are preferably selected from the group consisting of DNMT3A, ASXL1, TET2, PPM1D and JAK2. In embodiments, specific parts of genes can be sequenced; for example in DNMT3A, exons 7 to 23 can be sequenced. In embodiments, specific mutations can be interrogated, such as the JAK2 mutation V617F. Additionally, or alternatively, specific mutations can be avoided, such as ASXL1 p.G646fsX12 and p.G645fsX58.

Where a part of a genome is sequenced, that part can be the exome. The exome is the part of the genome formed by exons, and thus an exon sequencing method sequences the expressed sequences in the genome. There are 180,000 exons in the human genome, which constitute about 1% of the genome, or approximately 30 million base pairs. Exome sequencing requires enrichment of sequencing targets for exome sequences; several techniques can be used, including PCR, molecular inversion probes, hybrid capture of targets, and solution capture of targets. Sequencing of targets can be conducted by any suitable technique.

Mutations in genes can be disruptive, in that they have an observed or predicted effect on protein function, or non-disruptive. A non-disruptive mutation is typically a missense mutation, in which a codon is altered such that it codes for a different amino acid, but the encoded protein is still expressed.

DNMT3A is DNA (cytosine-5-)-methyltransferase 3 alpha and is encoded on chromosome 2. See Human Genome Nomenclature Committee reference HGMC 2978.

ASXL1 is additional sex combs like transcriptional regulator 1 and is encoded on chromosome 20. See Human Genome Nomenclature Committee reference HGMC 18318.

TET2 is tet methylcytosine dioxygenase 2 and is encoded on chromosome 4. See Human Genome Nomenclature Committee reference HGMC 25941.

PPM1D is protein phosphatase, Mg2+/Mn2+ dependent, 1D and is encoded on chromosome 17. See Human Genome Nomenclature Committee reference HGMC 9277.

JAK2 is janus kinase 2 and is encoded on chromosome 9. See Human Genome Nomenclature Committee reference HGMC 6192.

In the context of the present invention, a "treatment" is a procedure which alleviates or reduces the negative consequences of cancer on a patient. Many cancer treatments are known in the art, and some are set forth herein. Any treatments or potential treatments can be used in the context of the present invention.

A treatment is not necessarily curative, and may reduce the effect of a cancer by a certain percentage over an untreated cancer. For example, the number of cancerous cells in a subject may be diminished by the treatment, or the overall mass of cancer tissue may be diminished.

The percentage reduction or diminution can be from 10% up to 20, 30, 40, 50, 60, 70, 80, 90, 95, 99 or 100%.

Methods of treatment may be personalised medicine procedures, in which the DNA of an individual is analysed to provide guidance on the appropriate therapy for that specific individual. The methods of the invention may provide guidance as to whether treatment is necessary, as well as revealing progress of the treatment and guiding the requirement for further treatment of the individual.

Sequencing of DNA can be performed on tissues or cells. Sequencing of specific cell types (for example, haematopoietic cells obtained by flow sorting) can identify mutations in specific cell types that provide specific predictive value. Some cell types may provide a greater predictive value than other cell types.

Sequencing can also be conducted in single cells, using appropriate single-cell sequencing strategies. Single-cell analyses can be used to identify high-risk combinations of mutations co-occurring in the same cells. Co-occurrence signifies that the mutations are occurring in the same cell clone and carry a greater risk, and therefore have a greater predictive value, that occurrence of the same mutations in different individual cells.

In certain embodiments, the mutations identified in the subject can be checked against databases of mutations which are associated with cancer. One such database is the Catalogue of Somatic Mutations in Cancer (COSMIC); Forbes, S. A. et al. COSMIC: mining complete cancer genomes in the Catalogue of Somatic Mutations in Cancer; Nucleic Acids Res. 39, D945-950 (2011). In particular, version 69 of the COSMIC database is referred to.

If analysis of the sample from the subject does not reveal the presence of any of the specific mutations identified herein as indicative of increase risk of development of cancer, or of the presence of clonal haematopoiesis, the sample can be further analysed for the presence of somatic mutations. The presence of a plurality of somatic mutations, at a level above that normally expected for a random mutation, is deemed to suggest the presence of clones. The threshold level for indicating the presence of clones is 0.1 mutations per megabase of sequenced DNA.

Typical analytical pipelines for identifying somatic mutations in cancer seek to identify mutations that are present in tumor tissue but absent from paired normal tissue from the same individual (Cibulskis, K. et al. Sensitive detection of somatic point mutations in impure and heterogeneous cancer samples. *Nat. Biotechnol.* 31, 213-219 (2013)). Because the analysis provided herein uses a single DNA sample from each subject, a novel strategy is provided for identifying somatic mutations based on allelic fractions.

Assuming that a somatic mutation will be present in only a subset of the cells contributing DNA to analysis, the mutant allele will be present in fewer than 50% of the sequence reads arising from that genomic site (FIG. 1A). The analysis relies on identification of mutations for which the measured allelic fraction (the fraction of all sequence reads interrogating the site carrying the mutant allele) deviates significantly from the frequency expected for the far-larger number of inherited variants—namely 0%, 50% or 100% (FIG. 1B). From such candidate mutations are discarded any mutations that are potentially explained by other causes, such as misalignment of sequence reads, sequence error, a strong experimental bias toward capturing the reference allele, or other potential biases.

Certain sequences, such as those with high GC content, repetitive elements and/or low sequence complexity are prone to sequencing errors and false positive creation due to artifacts caused by enzyme slippage and other reading errors. Hence, care must be taken to ensure that any sequence changes observed in these regions are real and not artifact. Due to the higher likelihood of misalignment and PCR artefacts, somatic mutations in the following regions are optionally excluded from analysis:

1) Low complexity regions and sites harboring markers failing Hardy Weinberg equilibrium tests in the 1000 Genomes Project phase 1 (Li, H. Toward better understanding of artifacts in variant calling from high-coverage samples. *Bioinforma. Oxf Engl.* (2014). doi: 10.1093/bioinformatics/btu356); (see Github files: lh3/varcmp/blob/master/scripts/LCR-hs37d5.bed.gz and lh3/varcmp/blob/master/scripts/1000g.hwe-bad.bed);
2) Sites with excess coverage within the 1000 Genomes Project phase 1 (Genovese, G., Handsaker, R. E., Li, H., Kenny, E. E. & McCarroll, S. A. Mapping the Human Reference Genome's Missing Sequence by Three-Way Admixture in Latino Genomes. *Am. J. Hum. Genet.* 93, 411-421 (2013));
3) Segmental duplications of the human genome (Bailey, J. A., Yavor, A. M., Massa, H. F., Trask, B. J. & Eichler, E. E. Segmental duplications: organization and impact within the current human genome project assembly. *Genome Res.* 11, 1005-1017 (2001); Bailey, J. A. et al. Recent segmental duplications in the human genome. Science 297, 1003-1007 (2002)) (see UCSC Genome Browser hg19 database: /goldenPath/hg19/database/genomicSuperDups.txt.gz);
4) Regions excluded from the strict mask of the 1000 Genomes Project phase 1(1000 Genomes Project Consortium et al. An integrated map of genetic variation from 1,092 human genomes. *Nature* 491, 56-65 (2012)) (see 1000 Genomes project data hosted by the European Bioinformatics Institute FTP site: vol1/ftp/phase1/analysis_results/supporting/accessible_genome_masks/20120824_strict_mas k.bed).

These filters defined regions covering ~60% of the GRCh37 human genome reference and ~70% of the coding regions and they excluded 161,158 out of the 1,812,331 variants called in the cohort described in the Examples.

Figure 6:
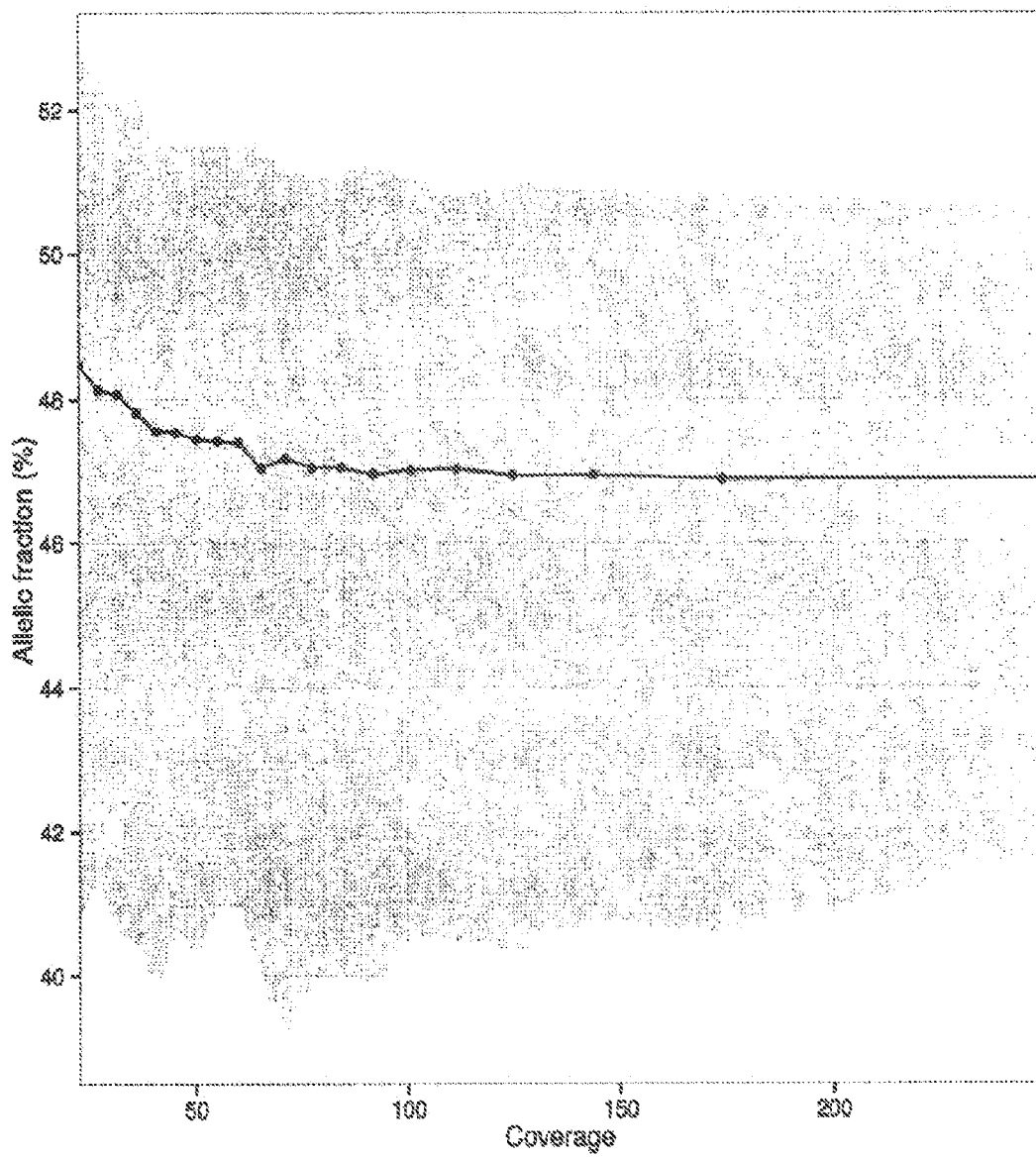
FIG. 6 Average allelic fractions and 95% confidence interval computed for each common variant with minor allele count greater than 1000 across 12,380 subjects (minor allele frequency >4%) as a function of coverage.
Figure 7A:
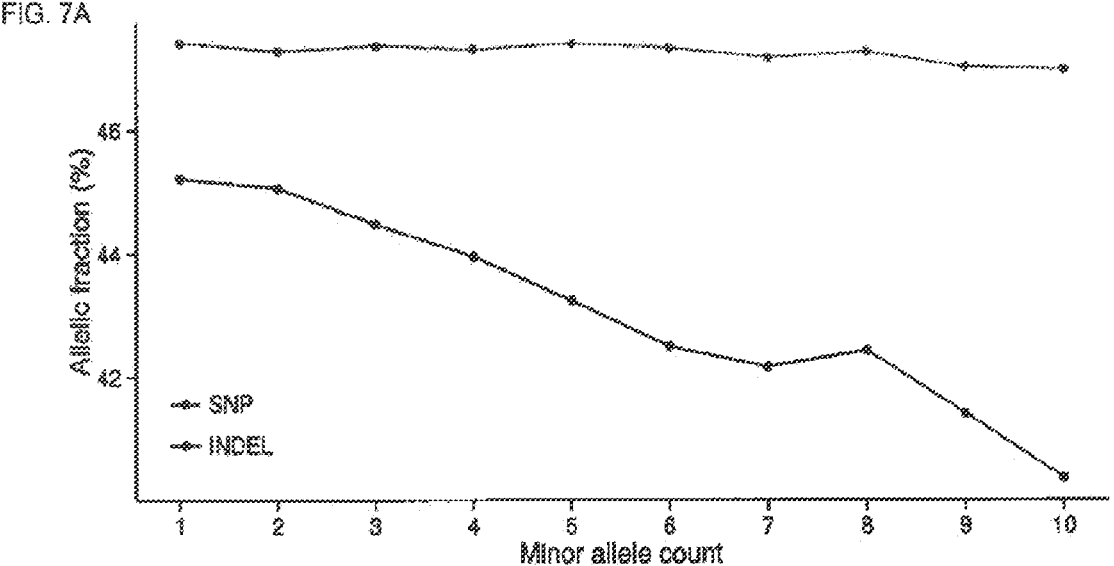
FIG. 7A-7B Average allelic fractions for variants with minor allele count less than 10 (minor allele frequency <0.04%) detected in the Sweden cohort using the Haplotype Caller walker from the Genome Analysis Toolkit without applying any filters. Panel A shows average allelic fractions for SNVs (in red) and indels (in black) and stratified by minor allele count. Panel B shows average allelic fractions for singletons (in red) and non-singletons (in black) alleles stratified by indel size, with positive size representing insertions and negative size representing deletions.
Figure 7B:
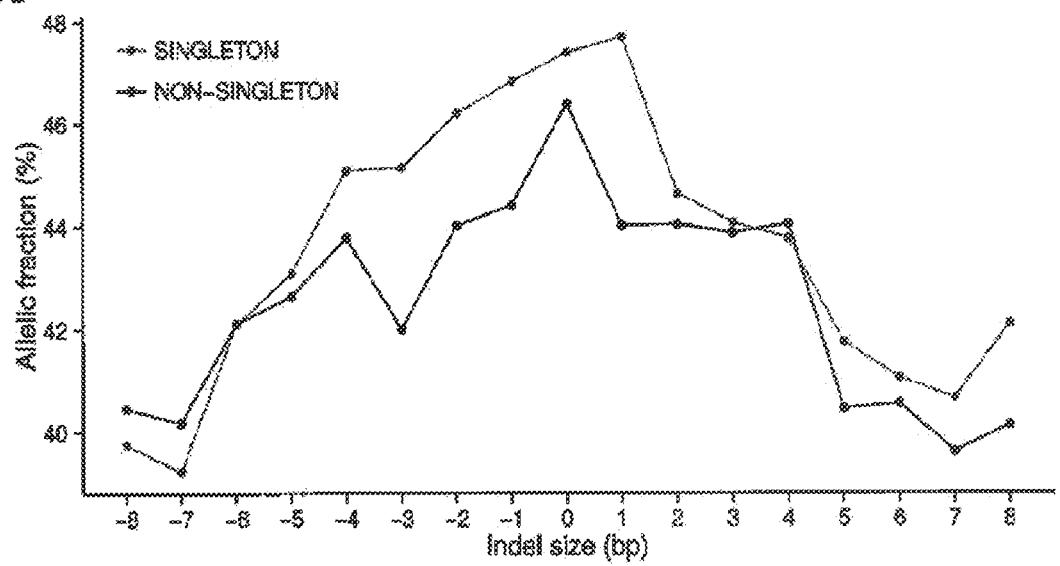

Due to enrichment bias in exome libraries, allelic fractions for inherited heterozygous mutations are not expected to be centered around 50%. The average expected allelic fraction for the alternate allele of a heterozygous single nucleotide polymorphisms (SNPs) is actually 47%±4% (FIG. 6). For indels, this value is even lower, likely due to a mix of enrichment bias, sequence misalignment, and improper reporting of allelic counts for some complicated indels from the Haplotype Caller from the Genome Analysis Toolkit prior to version 3.2 (FIG. 7A,B). Therefore depending on the exome library used, different thresholds are applied for SNPs and indels for the purpose of identifying putative somatic mutations.

Putative somatic mutations include but are not limited to those alleles satisfying the following criteria:

1) non-silent/disruptive nucleotide changes, indels, missense mutations, frameshifts, stop mutations (addition or deletion), read-through mutations, splice mutations;
2) confirmed change not due to a sequencing error or artifact of the testing system.

In embodiments, the mutation is a putative somatic mutation if:
a) the mutation is a SNV;
b) the mutation results in a disruptive change in the encoded polypeptide or regulation of the gene;
c) the mutation has an allelic fraction above 10%; and
d) the mutation includes changes in regions other than those identified as being prone to errors and artifacts, including but not limited to, e.g., low sequence complexity, high GC content, repetitive elements, and the like.

Inclusive somatic mutations are defined as those alleles satisfying the following criteria:
1) SNVs or indels of length one or two base pairs or more;
2) disruptive mutation;
3) allelic fraction above 5%; and
4) not a false positive.

In the context of the cohort of patients analyzed herein, samples are classified as indicative of likelihood of clonal haematopoiesis and/or progress towards a cancerous state if the sample comprises at least one of:
(i) 3 or more exomic putative somatic mutations;
(ii) 0.1 putative somatic mutation per megabase of sequenced DNA; or
(iii) 50 putative somatic mutations per genome.

Subjects which are positive as assessed by somatic mutation analysis considered at increased risk of developing cancer and/or having a higher proportion of haematopoietic clones, as for the foregoing subjects which are judged positive on the basis of specific gene mutations.

In embodiments of the present invention, the analysis of the genomes of single cells by single cell sequencing can be used to provide information about the relationship between mutations and cell types. For example, the presence of a mutation in multiple cells of a defined cell type can further strengthen the conclusion that the mutation is clonal. Moreover, the presence of more than one mutation in a single cell can be evidence of clonal expansion, if the mutations are repeated ly found together, The presence of multiple somatic mutations, as set forth above, can be an indicator of clonal hematopoiesis even in the absence of the presence of driver mutations, for instance the driver mutations identified herein. Accordingly, sequencing in accordance with the present invention can comprise sequencing of genome, exome or specific genes in pooled cells from a sample, such as a blood sample, to identify the presence of driver mutations and/or putative somatic mutations. Alternatively, or in addition, sequencing can comprise the sequencing of the genome, exome or specific genes of one or more single cells, in order to identify the presence of mutations in genes in specific cell types. Initial screens can comprise sequencing to identify driver mutations in a sample, or the presence of putative somatic mutations in a sample. Samples testing positive can be followed dup by single cell sequencing to identify the cell types which harbor the specific mutations, and the identity of mutations which occur together in a single cell.

Subjects can accordingly be subjected to treatment for cancer conditions, including wherein for example (a) the treatment comprises treating said subject by reducing the incidence of haematopoietic clones comprising said mutation in the subject's blood or (b) the treatment or monitoring includes repeating the method as to the subject monthly, bi-monthly or quarterly and treating said subject by reducing the incidence of haematopoietic clones comprising said mutation in the subject's blood or (c) the treatment or monitoring comprises including the subject as a candidate to receive a bone marrow transplant, or (d) the treatment or monitoring includes administering to the subject a bone marrow transplant, or (e) transfusing the subject with blood in which said mutations are absent.

Blood in which mutations are absent can be autologous blood, derived from blood samples taken from the same patient at an earlier point in time; including for example cord blood. Alternatively, or in addition, the blood in which mutations are absent can be allogenic blood, derived from an individual in which the mutations are absent.

In embodiments, a bone marrow transplant can be effected.

Initial detection of clonal haematopoiesis can justify more frequent screening to detect the presence of cooperating mutations at low allele frequencies that presage cancer.

In addition, the use of DNA sequencing to ascertain at-risk cohorts and monitor clonal expansions, as reported here, will facilitate clinical trials of prevention strategies to reduce progression to malignancy.

Clonal haematopoiesis is also a marker for declining health of HSC populations, potentially reflecting aging, attrition, and a declining ability to contain novel neoplasms.

The subject, as referred to herein, is preferably a mammal and advantageously a human. It has been observed that clonal expansion can be determined with rapidly increasing frequency in human subjects of 50 years of age or more. This is in contrast with methods of the prior art, in which clonal expansion is only apparently significant in subjects of greater age, such as 60 or 70 years of age.

Accordingly, there is defined a population of subjects which are tested using any of the methods set forth in accordance with the present invention, wherein that population of subjects comprises humans of at least 50 years of age.

Further populations of subjects which are tested using any of the methods of the present invention comprise subjects undergoing cancer therapy, such as chemotherapy or radiotherapy; these therapeutic approaches increase the risk of developing haematopoietic malignancies and the promotion of haematopoietic clones.

Other populations include subjects which have been exposed to a carcinogen, such as for example tobacco products and/or organic solvents such as textile dyes, paints or inks, and/or red meat, for example grilled, fried or roasted red meat, a virus, ionising radiation or a heavy metal compound such as a lead compound.

There are many methods known in the art for determining the genotype of a patient and for identifying or analyzing whether a given DNA sample contains a particular somatic mutation. Any method for determining genotype can be used for determining genotypes in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, nucleic acid hybridization, polymerase chain reaction (PCR), RFLP analysis and size chromatography (e.g., capillary or gel chromatography), all of which are well known to one of skill in the art.

The methods of the present invention, such as whole exome sequencing and targeted amplicon sequencing, have commercial applications in diagnostic kits for the detection of the somatic mutations in patients. A test kit according to the invention may comprise any of the materials necessary for whole exome sequencing and targeted amplicon sequencing, for example, according to the invention. In a particular advantageous embodiment, a diagnostic for the present invention may comprise testing for any of the genes in disclosed herein. The kit further comprises additional means, such as reagents, for detecting or measuring the sequences of the present invention, and also ideally a positive and negative control.

The present invention further encompasses probes that are immobilized on a solid or flexible support, such as paper, nylon or other type of membrane, filter, chip, glass slide, microchips, microbeads, or any other such matrix, all of which are within the scope of this invention. The probe of this form is now called a "DNA chip". These DNA chips can be used for analyzing the somatic mutations of the present invention. The present invention further encompasses arrays or microarrays of nucleic acid molecules that are based on one or more of the sequences described herein. As used herein "arrays" or "microarrays" refers to an array of distinct polynucleotides or oligonucleotides synthesized on a solid or flexible support, such as paper, nylon or other type of membrane, filter, chip, glass slide, or any other suitable solid support. In one embodiment, the microarray is prepared and used according to the methods and devices described in U.S. Pat. Nos. 5,446,603; 5,545,531; 5,807,522; 5,837,832; 5,874,219; 6,114,122; 6,238,910; 6,365,418; 6,410,229; 6,420,114; 6,432,696; 6,475,808 and 6,489,159 and PCT Publication No. WO 01/45843 A2, the disclosures of which are incorporated by reference in their entireties.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from the FTP site for Blast at the Washington University in St. Louis website. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as (Nref−Ndif)*100/−Nref, wherein Ndif is the total number of non-identical residues in the two sequences when aligned and wherein Nref is the number of residues in one of the sequences. Hence, the DNA sequence AGTCAGTC will have a sequence identity of 75% with the sequence AATCAATC (N Nref=8; N Ndif=2). "Homology" or "identity" can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA 1983; 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences. Without undue experimentation, the skilled artisan can consult with many other programs or references for determining percent homology.

The invention further encompasses kits useful for screening nucleic acids isolated from one or more patients for any of the somatic mutations described herein and instructions for using the oligonucleotide to detect variation in the nucleotide corresponding to one or more of the somatic mutations, such as but not limited to, one or more genes selected from the group consisting of DNMT3A, TET2, ASXL1, PPM1D and JAK2 of the isolated nucleic acid.

In other embodiments of this invention, the step of assaying is selected from the group consisting of: restriction fragment length polymorphism (RFLP) analysis, minisequencing, MALDI-TOF, SINE, heteroduplex analysis, single strand conformational polymorphism (SSCP), denaturing gradient gel electrophoresis (DGGE) and temperature gradient gel electrophoresis (TGGE).

The present invention also encompasses a transgenic mouse which may express one or more of the herein disclosed somatic mutations. Methods for making a transgenic mouse are well known to one of skill in the art, see e.g., U.S. Pat. Nos. 7,709,695; 7,667,090; 7,655,700; 7,626,076; 7,566,812; 7,544,855; 7,538,258; 7,495,147; 7,479,579; 7,449,615; 7,432,414; 7,393,994; 7,371,920; 7,358,416; 7,276,644; 7,265,259; 7,220,892; 7,214,850; 7,186,882; 7,119,249; 7,112,715; 7,098,376; 7,045,678; 7,038,105; 6,750,375; 6,717,031; 6,710,226; 6,689,937; 6,657,104; 6,649,811; 6,613,958; 6,610,905; 6,593,512; 6,576,812; 6,531,645; 6,515,197; 6,452,065; 6,372,958; 6,372,957; 6,369,295; 6,323,391; 6,323,390; 6,316,693; 6,313,373; 6,300,540; 6,255,555; 6,245,963; 6,215,040; 6,211,428; 6,201,166; 6,187,992; 6,184,435; 6,175,057; 6,156,727; 6,137,029; 6,127,598; 6,037,521; 6,025,539; 6,002,067; 5,981,829; 5,936,138; 5,917,124; 5,907,078; 5,894,078; 5,850,004; 5,850,001; 5,847,257; 5,837,875; 5,824,840; 5,824,838; 5,814,716; 5,811,633; 5,723,719; 5,720,936; 5,688,692; 5,631,407; 5,620,881; 5,574,206 and 5,569,827. The transgenic mouse may be utilized to mimic haematopoietic disease conditions and may be useful to test novel treatments for blood cancer diseases disease in a mouse model.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Identification of Characteristic Mutations and Candidate Drivers in Clonal Haematopoiesis The exome sequences from 12,380 individuals were analysed and 3,111 putative somatic mutations identified based on their presence at unusual allelic fractions corresponding to an average of approximately one putative somatic mutation for every four subjects.

In detail, a total of 12,380 Swedish research participants with psychiatric diagnoses (Table S1) were ascertained from the Swedish National Hospital Discharge Register, which captures all inpatient hospitalizations. Controls were randomly selected from population registers. We treated cases and controls as a single cohort for all analyses presented below, as none of the mutational variables analyzed below showed any relationship to psychiatric diagnosis after controlling for other factors such as age and smoking.

Excluding bipolar subjects, medical histories (from 1965 to 2011) of 11,164 of the subjects enrolled in the study were extracted from the Swedish national in- and outpatient register (median follow-up was 32 months). Information about vital status (from 2006 to 2012) was extracted from the population register and the Cause of Death register (median follow-up was 42 months). To identify individuals with haematologic malignancies, we included diagnoses within ICD10 code groups C81-C96 (malignant neoplasms of lymphoid, haematopoietic and related tissue), D45 (polycythemia vera), D46(myelodysplastic syndromes), D47 (other neoplasms of uncertain behavior of lymphoid, haematopoietic and related tissue), and D7581 (myelofibrosis) and the same diagnoses within the corresponding ICD9 and ICD8 groups.

Sequencing data were aligned against the GRCh37 human genome reference using BWA ALN version 0.5.9. (Li, H. & Durbin, R. Fast and accurate short read alignment with Burrows-Wheeler transform. *Bioinformatics* 25, 1754-1760 (2009)) On average across samples each base pair of the target intervals was observed 95 times.

Genotypes and allelic counts were computed across the genome using the Haplotype Caller from the Genome Analysis Toolkit version 3.1-1 (McKenna, A. et al. The Genome Analysis Toolkit: A MapReduce framework for analyzing next-generation DNA sequencing data. *Genome Res.* 20, 1297 (2010)), which generated genotypes for 1,812,331 variant sites across 12,380 subjects. Due to the specific default parameters used by the Haplotype Caller and aimed at genotyping inherited mutations, we recognized that several mutations present in sequencing reads in the 5-10% allele fraction range, and that could have been called, were not reported. To mitigate this issue, we used the Unified Genotyper from the Genome Analysis Toolkit to genotype 208 variants reported as seen seven or more times in haematopoietic or lymphoid cancers in the Catalogue Of Somatic Mutations In Cancer (COSMIC) database3 v69 (released Jun. 2, 2014), with the exception of a few that we deemed inherited mutations or PCR sequencing artifacts rather than somatic events (Table S2). We kept all mutations for which the alternate allele was observed on at least three sequencing reads in an individual's sequencing data. These thresholds yielded 26 additional mutations that were not called by the Haplotype Caller. We did not use these mutations for our unbiased analysis of enrichment of disruptive mutations.

Definition of Putative, Inclusive, and Candidate Driver Somatic Mutations

Due to the higher likelihood of misalignment and PCR artifacts, we excluded from analysis somatic mutations in the following regions:
1) Low complexity regions and sites harboring markers failing Hardy Weinberg equilibrium tests in the 1000 Genomes Project phase 1: see Github files: lh3/varcmp/blob/master/scripts/LCR-hs37d5. bed.gz and https://github.com/lh3/varcmp/blob/master/scripts/1000g.hwe-bad.bed)
2) Sites with excess coverage within the 1000 Genomes Project phase 1
3) Segmental duplications of the human genome (see UCSC Genome Browser hg19 database: goldenPath/hg19/database/genomicSuperDups.txt.gz)
4) Regions excluded from the strict mask of the 1000 Genomes Project phase 1 (see 1000 Genomes Project data hosted by the European Bioinformatics Institute FTP site: vol1/ftp/phase1/analysis_results/supporting/accessible_genome_masks/20120 824_strict_mask.bed)

These filters defined regions covering ~60% of the GRCh37 human genome reference and ~70% of the coding regions and they excluded 161,158 out of the 1,812,331 variants called in the cohort.

Due to enrichment bias in exome libraries, allelic fractions for inherited heterozygous mutations are not expected to be centered around 50%. The average expected allelic fraction for the alternate allele of a heterozygous single nucleotide polymorphisms (SNPs) is actually 47%±4% (FIG. 6). For indels, this value is even lower, likely due to a mix of enrichment bias, sequence misalignment, and improper reporting of allelic counts for some complicated indels from the Haplotype Caller from the Genome Analysis Toolkit prior to version 3.2 (FIG. 7A,B). Therefore we decided to apply different thresholds for SNPs and indels for the purpose of identifying putative somatic mutations.

For this cohort, we define as putative somatic mutations those alleles satisfying the following criteria:
1) SNVs
2) Observed once or twice (minor allele frequency less than 0.01%) in this cohort
3) Allelic fraction above 10%
4) Failed the hypothesis that the alternate allelic count was distributed as a binomial process with mean 45% with a designed false positive rate of $10^{-5}$ We define as inclusive somatic mutations those alleles satisfying the following criteria:
1) SNVs or indels of length one or two base pairs
2) Observed at most six times (minor allele frequency less than 0.025%) in the cohort
3) Allelic fraction above 5%
4) Failed the hypothesis that the alternate allelic count was distributed as a binomial process with mean 47% for SNVs and 40% for indels with a designed false positive rate of 0.01.

Figure 8:
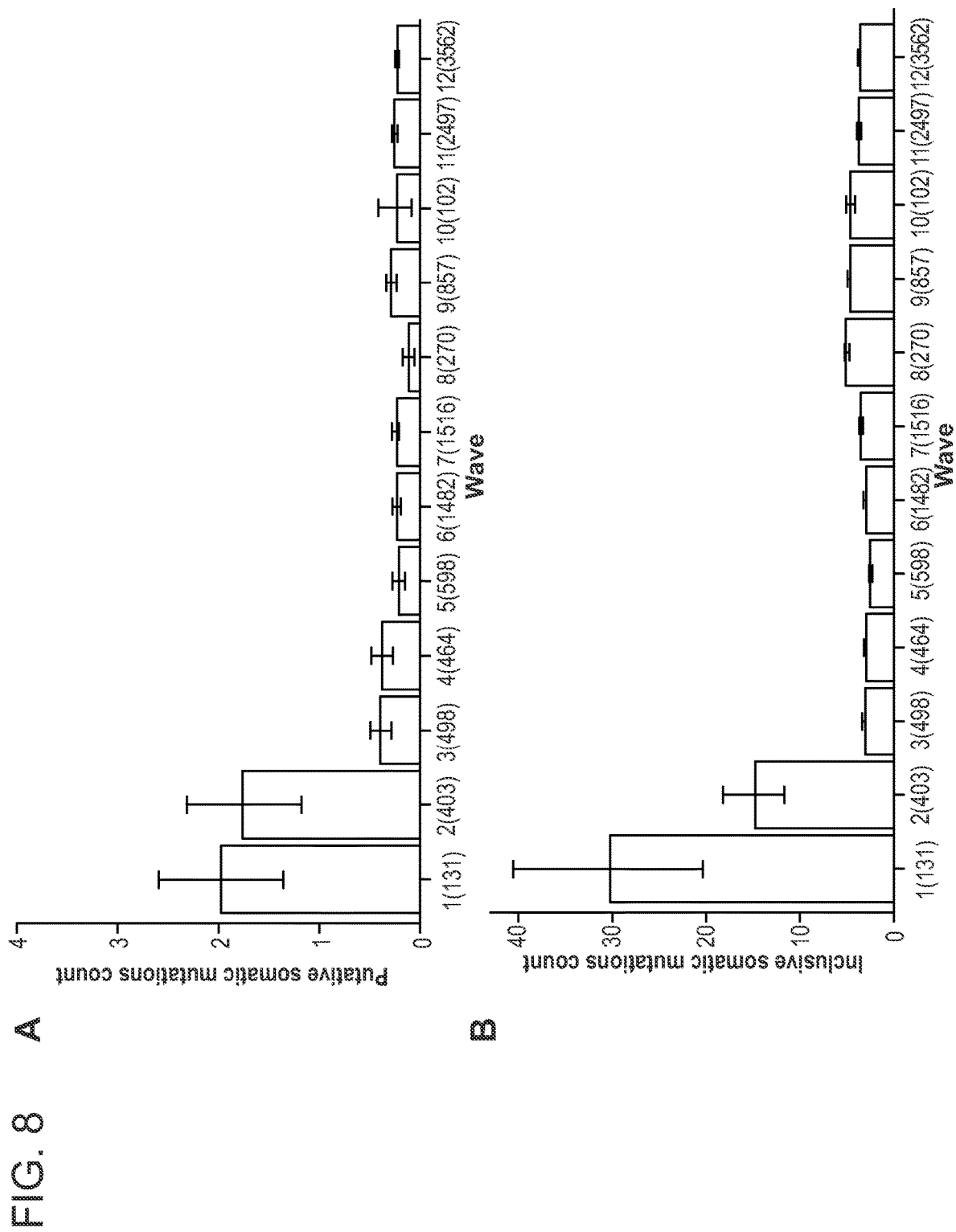
FIG. 8A-8B Putative somatic mutations detected across sequencing waves. Panel A and B show, respectively putative and inclusive somatic mutations stratified by sequencing waves. The first two waves exhibit an increase in detection of somatic mutations likely due to older protocols used for library preparation and sequencing.

These definitions yielded 4,275 putative somatic mutations and 53,474 inclusive somatic mutations across 12,380 subjects. Upon further analysis, a large fraction of these mutations originated from the first two sequencing waves (FIG. 8A,B). This likely reflected older capture and sequencing technologies used during the first two waves. We also observed a single outlier subject from the sixth sequencing wave, with 193 putative somatic mutations and 1,207 inclusive somatic mutations. Putative somatic mutations from this outlier failed to validate in an independent experiment.

We excluded the 534 subjects from the first two waves and the outlier subject from any subsequent analyses in which putative or inclusive somatic mutations were used. This resulted in a refined set of 3,111 putative somatic mutations and 42,282 inclusive somatic mutations from 11,845 subjects.

Figure 9A:
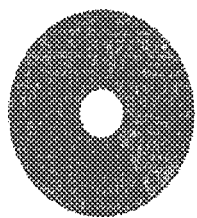
FIG. 9A-9F Mutation profiles for different mutation groups. Panel A shows the profile for mutations observed once or twice (minor allele frequency <0.01%) in the cohort. Panel B shows profile for putative somatic mutations from waves 3 to 12 excluding one outlier from wave 6. Panel C shows profile for inclusive somatic mutations from waves 3 to 12 excluding one outlier from wave 6. Panel D shows profile for inclusive somatic mutations from wave 1. Panel E shows profile for inclusive somatic mutations from wave 2. Panel F shows profile for inclusive somatic mutations from the outlier from wave 6.
Figure 9B:
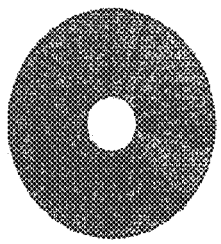
Figure 9C:
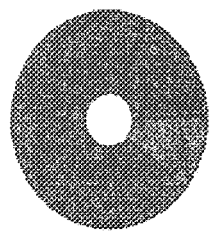
Figure 9D:
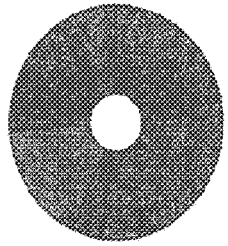
Figure 9E:
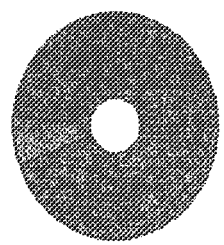
Figure 9F:
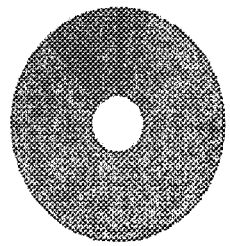

Mutational profiles for inherited mutations (FIG. 9A) resemble mutational profiles for inclusive and putative somatic mutation sets (FIG. 9B,C) suggesting that technical artifacts, rather than genuine somatic and inherited mutations, must constitute a small fraction of the two sets. By contrast, the mutational profiles for inclusive somatic mutations from the first two sequencing waves (FIG. 9D,E) were quite different, and so were the mutational profiles for inclusive somatic mutations in the outlier subject from the sixth sequencing wave (FIG. 9F), further suggesting that these were library preparation or sequencing artifacts rather than real biological events.

Finally, we define as candidate driver somatic mutations those alleles satisfying the following criteria:
1) Disruptive and missense mutations in gene DNMT3A localized in exons 7 to 23
2) Disruptive mutations in gene ASXL1 with the exclusion of ASXL1 p.G646fsX12 and p.G645fsX58
3) Disruptive mutations in gene TET2
4) Disruptive mutations in gene PPM1D
5) Missense mutation JAK2 p.V617F
6) Mutations reported at least seven times in haematopoietic and lymphoid malignancies using the Catalogue of Somatic Mutations in Cancer3 with the exclusions of inherited mutations and potential PCR artifacts (Table S2)

This definition does not take allelic fractions into account.

Due to low coverage in one small region of ASXL1 (FIG. 10B) we were not able to discern mutation ASXL1 p.G646fsX12, known to account for >50% of mutations in ASXL1 in myeloid malignancies, from potential PCR artifacts.4 Moreover the exome enrichment reagent we used does not capture some exons of TET2 accounting for almost half of the coding region in which other studies have identified mutations10 (FIG. 10C). Therefore mutations in TET2 and ASXL1 were likely under-ascertained in this study.

We performed a validation experiment for 65 mutations selected among putative somatic mutations and candidate driver somatic mutations from 12 subjects. A library preparation method utilizing a two round tailed amplicon PCR strategy was used to create targeted sequencing libraries for sequencing at high coverage on an Illumina MiSeq instrument. Alignment of sequencing reads against the GRCh37 human genome reference was performed using BWA MEM version 0.7.711 and allelic fractions were computed using the Unified Genotyper from the Genome Analysis Toolkit version 3.2-2.2

Figure 11:
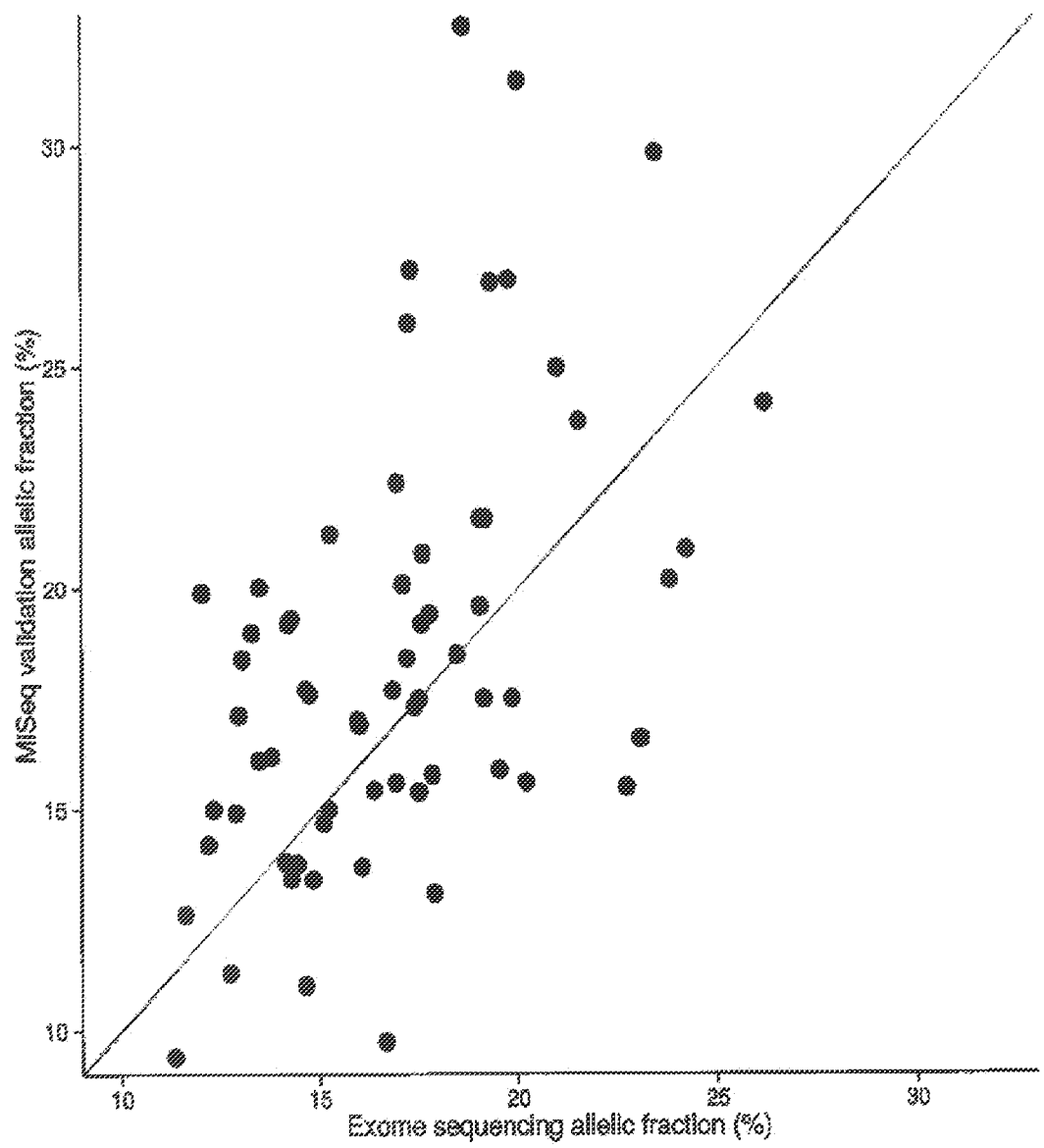
FIG. 11 Validation experiment for 65 putative somatic mutations and candidate driver somatic mutations from 12 subjects selected for carrying one or more candidate driver somatic mutations using an Illumina MiSeq instrument. Pearson's correlation coefficient for the allelic fractions in the two experiments was r2 0.25 (P<0.001).

For 65 of 65 mutations tested, molecular validation confirmed that the mutant allele was present at a low allelic fraction (significantly less than 50%) and thus could not have been inherited (FIG. 11).

Example 2: DNMT3A and Other Driver Mutations

Figure 12:
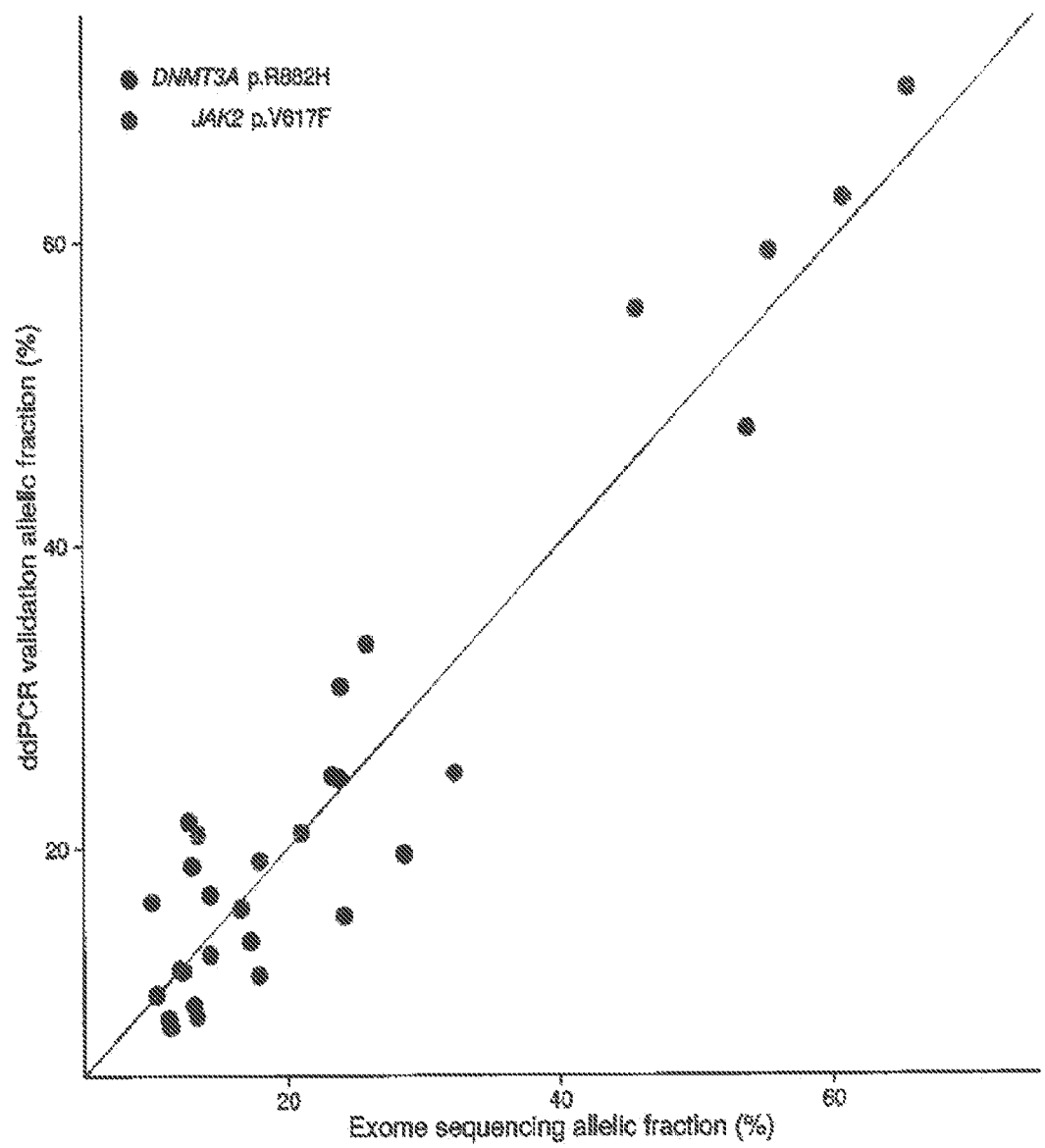
FIG. 12 Validation experiment for 30 candidate driver somatic mutations, 18 JAK2 p.V617F mutations, and 12 DNMT3A p.R882H mutations, using a droplet-based digital PCR (ddPCR) system. Pearson's correlation coefficient for the allelic fractions in the two experiments was r2 0.90 (P<0.001).

We further performed validation for 30 candidate driver somatic mutations from two well-known recurrently mutated sites, DNMT3A p.R882H and JAK2 p.V617F. These were genotyped using TaqMan fluorescent assays in a droplet-based digital PCR system.12 Relative concentrations of each allele were quantitated through multiplexed fluorophores counted across approximately 15,000 nanoliter-sized droplets. Each somatic mutation that we attempted to validate was confirmed as somatic, including five JAK2 p.V617F mutations mutations showing at allelic fractions close to or above 50% (FIG. 12), as would be expected as a consequence of a loss-of-heterozygosity event (Kralovics, R. et al. A gain-of-function mutation of JAK2 in myeloproliferative disorders. *N. Engl. J. Med.* 352, 1779-1790 (2005)).

A total of 190 mutations across 185 subjects were identified in the DNMT3A gene (Table S4). Studies of mutations in haematologic malignancies have found DNMT3A mutations to be more common in cancers from females than in cancers from males (Markova, J. et al. Prognostic impact of DNMT3A mutations in patients with intermediate cytogenetic risk profile acute myeloid leukemia. *Eur. J. Haematol.* 88, 128-135 (2012); Roller, A. et al. Landmark analysis of DNMT3A mutations in hematological malignancies. *Leukemia* 27, 1573-1578 (2013)). We found that DNMT3A somatic mutations were also more common in females than in males (104/5780 vs. 81/6600; P=0.016 after adjusting for age using a linear regression model). We observed 48 disruptive mutations, and 142 in-frame indels or missense mutations including 23 mutations affecting the R882 amino acid of which 15 are R882H mutations known to dominantly inhibit wild-type DNMT3A (Russler-Germain, D. A. et al. The R882H DNMT3A Mutation Associated with AML Dominantly Inhibits Wild-Type DNMT3A by Blocking Its Ability to Form Active Tetramers. *Cancer Cell* 25, 442-454 (2014)). We also observed an enrichment within the DNMT3A FF interface region bounded by amino acid F732 and amino acid F772 (Jurkowska, R. Z. et al. Oligomerization and binding of the Dnmt3a DNA methyltransferase to parallel DNA molecules: heterochromatic localization and role of Dnmt3L. *J. Biol. Chem.* 286, 24200-24207 (2011)), similarly to what seen in DNMT3A mutations in acute myeloid leukemia (see Lawrence et al., Nature 505, 495-501 (23 Jan. 2014) doi:10.1038/nature12912).

Figure 13A:
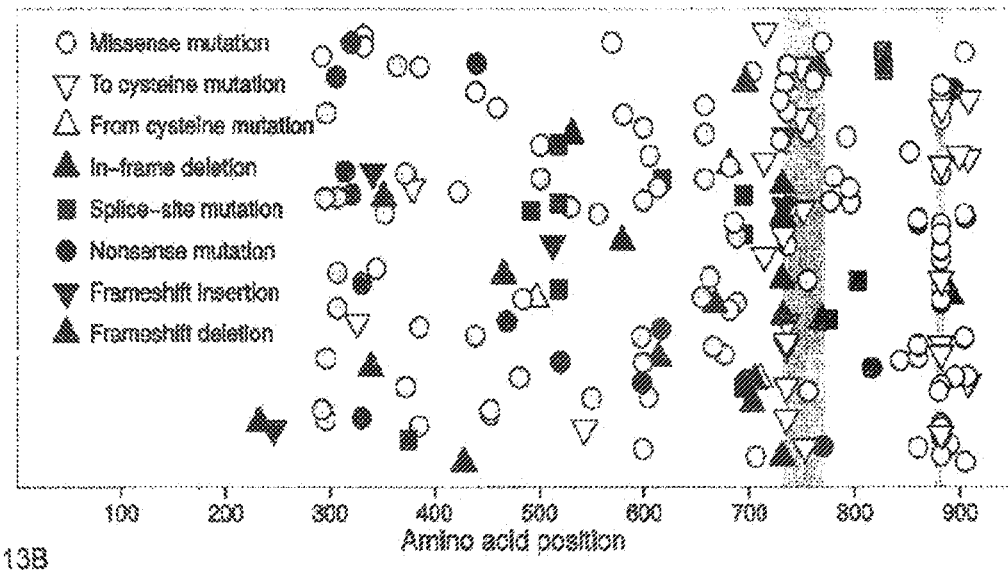
FIG. 13A-13B Mutations observed in the DNMT3A gene. Mutations across the 12,380 subjects in the cohort are visualized in Panel A as a jitterplot and in Panel B as a histogram. Amino acid regions from the FF interface (from F732 to F772) and the RD interface (from D876 to R885) are highlighted in gray.

Of the 20 missense mutations within the FF interface region, 10 generated new cysteine residues (FIG. 13A,B). We posited that these new cysteine residues might inactivate DNMT3A protein function by inappropriately forming disulfide bonds if the protein were exposed to oxidizing environment during its biogenesis or function. We then used the DiANNA disulfide bond prediction tool20 to predict disulphide bond formation for each of the mutant proteins containing a new cysteine residue. Out of 10 different cysteine forming mutations, 8 were predicted to form new disulfide bonds to other native cysteine residues located in the ADD, cysteine-rich, catalytic domain of DNMT3A21 which spans amino acids 472-610 with high prediction scores (0.85±0.24, mean±S.D.) (Table S4). We then used a three-dimensional structure prediction tool22 and were able to predict 51% of DNMT3A sequence (from R476 to F909), including the catalytic domain as well as the FF and RD domains, which are required in oligomerization of DNMT3A.

Figure 14:
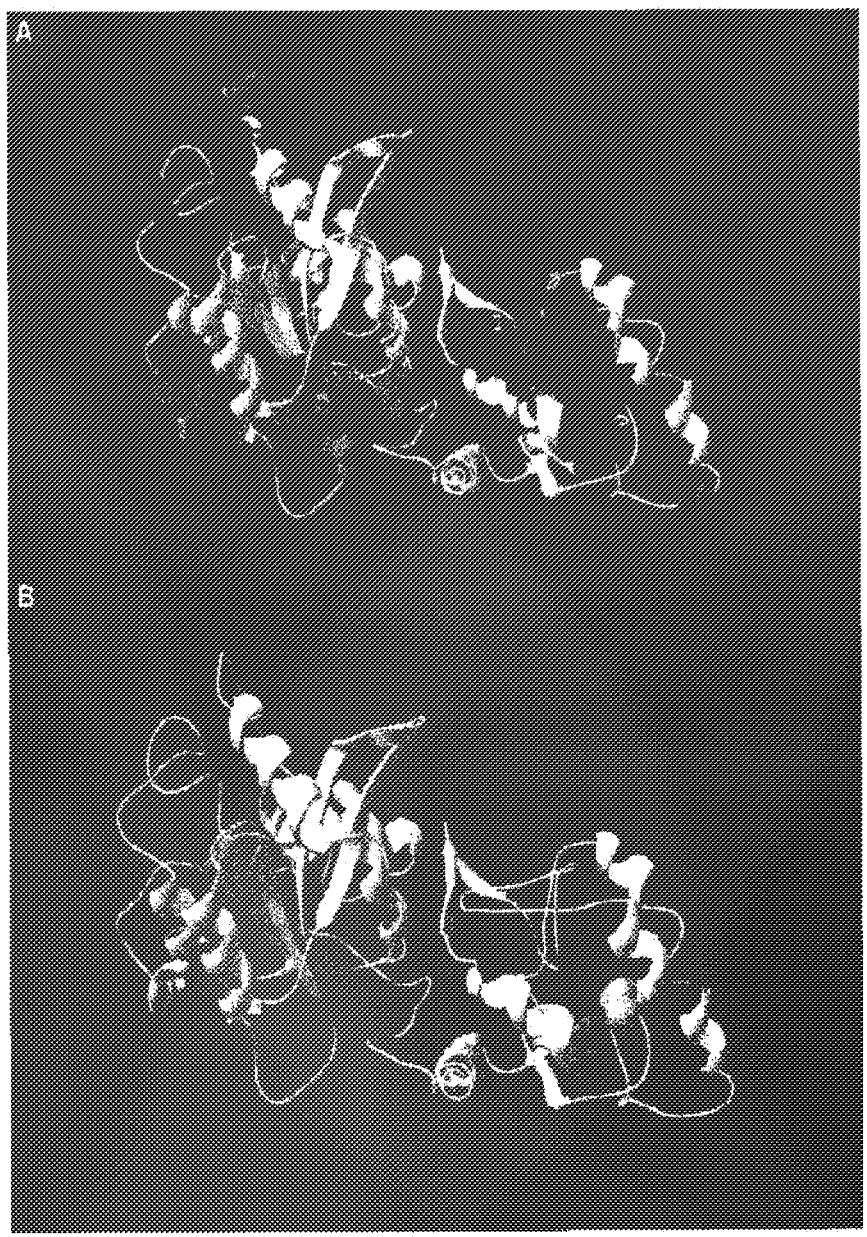
FIG. 14 Tertiary structure for DNMT3A and cysteines introduced by mutations. In Panel A we show the predicted tertiary structure of DNMT3A (51% of the protein sequence, from R476 to F909) showing wild-type cysteine residues (in blue) and amino acid residues substituted into cysteine (in red) found in our analysis. In Panel B we show an example of a predicted disulfide bond in the mutant DNMT3A (F732C) using the DiANNA tool whereby the mutant C732 is predicted to form a disulfide bond with C497 (cyan). Alternatively, these de novo cysteine-forming mutations may also influence the oligomerization dynamics of DNMT3A due to their propensity to exist in the FF and RD domains.

Based on the three-dimensional structure of DNMT3A, most of the predicted de novo disulfide bonds in mutant proteins would lead to severe structural change in the protein by disrupting the catalytic domain or influencing the oligomerization process (FIG. 14A,B).

Our analysis identifies previously unknown cysteine forming mutations in DNMT3A in a cohort of patients, which we predict would lead to loss of enzymatic function.

The vast majority of the mutations were dispersed across the genome. However, four genes (DNMT3A, TET2, ASXL1, and PPM1D) exhibited disproportionately high numbers of somatic mutations. Whereas the 95% of the mutations observed across the genome were missense and synonymous changes, the somatic mutations observed in DNMT3A, TET2, ASXL1, and PPM1D showed a different pattern: they strongly tended to disrupt gene protein-coding sequence by introducing a frameshift, nonsense, or splice-site disruption (commonly called disruptive mutations, though such mutations can also create proteins with altered or disregulated function) (FIG. 2A). Three of these four genes—DNMT3A, TET2, and ASXL1—also tend to harbor such mutations in myeloid malignancies (Ley, T. J. et al. DNMT3A mutations in acute myeloid leukemia. *N. Engl. J. Med.* 363, 2424-2433 (2010); Delhommeau, F. et al. Mutation in TET2 in myeloid cancers. *N. Engl. J. Med.* 360, 2289-2301 (2009); Gelsi-Boyer, V. et al. Mutations of polycomb-associated gene ASXL1 in myelodysplastic syndromes and chronic myelomonocytic leukaemia. Br. J. Haematol. 145, 788-800 (2009)). All three are proposed to function as epigenetic regulators (Shih, A. H., Abdel-Wahab, O., Patel, J. P. & Levine, R. L. The role of mutations in epigenetic regulators in myeloid malignancies. *Nat. Rev. Cancer* 12, 599-612 (2012)).

The fourth implicated gene, PPM1D, which functions as a regulator of p53, has been described more frequently as mutated in malignancies of other cell types (Chuman, Y. et al. PPM1D430, a novel alternative splicing variant of the human PPM1D, can dephosphorylate p53 and exhibits specific tissue expression. *J. Biochem.* (Tokyo) 145, 1-12 (2009)). Of the 15 protein-truncating mutations observed in PPM1D, 12 occurred in the last exon, which is also the site of protein-truncating mutations described in cancer patients (Ruark, E. et al. Mosaic PPM1D mutations are associated with predisposition to breast and ovarian cancer. *Nature* 493, 406-410 (2013); Kleiblova, P. et al. Gain-of-function mutations of PPM1D/Wip1 impair the p53-dependent G1 checkpoint. *J. Cell Biol.* 201, 511-521 (2013); Akbari, M. R. et al. PPM1D mutations in circulating white blood cells and the risk for ovarian cancer. J. Natl. Cancer Inst. 106, djt323 (2014); Zhang, L. et al. Exome sequencing identifies somatic gain-of-function PPM1D mutations in brainstem gliomas. *Nat. Genet.* 46, 726-730 (2014)). Loss of the C-terminal localization domain of PPM1D is reported to activate PPM1D, repress p53, and thereby impair the p53-dependent G1 checkpoint, promoting proliferation.

Figure 13B:
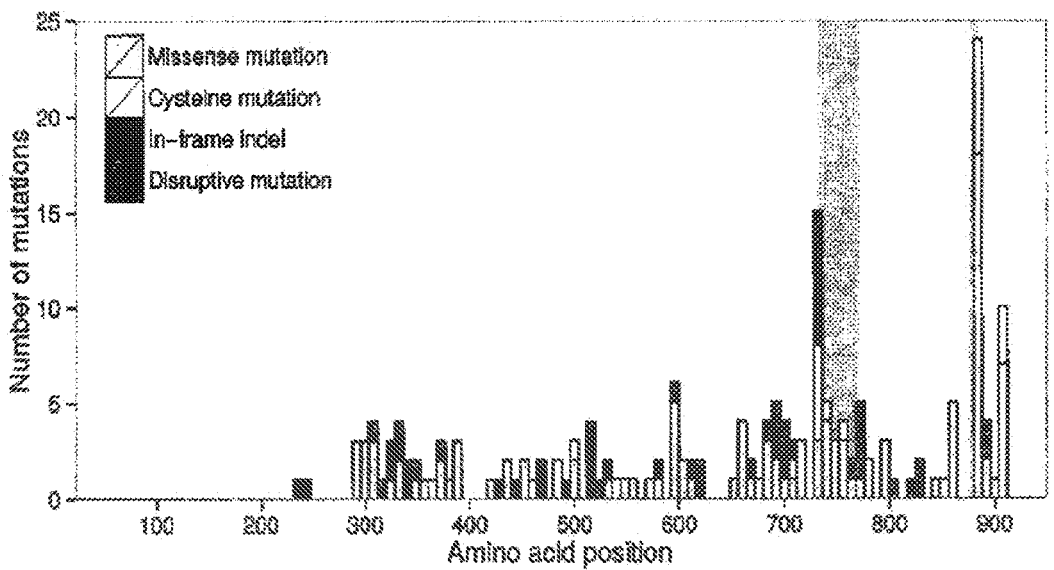

In addition to these disruptive mutations, DNMT3A also exhibited a strong (P<0.001) excess of missense mutations (FIG. 2A). Somatic missense mutations in DNMT3A were all localized in exons 7 to 23 and were enriched for cysteine-forming mutations (FIG. 13). Such mutations potentially exert a dominant-negative effect on the tetrameric DNMT3A protein complex (see FIG. 14 for details).

Because DNMT3A, TET2, and ASXL1 are frequently mutated in haematological malignancies, we hypothesized that other recurring cancer mutations might also promote clonal haematopoiesis. We therefore considered 208 specific variants that have been reported in the Catalogue of Somatic Mutations in Cancer (Forbes, S. A. et al. COSMIC: mining complete cancer genomes in the Catalogue of Somatic Mutations in Cancer. Nucleic Acids Res. 39, D945-950 (2011)) to be mutated frequently (found in at least seven patients) in haematopoietic and lymphoid malignancies. We found 98 of these recurring mutations in our cohort, with 56 occurring in genes other than DNMT3A, TET2, ASXL1, and PPM1D. These recurrent mutations included the gain-of-function mutation JAK2 p.V617F found in 24 subjects; the DNMT3A mutation p.R882H (a proposed dominant negative; Russler-Germain, D. A. et al. The R882H DNMT3A Mutation Associated with AML Dominantly Inhibits Wild-Type DNMT3A by Blocking Its Ability to Form Active Tetramers. Cancer Cell 25, 442-454 (2014)) found in 15 subjects and the SF3B1 mutation p.K700E found in 9 subjects (Papaemmanuil, E. et al. Somatic SF3B1 mutation in myelodysplasia with ring sideroblasts. N. Engl. J. Med. 365, 1384-1395 (2011)). These mutations—including both the recurring, cancer-associated mutations and the disruptive mutations in DNMT3A, TET2, ASXL1, and PPM1D described above—comprised a set of 327 candidate driver somatic mutations for clonal haematopoiesis across 14 genes in 308 subjects (FIG. 2B and Table S3), with 18 subjects carrying multiple such mutations (FIG. 2C). DNMT3A had the most observed mutations (190), followed by ASXL1 (35) and TET2 (31). We note that mutations in TET2 and ASXL1 were likely under-ascertained for technical reasons (FIG. 10B,C).

Example 3: Clonal Haematopoiesis with Unknown Drivers

Somatic mutations may either be "drivers" that contribute to clonal expansion or simply passive "passengers". We tested whether subjects with clonal haematopoiesis with candidate drivers (CH-CD) also tended to carry additional putative somatic mutations. Subjects with CH-CD did indeed tend to carry more putative somatic mutations overall (mean 1.5, in addition to the candidate driver mutations themselves) than subjects without candidate drivers did (mean 0.23, FIG. 2D); this observation remained significant after correcting for age (P<0.001).

Some 459 subjects had multiple putative somatic mutations without any of the candidate drivers described above. When multiple mutations were observed in the same individual, such mutations tended to have more-similar allelic fraction estimates than pairs of somatic mutations ascertained in different individuals (P<0.001, Mann-Whitney test for allelic fraction differences within and between subjects), consistent with the possibility that they were present in the same clone.

Based on these results, we hypothesized that the presence of multiple somatic mutations might itself be an informative marker for clonal haematopoiesis, even when the exome sequencing analysis had not identified a candidate driver mutation. To consider cases of clonal haematopoiesis without obvious driver mutations, we sought to define a highly specific criterion for clonal haematopoiesis that depended only on the number (rather than identity) of the mutations. We identified 3,111 putative somatic mutations present at unusual allelic fractions. Whereas most individuals (9,927) had no putative somatic mutations, 1,333 had one; 313 had two; and 272 had from three up to eighteen (with 545 having sequence data of insufficient quality for detection). This distribution suggested that even if a random ("Poisson") process generated many of the mutations observed in individuals with one or two mutations, a Poisson process (with a constant mean) could not explain the surprisingly high numbers of individuals with three to eighteen detectable mutations. In our analyses below, we classified subjects carrying three or more putative somatic mutations as having clonal haematopoiesis with unknown drivers (CH-UD); there were 195 such subjects.

In some cases of CH-UD, additional analysis suggested potential candidate drivers. Somatic loss of chromosome Y (LOY) is known to be common in elderly men and a potential driver or a marker for clonal haematopoiesis (Forsberg, L. A. et al. Mosaic loss of chromosome Y in peripheral blood is associated with shorter survival and higher risk of cancer. Nat. Genet. 46, 624-628 (2014)). Sequence-coverage measurements across chromosome Y were used to estimate its copy number. Aligned sequencing reads are assigned mapping quality equal to 0 by BWA ALN1 when an alternative equally good alignment was identified by the aligner. Such reads on the sex chromosomes paralogous regions (PAR) have less predictive value to estimate LOY as they might come from the X chromosome even when aligned to the Y chromosome. We therefore measured for each subject:

1) number of sequencing reads over the Y chromosome with mapping quality greater than 0;
2) number of sequencing reads over regions X:1-2699520 (GRCh37 PAR1), X:154931044-155270560 GRCh37 PAR2), and over regions X:88456802-92375509 and Y:2917959-6616600 (GRCh37 PAR3) with mapping quality equal to 0.

We then computed the relative amount of sequencing reads for each subject by dividing those numbers by the total number of aligned reads over the GRCh37 human genome reference for each subject (FIG. 16). Although measurements were quite noisy, likely due to differences in library preparations and sequencing across samples, we could still observe that male subjects with CH-UD had overall less relative coverage over the Y-chromosome than male subjects without clonal haematopoiesis (P<0.001, Mann-Whitney test) and than male subjects with CH-CD (P=0.0089, Mann-Whitney test). Therefore LOY is either a candidate driver mutation itself, possibly due to the presence of a tumor suppressor gene in the Y chromosome, or some other event itself leading to clonal haematopoiesis is a risk factor for LOY. Interestingly, although not statistically significant, coverage for three CH-UD female subjects was also depleted over the sex chromosomes paralogous regions, possibly indicating a loss of chromosome X, an event previously observed in old women (Stone, J. F. & Sandberg, A. A. Sex chromosome aneuploidy and aging. Mutat. Res. 338, 107-113 (1995)).

We found that LOY was more common in male subjects with CH-UD than in male subjects without clonal haematopoiesis (P<0.001, after adjusting for age using a linear regression model) and male subjects with CH-CD (P=0.002, after adjusting for age using a linear regression model). Approximately one fourth of male subjects with CH-UD showed some evidence for somatic LOY (FIG. 15).

Example 4: Clonal Haematopoiesis and Advancing Age

Detectable clonal haematopoiesis with candidate driver mutations (CH-CD) was rare among young individuals (0.74% before the age of 50) but much more common in the older population (5.7% after the age of 65) (FIG. 3A and FIG. 16). Reflecting this relationship, subjects with CH-CD were on average older than subjects without detectable putative somatic mutations (mean of 64 vs. mean of 55; P<0.001, FIG. 2E); DNMT3A, ASXL1, TET2, PPMD1, and JAK2 each showed the pattern seen for candidate drivers as a group, tending to manifest detectable somatic mutations in older individuals (FIG. 2E).

Figure 17:
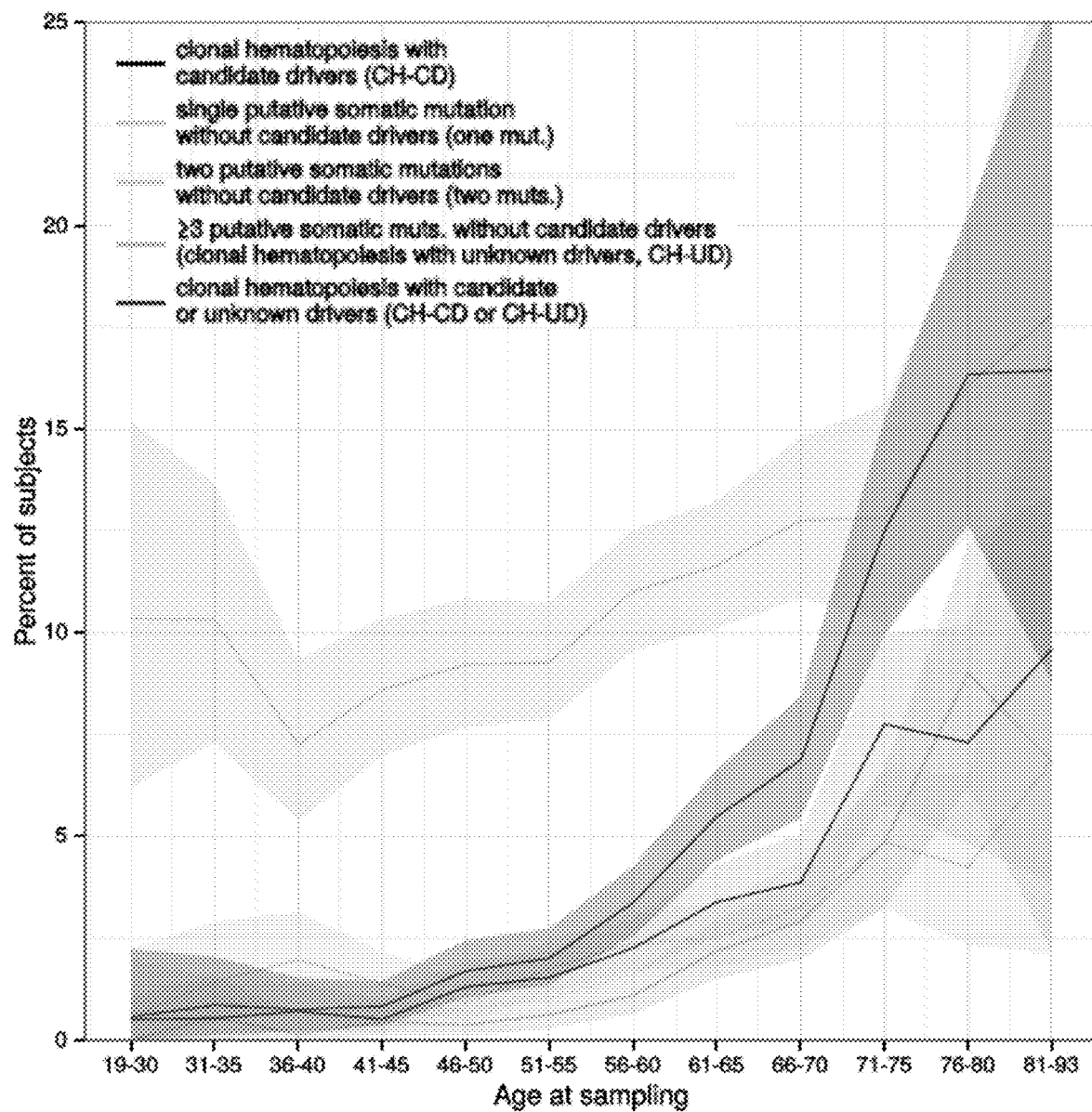
FIG. 17 Prevalence of clonal haematopoiesis as a function of age. Percentage of subjects with clonal haematopoiesis with candidate drivers (CH-CD, in black), subjects carrying exactly one putative somatic mutation and no candidate drivers (one mut., in blue), subjects with exactly two putative somatic mutations and no candidate drivers (two muts., in green), subjects with three or more detectable somatic mutations and no candidate drivers (CH-UD, in gray), and subjects with clonal haematopoiesis with candidate or unknown drivers (CH-CD or CH-UD, in red) within 5-year age bins. Colored bands represent 95% confidence intervals.

Given that 459 subjects had multiple somatic mutations in the absence of candidate driver mutations, we sought to understand the extent to which this state arises dynamically over the lifespan (as opposed to being a lifelong property— for example, due to somatic mutations that occurred in embryonic development; Campbell, I. M. et al. Parental Somatic Mosaicism Is Underrecognized and Influences Recurrence Risk of Genomic Disorders. *Am. J. Hum. Genet.* 95, 1-10 (2014)). We therefore analyzed the age-dependent frequency of somatic genome states defined by the number of putative somatic mutations detected in the exome, excluding all subjects with candidate driver mutations. In contrast to the strongly age-dependent acquisition of CH-CD, the observation of a single somatic mutation in the exome was common at all ages (FIG. 3A and FIG. 16). However, the presence of two detectable putative somatic mutations was more age-dependent, occurring in 1.3% of individuals younger than 50, and 4.0% of individuals older than 65 (FIG. 3B). The presence of three or more putative somatic mutations (our criterion for CH-UD) was more strongly age-dependent, resembling the age trajectory of CH-CD: it occurred in only 0.30% of individuals younger than 50 but 4.6% of individuals older than 65 (FIG. 3C). Overall, clonal haematopoiesis (CH-CD or CH-UD) was observed in 0.94% of subjects younger than 50 but in 10% of those older than 65 (FIG. 3D and FIG. 16). For subjects with clonal haematopoiesis, the average number of detected putative somatic mutations also increased with age (P<0.001, see FIG. 17).

Example 5: Clonal Haematopoiesis and Subsequent Cancer and Mortality

We sought to understand how clonal haematopoiesis relates to subsequent cancer and mortality. Of the 503 individuals with evidence for clonal haematopoiesis (CH-CD or CH-UD), we were able to monitor subsequent medical history (median 33 months; range 2-7 years) in 455. Of these subjects, 15 developed haematological malignancies within three years from DNA sampling, with 8 developing myeloid malignancies and 6 developing lymphoid malignancies (Table S6). The myeloid malignancies arose in three subjects with SRSF2 p.P95H mutations, two subjects with JAK2 p.V617F, one subject with DNMT3A p.P904L, one with TP53 p.R248Q, and one subjects with CH-UD. The lymphoid malignancies arose in one subject with DNMT3A p.H613D, one subject with SF3B1 p.K700E and in four subjects with CH-UD.

Figure 4:
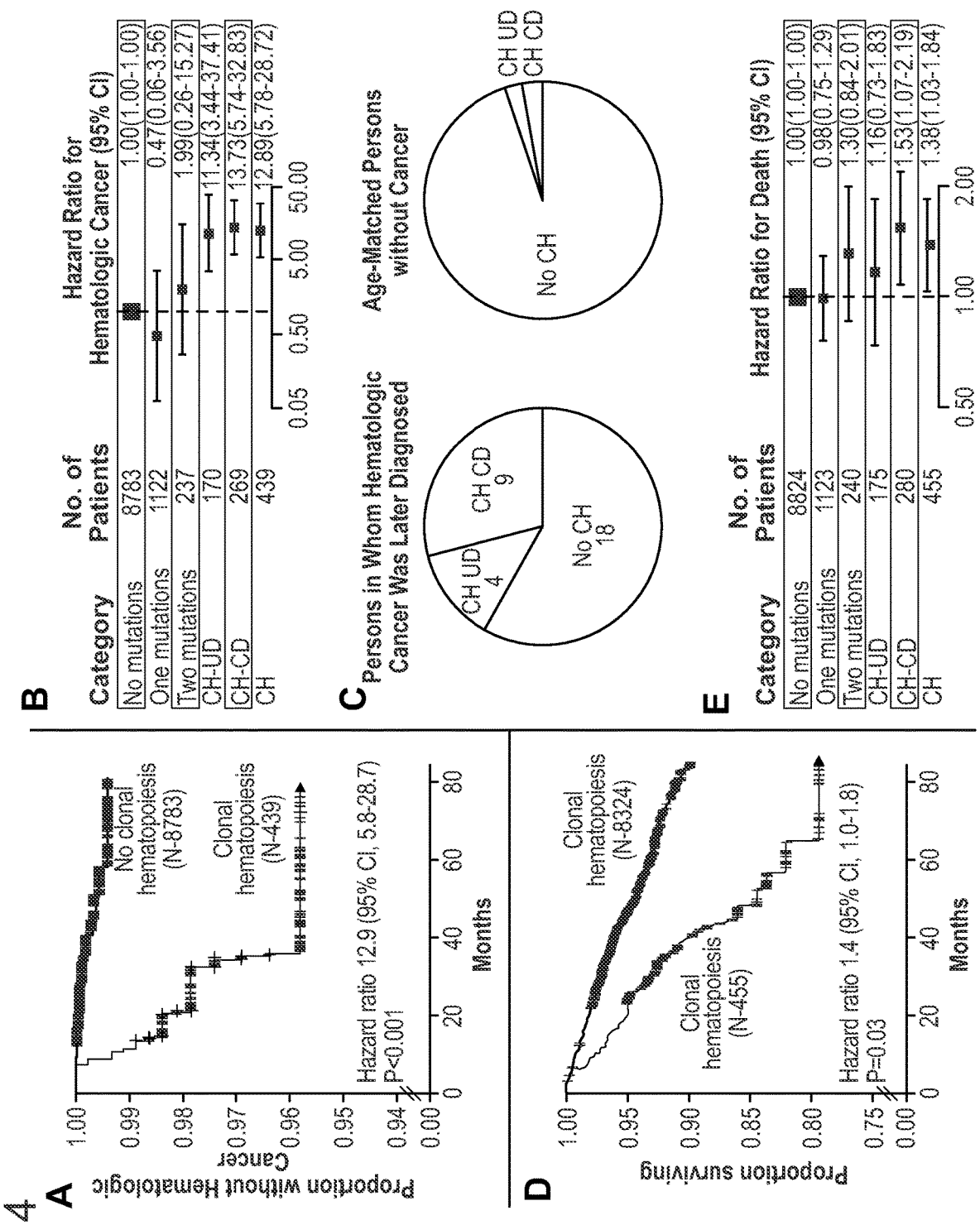
FIG. 4A-4E Risk related to development of haematological malignancies for subjects with clonal haematopoiesis. Panels A and D show Kaplan-Meier plots of the proportions of (A) subjects who remain free of a diagnosis of haematological malignancy and (D) surviving subjects. The x-axis indicates the time (in months) after DNA sampling. Panel C depicts hematological malignancy. Panels B and E show hazard ratios for (B) haematological malignancy and (E) mortality for subjects with exactly one putative somatic mutations and no candidate drivers (one mut.), subjects with exactly two putative somatic mutations and no candidate drivers (two muts.), subjects with clonal haematopoiesis with unknown drivers (CH-UD), subjects with clonal haematopoiesis with candidate drivers (CH-CD), and subjects with clonal haematopoiesis with candidate or unknown drivers (CH), all compared to subjects with no candidate drivers and no putative somatic mutations (no muts.). Panel D shows frequency of subjects with clonal haematopoiesis with candidate or unknown drivers among subjects who developed haematological malignancies in the months after DNA sampling, compared to proportions in an age-matched group of individuals.

There were 55 subjects with a previous diagnosis of haematological malignancy. Of these, 14 showed clonal haematopoiesis (Table S7). Previous history of haematological malignancy was a strong risk factor for clonal haematopoiesis (odds ratio [OR]=6.0; 95% confidence interval [CI] 3.1 to 12; P<0.001, adjusting for age and sex using a linear regression model). There were also 31 subjects (42%) who developed haematological malignancies more than six months after DNA sampling. Of these, 13 showed clonal haematopoiesis (FIG. 4C). Diagnoses of haematological malignancies in these subjects followed DNA sampling by an average of 19 months (range: 7-36 months). Subjects with clonal haematopoiesis were substantially more likely to receive a first diagnosis of haematological malignancy in the 6-36 months after DNA sampling, compared to individuals without any detectable putative somatic mutations (hazard ratio [HR] 13; 95% CI 5.8 to 29; P<0.001 using a Cox proportional hazards model to analyze time to haematological cancer diagnosis, adjusting for age and sex, FIG. 4A). Subjects with CH-CD and CH-UD had similarly elevated risk (FIG. 4B). Subjects with exactly two putative somatic mutations and no candidate driver mutations, a situation just below our threshold for CH-UD, had a milder increase in risk (HR 2.0; 95% CI 0.22 to 13), perhaps representing a mixture of patients with and without clonal haematopoiesis. Subjects with just one detectable somatic mutation did not show elevated risk (FIG. 4B). For subjects with clonal haematopoiesis, the risk of conversion to haematological malignancy was 1.0% per year.

Subjects with clonal haematopoiesis (CH-CD or CH-UD) exhibited reduced overall survival (FIG. 4D) (HR 1.4; 95% CI 1.03 to 1.8; P=0.033 using a Cox proportional hazards model adjusting for age and sex, FIG. 4E) with 54 subjects that died during follow-up (Table S8). In our cohort, this reduced overall survival was explained by deaths from malignancies and by an association of clonal haematopoiesis with smoking (OR=2.2; 95% CI 1.4 to 3.4; P<0.001).

Example 6: Malignant Clones in DNA Samples

Two of the subjects with clonal haematopoiesis were diagnosed with myeloid malignancies just two months after DNA sampling (in both cases, this was their first diagnosis of any malignancy.) We hypothesized that the clone inferred from the exome sequence analysis might have been the malignant clone, at a pre-clinical stage. To evaluate this hypothesis, we performed whole-genome sequencing on both DNA samples to an average coverage of 108 times for each base pair of the genome (see Supplementary Appendix for details).

High coverage whole-genome sequencing data were generated for Subject #1 and Subject #2 who were diagnosed with a myeloid malignancy two months after DNA sampling. Sequencing data were generated using four lanes from an Illumina HiSeq X Ten instrument for each subject with pair ended sequencing reads of 151 base pairs each and aligned against the GRCh37 human genome reference using BWA MEM version 0.7.7.11 Base pairs across the genome were sequenced on average 108 times per subject. Genotypes and allelic counts were computed across the genome using the Haplotype Caller from the Genome Analysis Toolkit version 3.2-2. Mutations of interest were further filtered out if:

1) already in the 1000 Genomes Project phase 1 dataset (see 1000 Genomes Project data hosted by the European *Bioinformatics* Institute FTP site: vol1/ftp/phase1/ analysis_results/integrated_call_sets/ ALL.wgs.integrated_phase1_v3.20101123.snps_indels_sv.sites.vcf.gz)

2) excluded from high confidence regions for the Genome in a Bottle genotype calls for NA1287828 (see Genome in a Bottle data hosted by the National Center for Biotechnology Information FTP site: giab/ftp/data/NA12878/variant_calls/NIST/union13callableMQonlymerged_addcert_nouncert_excludesimplerep_e xcludesegdups_excludedecoy_excludeRepSeqSTRs_noCNVs_v2.18_2mindatasets_5minYesNoRatio.bed.gz)
3) excluded from the strict mask of the 1000 Genomes Project phase 1 (see 1000 Genomes Project data hosted by the European Bioinformatics Institute FTP site: vol1/ftp/phase1/analysis_results/supporting/accessible_genome_masks/20120 824_strict_mask.bed)
4) within low complexity regions see Github files: lh3/varcmp/blob/master/scripts/LCRhs37d5.bed.gz)
5) present in more than two percent of the reads from each subject.

These filters defined a dataset of 69,104 mutations across ~50% of the GRCh37 human genome reference and ~60% of the coding regions. When looking at mutations that failed the hypothesis that the alternate allelic count was distributed as a binomial process with mean 0.5 with a designed false positive rate of 0.01 or mutations at loci sequenced on average more than 200 times per subject, we observed that several of these mutations were clustering in hotspots. Upon further inspection, most of these calls were due to misalignment due to a paralogous region that was partially deleted in the human genome reference. We therefore further filtered out these mutations whenever they were found to be less than 1,000 bp from each other, further defining a refined dataset of 67,919 mutations across the two subjects. All putative somatic mutations were confirmed in whole-genome sequencing data.

Whole-genome sequence analysis of the pre-clinical DNA sample revealed 1,153 putative somatic mutations in Subject #1 and 660 putative somatic mutations in Subject #2 (FIG. 5A,B), providing strong evidence of that a clone had amplified from a single cell being consistent with the median of 0.4 somatic mutations per megabase pairs observed in AML genomes (Lawrence, M. S. et al. Discovery and saturation analysis of cancer genes across 21 tumour types. *Nature* 505, 495-501 (2014)). The modal allelic fractions among these putative somatic mutations was 17.5% (for Subject #1) and 13.5% (for Subject #2) (FIG. 5A,B), suggesting that clone-derived cells represented, respectively, 35% and 27% of circulating, nucleated cells in these patients at the time of DNA sampling. By further analyzing genes associated with AML (Lawrence et al., supra; Cancer Genome Atlas Research Network. Genomic and epigenomic landscapes of adult de novo acute myeloid leukemia. *N. Engl. J. Med.* 368, 2059-2074 (2013)), whole-genome sequence data revealed many known pathogenic mutations to be present at the characteristic allele frequency of the clone (FIG. 5A,B). Subject #1 carried mutations in RUNX1, STAG2, SRSF2, and TET2 at the allelic fractions characteristic of the clone, and also carried an ASXL1 mutation at a slightly higher allelic fraction (potentially consistent with an earlier presence as a founder mutation). Mutations in ASXL1, RUNX1, and STAG2 tend to co-occur in myelodysplastic syndromes (Chen, T.-C. et al. Dynamics of ASXL1 mutation and other associated genetic alterations during disease progression in patients with primary myelodysplastic syndrome. *Blood Cancer J.* 4, e177 (2014)). Subject #2 carried two mutations in CEBPA: an in-frame C-terminal 33 bp insertion, and a frameshift N-terminal deletion. Both types of CEBPA mutations are commonly found in AML and are typically observed to co-occur in the same malignancies; about a fourth of such double-mutated CEBPA AML cases harbor no other known driver mutations (Fasan, A. et al. The role of different genetic subtypes of CEBPA mutated AML. *Leukemia* 28, 794-803 (2014)).

Example 7: Genetic Relationship of Malignancies to Earlier Clones

For two research subjects in the study, we were able to obtain and analyze bone marrow biopsies from their subsequent malignancies at the time of the first diagnosis. The first was Subject #2 (the subject whose earlier DNA sample we also analyzed by whole-genome-sequencing above, revealing the two CEBPA mutations), who was diagnosed with AML two months after DNA sampling. The other subject (Subject #3) was diagnosed with AML 34 months after DNA sampling. For both biopsy samples we generated (i) whole-exome sequence data to identify and measure the allelic fractions of protein-altering mutations, and (ii) low coverage whole-genome sequence data to identify large-scale gains or losses of chromosomal segments.

Whole-exome sequencing data and low coverage whole-genome sequencing data of bone marrow biopsies were generated for Subject #2 and Subject #3. DNA was obtained from the diagnostic specimen available at the Clinical Genetics Department at Uppsala University (biobank application Bba-827-2014-064). 85 ng/μl and 88 ng/μl were obtained for, respectively, Subject #2 and Subject #3 in 10 μl water. The ThruPLEX-FD kit (Rubicon Genonics) was used to prepare three separate sequencing libraries from each subject starting from 2 μl of DNA. The three libraries were then pooled and subjected to exome capture using the SeqCap EZ Human Exome Library v3.0 kit according to standard protocols. Additionally, a fourth library was prepared with a separate index to perform lowpass whole-genome sequencing to assess the karyotypic profile of each subject.

The pool of the three exome captured sequencing libraries for each individual was sequenced on one third of an Illumina Rapid Run flowcell (Hiseq 2500) at the Science for Life Laboratory in Sweden. The low-pass whole genome libraries were spiked in at a concentration of 1% each yielding 2.9 million read-pairs for Subject #2 and 3.2 million read-pairs for Subject #3. Sequencing reads of 101 base pairs each were aligned against the GRCh37 human genome reference using BWA MEM version 0.7.7 (Li, H. Aligning sequence reads, clone sequences and assembly contigs with BWA-MEM. *ArXiv Prepr. ArXiv*13033997 (2013)).

Genotypes and allelic counts were computed across the genome using the Haplotype Caller from the Genome Analysis Toolkit version 3.2-2. Mutations of interest were further filtered out if:
1) excluded from high confidence regions for the Genome in a Bottle genotype calls for NA1287828 (see Genome in a Bottle data hosted by the National Center for Biotechnology Information FTP site: giab/ftp/data/NA12878/variant_calls/NIST/union13callableMQonlymerged_addcert_nouncert_excludesimplerep_excludesegdups_excludedecoy_excludeRepSeqSTRs_noCNVs_v2.18_2mindatasets_5minYesNoRatio.bed.gz)
2) excluded from the strict mask of the 1000 Genomes Project phase 1 (see 1000 Genomes Project data hosted by the European Bioinformatics Institute FTP site:

vol1/ftp/phase1/analysis_results/supporting/accessible_genome_masks/20120824_strict_mask.bed)

3) within low complexity regions (see Github files: 1h3/varcmp/blob/master/scripts/LCRhs37d5.bed.gz)

Analysis of the malignancy from Subject #2 (two months after initial DNA sampling) confirmed the presence of the mutations detected in the earlier DNA sample (including the two CEBPA mutations and two passenger mutations), now at higher allelic fractions (20.5% vs. the earlier 15.5%) and roughly consistent with the 50% blast count in the biopsy. We did not detect any novel clone other than the clone inferred two months before. Malignancies defined by pairs of CEBPA mutations tend to have a favorable prognosis, and indeed this patient enjoyed complete remission following chemotherapy and did not relapse.

Figure 18:
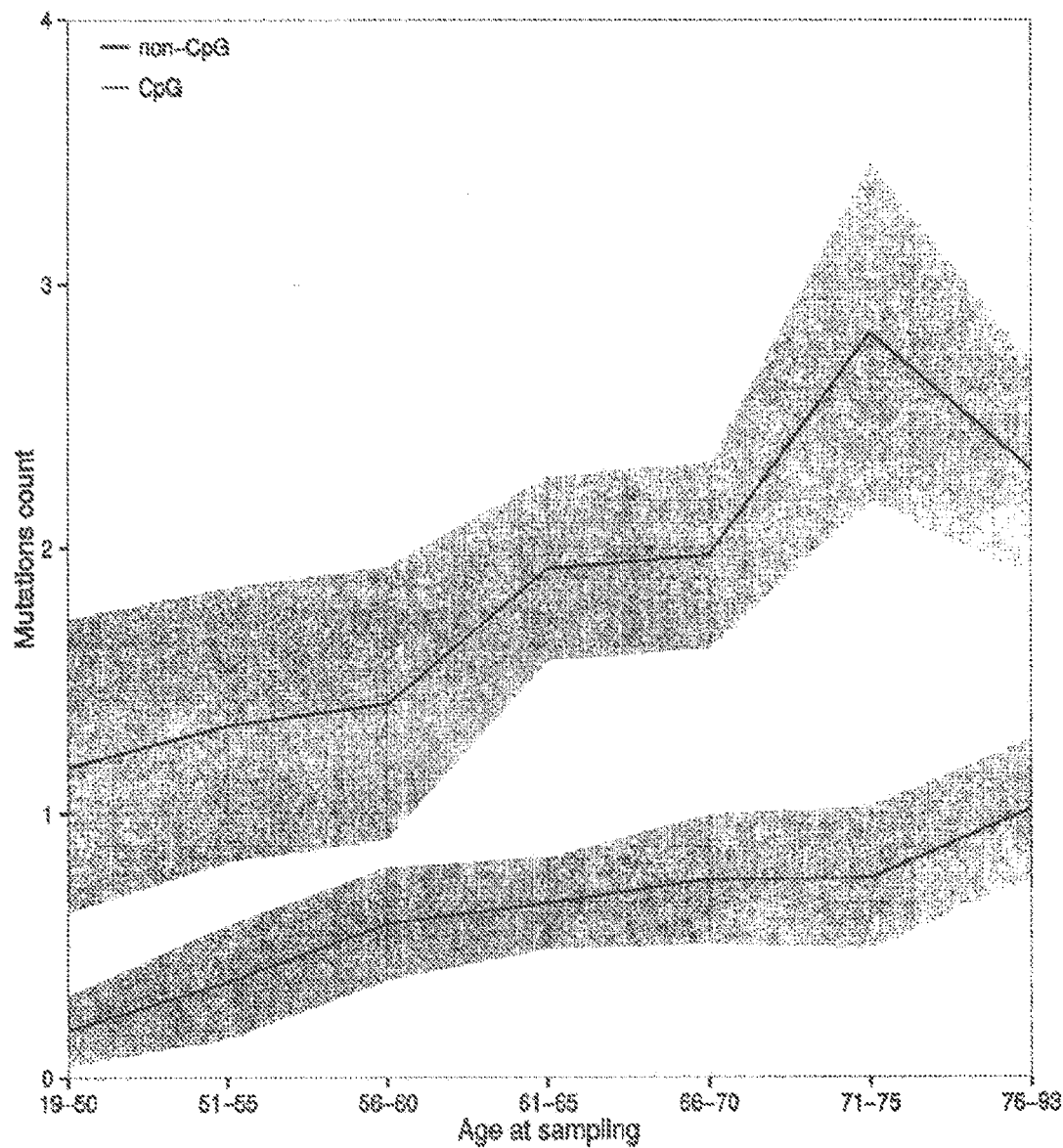
FIG. 18 Average number of putative somatic mutations in subjects with clonal haematopoiesis as a function of age. Numbers were computed separately for non-CpG (in black) and CpG (in red) mutations within 5-year age bins. Numbers were computed for the 455 subjects with detected clonal haematopoeisis for whom age at sampling information was available. Colored bands represent 95% confidence intervals.
Figure 19A:
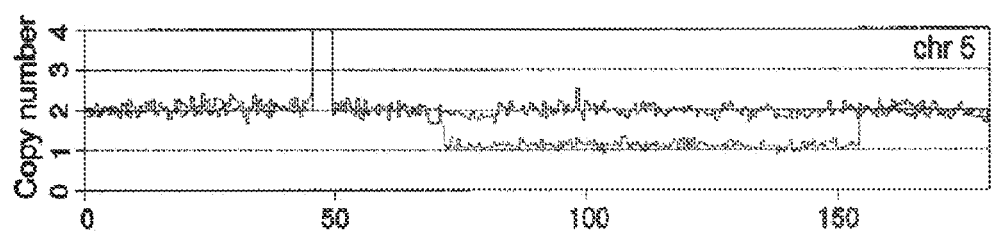
FIG. 19A-19F Copy number variants analysis of low coverage whole-genome sequencing data of bone marrow biopsy of Subject #2, in red, and Subject #3, in blue, at the time of first diagnosis for chromosomes 5, 12, 13, 16, 17, and 19. Copy number estimates near centromeres are overestimated due to misalignment of satellite sequence which is under-represented in the GRCh37 human genome reference. While data for Subject #2 shows a normal karyotype, Subject #3 shows loss of part of chromosome arm 5q, approximately from 5q13 to 5q33, monosomy for chromosome 17, and complex rearrangements involving chromosomes 12, 13, 16, and 19.
Figure 19B:
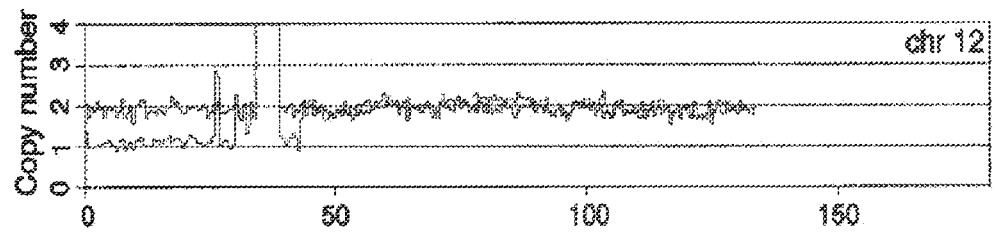
Figure 19C:
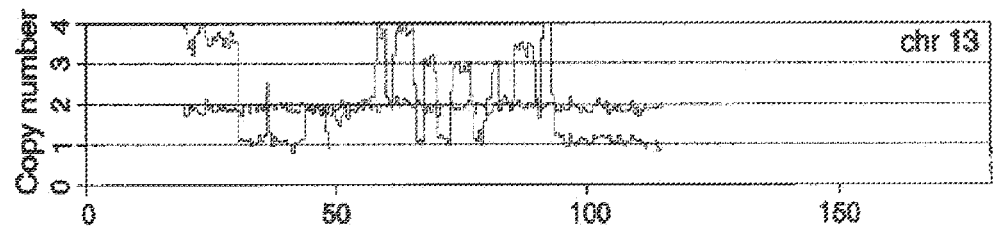
Figure 19D:
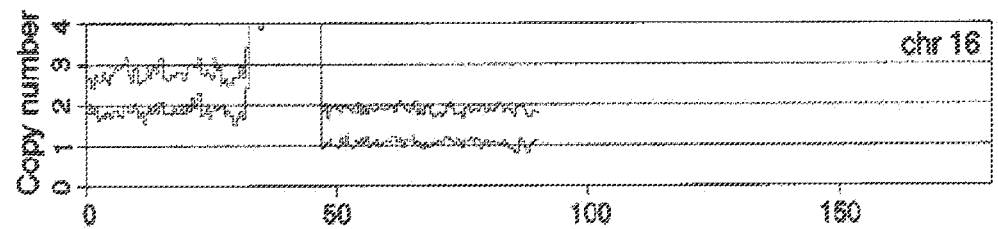
Figure 19E:
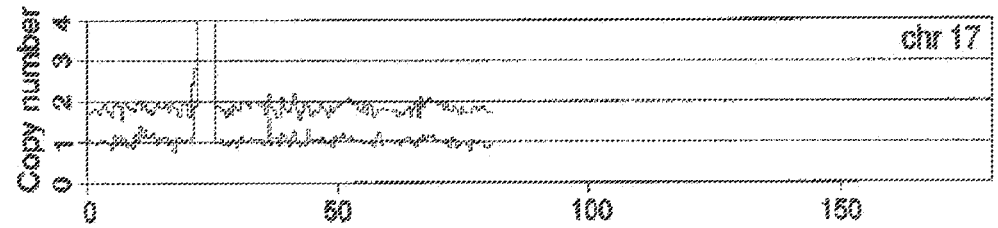
Figure 19F:
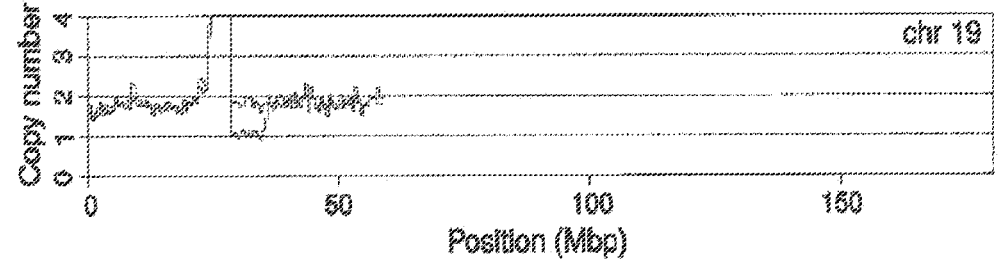

The initial DNA sample from Subject #3 contained a TP53 p.R248Q mutation at an allelic fraction of 24%. At diagnosis, the TP53 mutation had expanded to 86%, consistent with loss of heterozygosity and with the 86% blast cell count in the bone marrow biopsy. Low coverage whole-genome sequence data from the biopsy indicated losses of chromosome 17 and 5q (consisted with karyotype findings), and a complex karyotype pattern of gains and losses on chromosomes 12, 13, 16, and 19 (FIG. 18), alterations that tend to co-occur in subjects with TP53 mutations (Kulasekaraj, A. G. et al. TP53 mutations in myelodysplastic syndrome are strongly correlated with aberrations of chromosome 5, and correlate with adverse prognosis. *Br. J. Haematol.* 160, 660-672 (2013)). By using these segmental losses on six chromosomes (17, 5, 12, 13, 16, and 19) to distinguish between alleles on the lost copy and alleles on the retained copy of each segment, we were able to compare relative copy numbers for the six chromosome-pairs in the initial DNA sample (FIG. 19). This analysis indicated that the losses of 5q and 17 were already present at low allelic fractions (we estimate in 8% and 3% of cells, respectively) in the initial DNA sample, but that the complex karyotype pattern (with losses on the other four chromosomes) was not present or present at undetectable frequency at that time. Since the biopsy shows all these events at high allelic fractions (consistent with the blast count), we conclude that these mutations arose in a series of subclones, with stepwise accumulation of mutations in the following order: TP53 p.R248Q; loss of 5q; loss of chromosome 17 with consequent loss-of-heterozygosity (LOH) for the TP53 mutation; and finally the complex karyotype pattern (FIG. 5C). At least three of these mutations, including the TP53 mutation and LOH, appear to have been present 34 months before diagnosis.

Example 8: Subjects #1-#3

Subject #1

85-years old male, diagnosed with myelodysplastic syndrome 2 months after DNA sampling. Died of unspecified leukemia 15 months after first diagnosis.

Searching for mutations in genes previously observed as significantly mutated in acute myeloid leukemia in high coverage whole-genome sequencing data at the time of DNA sampling revealed recurrent somatic mutations ASXL1 p.G646fsX12 and RUNX1 p.L98fsX24, as well as somatic mutations TET2 p.Y1148fsX5, TET2 p.N1266S, and STAG2 p.E472_splice and further confirmed previously identified somatic mutation SRSF2 p.P95H (Table S9). Mutations in ASXL1 and TET2 were localized in regions of low coverage or no coverage and could not be detected in whole-exome sequencing data. Mutations in RUNX1 and STAG2 were not called in whole-exome sequencing data because observed in, respectively, only three and two sequencing reads. The somatic mutation ASXL1 p.G646fsX12 was at higher allelic fraction than the other candidate drivers, suggesting that this might have been the initiating lesion.

Interestingly, mutations in ASXL1 have been shown to often co-occur in myelodysplastic syndromes with mutations in genes RUNX1 and SRSF2. Copy number analysis of whole-genome sequencing data revealed a normal karyotype.

Subject #2

64-year-old male, diagnosed with acute leukemia 2 months after DNA sampling. Previous history unremarkable, was referred to the haematology unit due to fatigue and pancytopenia. Bone marrow examination showed a hypercellular marrow with 50% blast cells expressing CD34, CD117, CD13 and cytoplasmic MPO, i.e. AML FAB M0. Cytogenetics showed a normal karyotype. Following intense remission induction and consolidation chemotherapy, the patient obtained sustained complete remission. Four years later, he successfully underwent cystectomy due to a low differentiated urothelial cancer in the urinary bladder.

High coverage whole-genome sequencing data at the time of DNA sampling revealed a 33 base pairs somatic insertion CEBPA p.K313_V314ins11 in the basic leucine zipper domain of the protein and previously observed in a different subject. The mutation in CEBPA was not called from whole-exome sequencing data due to the shorter 76 base pairs reads used. Upon further inspection of the data through the Integrative Genomics Viewer37 we also observed a 1 base pair frameshift deletion CEBPA p.P70fsX90 at lower allelic fraction of ~7%, in agreement with the observation that in-frame C-terminal mutations, usually occurring in the basic-leucine zipper (bZIP) domain, are associated with frameshift N-terminal mutations in CEBPA (Barjesteh van Waalwijk van Doorn-Khosrovani, S. et al. Biallelic mutations in the CEBPA gene and low CEBPA expression levels as prognostic markers in intermediate-risk AML. *Hematol. J. Off J. Eur. Haematol. Assoc. EHA* 4, 31-40 (2003)). This mutation was not automatically called by the Haplotype Caller from the Genome Analysis Toolkit due to low allelic counts. Copy number analysis of whole-genome sequencing data both at the time of DNA sampling and at the time of diagnosis confirmed a normal karyotype (FIG. 19).

Whole-exome sequencing data of the bone marrow biopsy further confirmed the presence of the two CEBPA mutations and of three previously identified putative somatic mutations (Table S10). Estimated collective allelic fractions for these three putative somatic mutations increased in frequency between DNA sampling and first diagnosis (15.5% vs. 20.5%; P=0.037, left-tailed Fisher exact test).

Subject #3

75-year-old female, diagnosed with AML 34 months after DNA sampling. SLE with mainly cutaneous manifestations since 15 years which had been treated with steroids but not chemotherapy. Referred to the haematology unit due to pancytopenia, fatigue and pulmonary infection. Bone marrow examination showed a hypercellular marrow with 86% blast cells with no maturation and expressing CD34, CD117, CD13 and cytoplasmic MPO, i.e. AML FAB M0. Cytogenetics showed a complex karyotype including monosomy 17 and 5q-. The patient received palliative treatment with hydroxyurea and died one month later due to the leukemia.

Whole-exome sequencing data at the time of DNA sampling revealed somatic mutation TP53 p.R248Q at an estimated allelic fraction of 24%. Whole-exome sequencing data of the bone marrow biopsy confirmed this somatic mutation at a much higher estimated allelic fraction of 86%. Copy number analysis from low coverage whole-genome sequencing data confirmed that the malignancy was monosomy for chromosome 17,39 had a partial loss of chromosome arm 5q, 40 and a complex karyotype pattern involving chromosomes 12, 13, 16, and 19 (FIG. 19), events that tend to co-occur in myeloid malignancies with TP53 mutations (Kulasekararaj, A. G. et al. TP53 mutations in myelodysplastic syndrome are strongly correlated with aberrations of chromosome 5, and correlate with adverse prognosis. Br. J. Haematol. 160, 660-672 (2013)).

Figure 20:
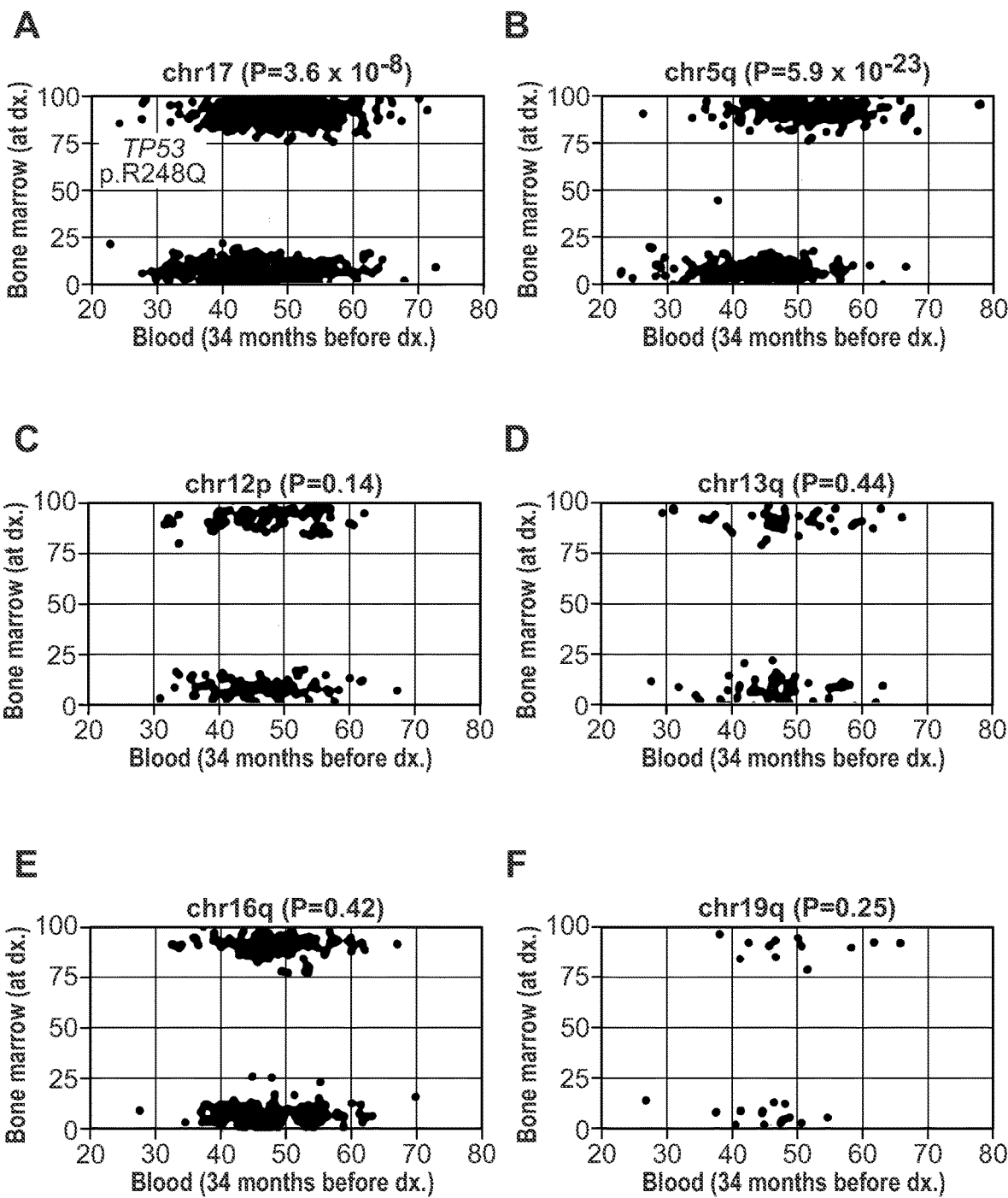
FIG. 20A-20F Allelic fraction analysis of alleles from Subject #3 localized on deleted regions. For each heterozygous allele, allelic fractions from whole-exome sequencing data of blood at DNA sampling and bone marrow biopsy at diagnosis are shown. Heterozygous alleles for which allelic fractions in blood are below 20% are excluded as these are enriched for sequencing or alignment artifacts. Panels A, B, C, D, E, F show heterozygous alleles from deleted regions in chromosomes, respectively, 17, 5, 12, 13, 16, and 19. P-values for comparing allelic fractions in blood between alleles retained (i.e. at more than 50% allelic fraction in bone marrow biopsy) and alleles lost (i.e. at less than 50% allelic fraction in bone marrow biopsy) using a Mann-Whitney test are reported.

To test if these events were already present at the time of DNA sampling, we analyzed allelic fractions for the following six regions deleted in the malignancy:
1) chromosome 17 (FIG. 20A)
2) chromosome arm 5q from Mbp 72 to Mbp 155 (FIG. 20B)
3) chromosome arm 12p up to Mbp 26 (FIG. 20C)
4) chromosome arm 13q from Mbp 91 (FIG. 20D)
5) chromosome arm 16q (FIG. 20E)
6) chromosome arm 19q up to Mbp 35 (FIG. 20F)

For each region we tested if allelic fractions for alleles retained in the malignancy and alleles lost in the malignancy were significantly different at the time of DNA sampling using a Mann-Whitney test. This test resulted significant for chromosome 17 (45.5% vs. 48.3%; P<0.001, FIG. 20B), for the chromosome arm 5q region (43.0% vs. 51.6%; P<0.001, FIG. 20A), but not for each of the remaining regions (FIG. 20C-F). High allelic fractions for these events in the biopsy shows that they needed to co-exist in the same sub-clone, this analysis suggests a most likely sequence of events of first loss of chromosome arm 5q, then loss of chromosome 17, and last the complex karyotype pattern of gains and losses on chromosomes 12, 13, 16, and 19. Therefore, while karyotyping abnormalities for chromosomes 5 and 17 must have already been present at the time of DNA sampling, 34 months before AML diagnosis, abnormalities at chromosomes 12, 13, 16, and 19 either developed later or were at undetectable frequency at the time of DNA sampling.

Statistics and Figures

Cox proportional hazards analyses and Kaplan-Meier plots were performed and generated using the R survival package. Forest plots were generated using the R metafor package.

All remaining figures were generated using the R ggplot2 package and Google Drawings.

Tables

TABLE S1

Mean age and standard deviation of different groups ascertained in the cohort.

| Group | Count | Age |
| --- | --- | --- |
| Total | 12,380 | 55 ± 12 |
| Male | 6,600 | 52 ± 11 |
| Male control | 3,187 | 56 ± 11 |
| Male schizophrenia | 2,964 | 53 ± 11 |
| Male bipolar | 454 | NA |
| Female | 5,780 | 56 ± 12 |
| Female control | 3,063 | 57 ± 12 |
| Female schizophrenia | 2,006 | 55 ± 12 |
| Female bipolar | 711 | NA |

TABLE S2

Mutations observed at least seven times in hematologic and lymphoid cancers in the Catalogue Of Somatic Mutations In Cancer (COSMIC) database v69 (released Jun. 2, 2014) and excluded from analysis in this study. Mutation ASXL1 p.G646fsX12 is a genuine recurrent somatic mutation but due to low coverage at the site of the mutation it was impossible to distinguish true positives from PCR artifacts.

| Variant | Amino acid change | COSMIC ID | Number of observations in hematopoietic and lymphoid cancer | Reason for exclusion |
| --- | --- | --- | --- | --- |
| rs10521 | NOTCH1 p.D1698D | COSM33747 COSM1461158 | 11 | Inherited mutation |
| rs3822214 | KIT p.M541L | COSM28026 | 16 | Inherited mutation |
| rs10663835 | CNDP1 p.L20_E21insL | COSM307404 COSM1683699 | 8 | Inherited mutation |
| rs55980345 | PKD1L2 p.N236fsX26 | COSM314177 COSM314178 COSM1684461 COSM1684462 | 7 | Inherited mutation |
| rs139115934 | ASXL1 p.E1102D | COSM36205 | 15 | Inherited mutation |
| rs146317894 | OR52D1 p.T204fsX33 | COSM1683657 | 7 | Inherited mutation |
| rs147836249 | TET2 p.F868L | COSM87107 | 7 | Inherited mutation |
| NA | ASXL1 p.G646fsX12 | COSM34210 COSM1411076 COSM1658769 | 319 | Potential PCR slippage error due to G homopolymer run |
| NA | ASXL1 p.G645fsX58 | CO5M85923 COSM1180918 | 0 | Potential PCR slippage error due to G homopolymer run |
| NA | NOTCH1 p.V1578delV | COSM13047 | 15 | Potential PCR slippage error due to CAC tandem repeat |

TABLE S3

List of candidate driver somatic mutations detected in the cohort.

| Chromosome | Position (GRCh37) | dbSNP 138 ID | Reference Allele | Alternate Allele | Reference Count | Alternate Count | COSMIC ID | COSMIC Count | Gene | Annotation |
|---|---|---|---|---|---|---|---|---|---|---|
| 2 | 25,457,164 | NA | T | C | 31 | 28 | NA | 0 | DNMT3A | NM_022552:exon23:c.A2723G:p.Y908C |
| 2 | 25,457,164 | NA | T | C | 81 | 19 | NA | 0 | DNMT3A | NM_022552:exon23:c.A2723G:p.Y908C |
| 2 | 25,457,164 | NA | T | C | 94 | 29 | NA | 0 | DNMT3A | NM_022552:exon23:c.A2723G:p.Y908C |
| 2 | 25,457,168 | NA | C | T | 65 | 41 | NA | 0 | DNMT3A | NM_022552:exon23:c.G2719A:p.E907K |
| 2 | 25,457,173 | NA | A | C | 121 | 35 | NA | 0 | DNMT3A | NM_022552:exon23:c.G2714G:p.L905R |
| 2 | 25,457,173 | NA | A | T | 97 | 30 | NA | 0 | DNMT3A | NM_022552:exon23:c.G2714A:p.L905Q |
| 2 | 25,457,176 | rs149095705 | G | A | 55 | 6 | 87007 | 6 | DNMT3A | NM_022552:exon23:c.C2711T:p.P904L |
| 2 | 25,457,176 | rs149095705 | G | A | 65 | 21 | 87007 | 6 | DNMT3A | NM_022552:exon23:c.C2711T:p.P904L |
| 2 | 25,457,176 | rs149095705 | G | A | 81 | 13 | 87007 | 6 | DNMT3A | NM_022552:exon23:c.C2711T:p.P904L |
| 23 | 25,457,176 | rs149095705 | G | A | 88 | 11 | 87007 | 6 | DNMT3A | NM_022552:exon23:c.C2711T:p.P904L |
| 2 | 25,457,192 | NA | G | A | 67 | 40 | NA | 0 | DSMT3A | NM_022552:exon23:c.C2695T:p.R899C |
| 2 | 25,457,204 | NA | C | T | 82 | 23 | 335620 335621 | 0 | DNMT3A | NM_022552:exon23:c.G2683A:p.V895M |
| 2 | 25,457,209 | NA | C | T | 72 | 25 | NA | 0 | DNMT3A | NM_022552:exon23:c.G2678A:p.W893X |
| 2 | 25,457,215 | NA | CG | C | 51 | 12 | NA | 0 | DNMT3A | NM_022552:exon23:c.2671_2672G |
| 2 | 25,457,218 | NA | C | T | 59 | 13 | 1482984 256042 | 1 | DSMT3A | NM_022552:exon23:c.2669A:p.G890D |
| 2 | 25,457,242 | rs147001633 | C | G | 50 | 5 | 3356083 99740 | 14 | DSMT3A | NM_022552:exon23:c.G2645C:p.R882P |
| 2 | 25,457,242 | rs147001633 | C | G | 75 | 9 | 3356083 99740 | 14 | DSMT3A | NM_022552:exon23:c.G2645C:p.R882P |
| 2 | 25,457,242 | rs147001633 | C | T | 27 | 3 | 442676 52944 | 392 | DSMT3A | NM_022552:exon23:c.G2645C:p.R882P |
| 2 | 25,457,242 | rs147001633 | C | T | 30 | 12 | 442676 52944 | 392 | DSMT3A | NM_022552:exon23:c.G2645C:p.R882P |
| 2 | 25,457,242 | rs147001633 | C | T | 44 | 5 | 442676 32944 | 392 | DSMT3A | NM_022552:exon23:c.G2645C:p.R882P |

TABLE S3-continued

List of candidate driver somatic mutations detected in the cohort.

| Chromosome | Position (GRCh37) | dbSNP 138 ID | Reference Allele | Alternate Allele | Reference Count | Alternate Count | COSMIC ID | COSMIC Count | Gene | Annotation |
|---|---|---|---|---|---|---|---|---|---|---|
| 2 | 25,457,242 | rs147001633 | C | T | 45 | 5 | 44267652944 | 392 | DSMT3A | NM_022552:exon23:c.G2645C:p.R882P |
| 2 | 25,457,242 | rs147001633 | C | T | 47 | 7 | 44267652944 | 392 | DSMT3A | NM_022552:exon23:c.G2645C:p.R882P |
| 2 | 25,457,242 | rs147001633 | C | T | 48 | 10 | 44267652944 | 392 | DSMT3A | NM_022552:exon23:c.G2645C:p.R882P |
| 2 | 25,457,242 | rs147001633 | C | T | 48 | 15 | 44267652944 | 392 | DSMT3A | NM_022552:exon23:c.G2645C:p.R882P |
| 2 | 25,457,242 | rs147001633 | C | T | 48 | 7 | 44267652944 | 392 | DSMT3A | NM_022552:exon23:c.G2645C:p.R882P |
| 2 | 25,457,242 | rs147001633 | C | T | 50 | 7 | 44267652944 | 392 | DSMT3A | NM_022552:exon23:c.G2645C:p.R882P |
| 2 | 25,457,242 | rs147001633 | C | T | 51 | 16 | 44267652944 | 392 | DSMT3A | NM_022552:exon23:c.G2645C:p.R882P |
| 2 | 25,457,242 | rs147001633 | C | T | 52 | 6 | 44267652944 | 392 | DSMT3A | NM_022552:exon23:c.G2645C:p.R882P |
| 2 | 25,457,242 | rs147001633 | C | T | 53 | 8 | 44267652944 | 392 | DSMT3A | NM_022552:exon23:c.G2645C:p.R882P |
| 2 | 25,457,242 | rs147001633 | C | T | 56 | 17 | 44267652944 | 392 | DSMT3A | NM_022552:exon23:c.G2645C:p.R882P |
| 2 | 25,457,242 | rs147001633 | C | T | 60 | 10 | 44267652944 | 392 | DSMT3A | NM_022552:exon23:c.G2645C:p.R882P |
| 2 | 25,457,242 | rs147001633 | C | T | 63 | 8 | 44267652944 | 392 | DSMT3A | NM_022552:exon23:c.G2645C:p.R882P |
| 2 | 25,457,243 | rs377577594 | G | A | 29 | 3 | 116570453042 | 164 | DSMT3A | NM_022552:exon23:c.C2644T:p.R882C |
| 2 | 25,457,243 | rs377577594 | G | A | 29 | 8 | 116570453042 | 164 | DSMT3A | NM_022552:exon23:c.C2644T:p.R882C |
| 2 | 25,457,243 | rs377577594 | G | A | 31 | 4 | 116570453042 | 164 | DSMT3A | NM_022552:exon23:c.C2644T:p.R882C |
| 2 | 25,457,243 | rs377577594 | G | A | 59 | 10 | 116570453042 | 164 | DSMT3A | NM_022552:exon23:c.C2644T:p.R882C |

TABLE S3-continued

List of candidate driver somatic mutations detected in the cohort.

| Chromosome | Position (GRCh37) | dbSNP 138 ID | Reference Allele | Altenate Allele | Reference Count | Alternate Count | COSMIC ID | COSMIC Count | Gene | Annotation |
|---|---|---|---|---|---|---|---|---|---|---|
| 2 | 25,457,243 | rs377577594 | G | A | 69 | 8 | 1165704 53042 | 164 | DSMT3A | NM_022552:exon23:c.C2644T:p.R882C |
| 2 | 25,457,243 | rs377577594 | G | A | 77 | 24 | 1165704 53042 | 164 | DSMT3A | NM_022552:exon23:c.C2644T:p.R882C |
| 2 | 25,457,249 | NA | T | C | 58 | 19 | 120499 | 3 | DSMT3A | NM_022552:exon23:c.A2638G:p.M880V |
| 2 | 25,458,595 | rs373014701 | A | G | 38 | 11 | 231568 | 2 | DSMT3A | NM_022552:exon22:c.T2578C:p.W860R |
| 2 | 25,458,595 | rs373014701 | A | G | 43 | 12 | 231568 | 2 | DSMT3A | NM_022552:exon22:c.T2578C:p.W860R |
| 2 | 25,459,595 | rs373014701 | A | G | 50 | 14 | 231568 | 2 | DSMT3A | NM_022552:exon22:c.T2578C:p.W860R |
| 2 | 25,459,595 | rs373014701 | A | G | 86 | 17 | 231568 | 2 | DSMT3A | NM_022552:exon22:c.T2578C:p.W860R |
| 2 | 25,459,595 | rs373014701 | A | G | 87 | 11 | 231568 | 2 | DSMT3A | NM_022552:exon22:c.T2578C:p.W860R |
| 2 | 75,458,619 | NA | T | C | 49 | 23 | NA | 0 | DSMT3A | NM_022552:exon22:c.A2554G:p.M852V |
| 2 | 25,458,646 | NA | C | T | 93 | 20 | NA | 0 | DSMT3A | NM_022552:exon22:c.G2527A:p.G843S |
| 2 | 25,458,696 | NA | T | C | 40 | 16 | NA | 0 | DSMT3A | NM_022552:exon23:c.2479-2A>G |
| 2 | 25,459,804 | NA | C | A | 28 | 6 | NA | 0 | DSMT3A | NM_022552:exon22:c.2478+1G>T |
| 2 | 25,459,837 | NA | G | A | 28 | 7 | 99739 | 1 | DSMT3A | NM_022552:exon21:c.C2446T:pC2446T:p.Q816X |
| 2 | 25,461,998 | NA | C | T | 23 | 5 | NA | 0 | DSMT3A | NM_022552:exon21:c.2408+1G>A |
| 2 | 25,462,020 | NA | C | A | 38 | 12 | NA | 0 | DSMT3A | NM_022552:exon20:c.G2387T:p.G796V |
| 2 | 25,462,024 | NA | A | G | 37 | 10 | NA | 0 | DSMT3A | NM_022552:exon20:c.T2383C:p.W795R |
| 2 | 25,462,032 | NA | C | T | 36 | 7 | 720761 720762 | 4 | DSMT3A | NM_022552:exon20:c.G2375A:p.R792H |
| 2 | 25,462,068 | rs370751539 | A | G | 33 | 7 | 1583121 | 1 | DSMT3A | NM_022552:exon20:c.T2539C:p.I780T |
| 2 | 25,462,077 | NA | G | C | 19 | 13 | NA | 0 | DSMT3A | NM_022552:exon20:c.T2330G:p.P777R |
| 2 | 25,462,085 | NA | C | T | 22 | 11 | NA | 0 | DSMT3A | NM_022552:exon21:c.2323-1G>A |
| 2 | 25,463,174 | NA | GAGAAATCGCCAGAT | G | 152 | 19 | NA | 0 | DSMT3A | NM_022552:exon19:c.2305_2319C |

TABLE S3-continued

List of candidate driver somatic mutations detected in the cohort.

| Chromosome | Position (GRCh37) | dbSNP 138 ID | Reference Allele | Alternate Allele | Reference Count | Alternate Count | COSMIC ID | COSMIC Count | Gene | Annotation |
|---|---|---|---|---|---|---|---|---|---|---|
| 2 | 25,463,182 | NA | G | A | 144 | 23 | 231563 | 4 | DSMT3A | NM_022552:exon19:c.T2311T:p.R771X |
| 2 | 25,463,184 | NA | G | T | 169 | 36 | 1583106 | 1 | DSMT3A | NM_022552:exon19:c.T2309A:p.S770X |
| 2 | 25,463,187 | NA | A | G | 183 | 45 | NA | 0 | DSMT3A | NM_022552:exon19:c.T2306C:p.I769T |
| 2 | 25,463,195 | NA | CTT | C | 61 | 33 | NA | 0 | DSMT3A | NM_022552:exon19:c.2296_2298G |
| 2 | 25,463,212 | NA | T | C | 84 | 89 | NA | 0 | DSMT3A | NM_022552:exon19:c.A2281G:p.M761V |
| 2 | 25,463,225 | NA | C | A | 173 | 42 | NA | 0 | DSMT3A | NM_022552:exon19:c.G2268T:p.E756D |
| 2 | 25,463,229 | NA | A | G | 126 | 20 | NA | 0 | DSMT3A | NM_022552:exon19:c.T2264C:p.F755S |
| 2 | 25,463,229 | NA | A | G | 43 | 16 | NA | 0 | DSMT3A | NM_022552:exon19:c.T2264C:p.F755S |
| 2 | 25,463,234 | NA | C | G | 105 | 30 | NA | 0 | DSMT3A | NM_022552:exon19:c.G2259C:p.W753C |
| 2 | 25,463,241 | NA | A | C | 193 | 31 | NA | 0 | DSMT3A | NM_022552:exon19:c.T2252G:p.F751C |
| 2 | 25,463,248 | NA | G | A | 153 | 47 | 239133 | 4 | DSMT3A | NM_022552:exon19:c.T2245T:p.R749C |
| 2 | 25,463,248 | NA | G | A | 90 | 23 | 219333 | 4 | DSMT3A | NM_022552:exon19:c.T2245T:p.R749C |
| 2 | 25,463,286 | rs139293773 | C | T | 137 | 25 | 1318940 133737 | 6 | DSMT3A | NM_022552:exon19:c.G2207A:p.R736H |
| 2 | 25,463,286 | rs139293773 | C | T | 44 | 36 | 1318940 133737 | 6 | DSMT3A | NM_022552:exon19:c.G2207A:p.R736H |
| 2 | 25,463,286 | rs139293773 | C | T | 55 | 32 | 1318940 133737 | 6 | DSMT3A | NM_022552:exon19:c.G2207A:p.R736H |
| 2 | 25,463,286 | rs139293773 | C | T | 84 | 12 | 1318940 133737 | 6 | DSMT3A | NM_022552:exon19:c.G2207A:p.R736H |
| 2 | 25,463,287 | NA | G | A | 71 | 18 | 231560 | 5 | DSMT3A | NM_022552:exon19:c.C2206T:p.R736C |
| 2 | 25,463,289 | rs147828672 | T | C | 100 | 25 | 133126 | 4 | DSMT3A | NM_022552:exon19:c.A2204G:p.Y735C |
| 2 | 25,463,289 | rs147828672 | T | C | 76 | 21 | 133126 | 4 | DSMT3A | NM_022552:exon19:c.A2204G:p.Y735C |
| 2 | 25,463,289 | rs147828672 | T | C | 84 | 13 | 133126 | 4 | DSMT3A | NM_022552:exon19:c.A2204G:p.Y735C |
| 2 | 25,463,289 | rs147829872 | T | C | 90 | 13 | 133126 | 4 | DSMT3A | NM_022552:exon19:c.A2204G:p.Y735C |
| 2 | 25,463,295 | NA | T | C | 66 | 10 | NA | 0 | DSMT3A | NM_022552:exon19:c.A2198G:p.E733G |

TABLE S3-continued

List of candidate driver somatic mutations detected in the cohort.

| Chromosome | Position (GRCh37) | dbSNP 138 ID | Reference Allele | Altenate Allele | Reference Count | Alternate Count | COSMIC ID | COSMIC Count | Gene | Annotation |
|---|---|---|---|---|---|---|---|---|---|---|
| 2 | 23,463,296 | NA | CAA | C | 79 | 20 | NA | 0 | DSMT3A | NM_022552:exon19:c.2195_2197G |
| 2 | 25,463,296 | NA | C | CA | 23 | 3 | NA | 0 | DSMT3A | NM_022552:exon19:c.2197_2197delinsTG |
| 2 | 25,463,296 | NA | C | CA | 48 | 19 | NA | 0 | DSMT3A | NM_022552:exon19:c.2197_2197delinsTG |
| 2 | 25,463,297 | NA | AAAG | A | 107 | 26 | 1583117 99742 | 8 | DSMT3A | NM_022552:exon19:c.2193_2196T |
| 2 | 25,463,297 | NA | AAAG | A | 138 | 35 | 1593117 99742 | 8 | DSMT3A | NM_022552:exon19:c.2193_2196T |
| 2 | 25,463,297 | NA | AAAG | A | 77 | 20 | 1583117 99742 | 8 | DSMT3A | NM_022552:exon19:c.2193_2196T |
| 2 | 25,463,297 | NA | AAAG | A | 92 | 22 | 1583117 99742 | 8 | DSMT3A | NM_022552:exon19:c.2193_2196T |
| 2 | 25,463,298 | NA | A | C | 101 | 18 | NA | 0 | DSMT3A | NM_022552:exon19:c.T2195G:p.F732C |
| 2 | 25,463,308 | rs200018028 | G | A | 58 | 70 | 1318937 249142 | 4 | DSMT3A | NM_022552:exon19:c.C2185T:p.R729W |
| 2 | 25,463,308 | rs200018028 | G | A | 61 | 22 | 1338937 249142 | 4 | DSMT3A | NM_022552:exon19:c.C2185T:p.R729W |
| 2 | 25,463,541 | rs367909007 | G | C | 124 | 21 | 442677 87011 | 11 | DSMT3A | NM_022552:exon18:c.C2141G:p.S714C |
| 2 | 25,463,541 | rs367909007 | G | C | 164 | 29 | 442677 87011 | 11 | DSMT3A | NM_022552:exon18:c.C2141G:p.S714C |
| 2 | 25,463,541 | rs367909007 | G | C | 172 | 28 | 442677 87011 | 11 | DSMT3A | NM_022552:exon18:c.C2141G:p.S714C |
| 2 | 25,463,554 | NA | A | T | 79 | 16 | 249803 | 1 | DSMT3A | NM_022552:exon18:c.T2128A:p.C710S |
| 2 | 25,463,565 | NA | C | T | 117 | 31 | NA | 0 | DSMT3A | NM_022552:exon18:c.G2117A:p.G706E |
| 2 | 25,463,566 | NA | CA | C | 62 | 9 | NA | 0 | DSMT3A | NM_022552:exon18:c.2115_2116G |
| 2 | 25,463,574 | NA | AG | A | 71 | 24 | NA | 0 | DSMT3A | NM_022552:exon18:c.2107_2108T |
| 2 | 25,463,578 | NA | C | T | 117 | 18 | NA | 0 | DSMT3A | NM_022552:exon18:c.G2104A:p.D702N |
| 2 | 25,463,593 | NA | C | A | 38 | 24 | NA | 0 | DSMT3A | NM_022552:exon18:c.G2089T:p.E697X |
| 2 | 25,463,595 | NA | TG | T | 137 | 18 | 1583101 | 1 | DSMT3A | NM_022552:exon18:c.2086_2087A |

TABLE S3-continued

List of candidate driver somatic mutations detected in the cohort.

| Chromosome | Position (GRCh37) | dbSNP 138 ID | Reference Allele | Altenate Allele | Reference Count | Alternate Count | COSMIC ID | COSMIC Count | Gene | Annotation |
|---|---|---|---|---|---|---|---|---|---|---|
| 2 | 25,464,430 | NA | C | T | 33 | 13 | NA | 0 | DSMT3A | NM_022552:exon18:c.2082+1G>A |
| 2 | 25,464,430 | NA | C | T | 46 | 9 | NA | 0 | DSMT3A | NM_022552:exon18:c.2082+1G>A |
| 2 | 25,464,430 | NA | C | T | 51 | 8 | NA | 0 | DSMT3A | NM_022552:exon18:c.2082+1G>A |
| 2 | 25,464,450 | rs369713081 | C | T | 42 | 5 | NA | 0 | DSMT3A | NM_022552:exon17:c.G2063A:p.R688H |
| 2 | 25,464,450 | rs369713081 | C | T | 43 | 35 | NA | 0 | DSMT3A | NM_022552:exon17:c.G2063A:p.R688H |
| 2 | 25,464,459 | NA | C | T | 29 | 7 | 1690275 1690276 | 0 | DSMT3A | NM_022552:exon17:c.C2054A:p.G685E |
| 2 | 25,464,470 | NA | GA | G | 38 | 7 | NA | 0 | DSMT3A | NM_022552:exon17:c.2042_2043C |
| 2 | 25,464,470 | NA | G | C | 58 | 11 | NA | 0 | DSMT3A | NM_022552:exon17:c.C2043G:p.I681M |
| 2 | 25,464,471 | NA | A | T | 43 | 8 | NA | 0 | DSMT3A | NM_022552:exon17:c.T2042A:p.I681N |
| 2 | 25,464,486 | NA | C | A | 35 | 24 | NA | 0 | DSMT3A | NM_022552:exon17:c.G2027T:p.R676L |
| 2 | 25,464,507 | NA | GAGTCCT | G | 40 | 7 | NA | 0 | DSMT3A | NM_022552:exon17:c.2000_2006C |
| 2 | 25,464,520 | NA | C | A | 41 | 21 | NA | 0 | DSMT3A | NM_022552:exon17:c.G1993T:p.V665L |
| 2 | 25,464,529 | NA | C | T | 42 | 23 | NA | 0 | DSMT3A | NM_022552:exon17:c.G1984A:p.A662T |
| 2 | 25,464,544 | rs368961181 | C | T | 17 | 5 | NA | 0 | DSMT3A | NM_022552:exon17:c.G1969A:p.V657M |
| 2 | 25,464,544 | rs368961181 | C | T | 33 | 11 | NA | 0 | DSMT3A | NM_022552:exon17:c.G1969A:p.V657M |
| 2 | 25,464,544 | rs368961181 | C | T | 34 | 10 | NA | 0 | DSMT3A | NM_022552:exon17:c.G1969A:p.V657M |
| 2 | 25,464,549 | NA | A | T | 28 | 7 | 133136 | 1 | DSMT3A | NM_022552:exon17:c.T1964A:p.I655N |
| 3 | 25,467,023 | NA | C | A | 58 | 9 | NA | 0 | DSMT3A | NM_022552:exon16:c.C1851+1G>T |
| 2 | 25,467,029 | NA | C | A | 89 | 15 | NA | 0 | DSMT3A | NM_022552:exon15:c.G1846T:p.E616X |
| 2 | 25,467,034 | NA | TC | T | 81 | 28 | NA | 0 | DSMT3A | NM_022552:exon15:c.1840_1841A |
| 2 | 25,467,038 | NA | G | C | 44 | 21 | NA | 0 | DSMT3A | NM_022552:exon15:c.C1837G:p.H613D |
| 2 | 25,467,061 | NA | A | G | 62 | 22 | NA | 0 | DSMT3A | NM_022552:exon15:c.T1814C:p.L605P |
| 2 | 25,467,064 | NA | C | T | 40 | 25 | NA | 0 | DSMT3A | NM_022552:exon15:c.G1811A:p.R604Q |

TABLE S3-continued

List of candidate driver somatic mutations detected in the cohort.

| Chromosome | Position (GRCh37) | dbSNP 138 ID | Reference Allele | Alternate Allele | Reference Count | Alternate Count | COSMIC ID | COSMIC Count | Gene | Annotation |
|---|---|---|---|---|---|---|---|---|---|---|
| 2 | 25,467,078 | NA | C | A | 30 | 19 | NA | 0 | DSMT3A | NM_022552:exon15:c.G1797T:p.E599D |
| 2 | 25,467,078 | NA | C | A | 39 | 23 | NA | 0 | DSMT3A | NM_022552:exon15:c.G1797T:p.E599D |
| 2 | 25,467,078 | NA | C | A | 58 | 42 | NA | 0 | DSMT3A | NM_022552:exon15:c.G1797T:p.E599D |
| 2 | 25,467,078 | NA | C | A | 63 | 54 | NA | 0 | DSMT3A | NM_022552:exon15:c.G1797T:p.E599D |
| 2 | 25,467,083 | NA | G | A | 49 | 18 | 133736 | 4 | DSMT3A | NM_022552:exon15:c.G1792T:p.R598X |
| 2 | 25,467,086 | NA | G | A | 39 | 34 | NA | 0 | DSMT3A | NM_022552:exon15:c.G1789T:p.R597W |
| 3 | 25,467,133 | NA | CAGGGGT | C | 34 | 5 | NA | 0 | DSMT3A | NM_022552:exon15:c1736_1742G |
| 2 | 25,467,136 | NA | G | C | 7 | 14 | NA | 0 | DSMT3A | NM_022552:exon15:c.C1739G:p.R580R |
| 2 | 23,467,169 | NA | G | A | 13 | 14 | NA | 0 | DSMT3A | NM_022552:exon15:c.C1706T:p.P569L |
| 2 | 25,467,410 | NA | T | C | 53 | 33 | NA | 0 | DSMT3A | NM_022552:exon14:c.A1666G:p.R556G |
| 2 | 25,467,428 | NA | C | T | 67 | 12 | 256035 | 4 | DSMT3A | NM_022552:exon14:c.G1648A:p.G550R |
| 2 | 25,467,449 | NA | C | A | 53 | 8 | 87002 | 10 | DSMT3A | NM_022552:exon14:c.G1627T:p.G543C |
| 2 | 25,467,481 | NA | CCGT | C | 37 | 13 | 1583078 | 1 | DSMT3A | NM_022552:exon14:c.1592_1595G |
| 2 | 23,467,490 | NA | T | A | 69 | 17 | NA | 0 | DSMT3A | NM_022552:exon14:c.A1586T:p.D529V |
| 2 | 25,467,516 | NA | G | T | 67 | 12 | NA | 0 | DSMT3A | NM_022552:exon14:c.C1560A:p.C520X |
| 2 | 25,468,120 | NA | A | C | 60 | 20 | NA | 0 | DSMT3A | NM_022552:exon14:c.1554+2T>G |
| 2 | 25,468,121 | NA | C | T | 103 | 12 | NA | 0 | DSMT3A | NM_022552:exon14:c.1554+1G>A |
| 2 | 25,468,121 | NA | C | T | 63 | 10 | NA | 0 | DSMT3A | NM_022552:exon14:c.1554+1G>A |
| 2 | 25,468,138 | NA | A | AT | 46 | 11 | NA | 0 | DSMT3A | NM_022552:exon13:c.1538_1538delinsAT |
| 2 | 25,468,174 | rs149738328 | T | C | 37 | 32 | 231571 | 3 | DSMT3A | NM_022552:exon13:c.A1502G:p.N501S |
| 2 | 25,468,174 | rs149738328 | T | C | 50 | 32 | 231571 | 3 | DSMT3A | NM_022552:exon13:c.A1502G:p.N501S |
| 2 | 25,468,186 | NA | C | T | 23 | 7 | 1318925 1318926 | 3 | DSMT3A | NM_022552:exon13:c.G1490A:p.C497Y |
| 2 | 25,468,888 | NA | C | T | 105 | 43 | NA | 0 | DSMT3A | NM_022552:exon13:c.1474+1G>A |
| 2 | 25,468,912 | NA | C | T | 65 | 1 | NA | 0 | DSMT3A | NM_022552:exon12:c.G1451A:p.R484Q |

TABLE S3-continued

List of candidate driver somatic mutations detected in the cohort.

| Chromosome | Position (GRCh37) | dbSNP 138 ID | Reference Allele | Alternate Allele | Reference Count | Alternate Count | COSMIC ID | COSMIC Count | Gene | Annotation |
|---|---|---|---|---|---|---|---|---|---|---|
| 2 | 25,468,922 | NA | A | C | 55 | 3 | NA | 0 | DSMT3A | NM_022552:exon12:c.T1441G:p.Y481D |
| 2 | 25,469,053 | NA | C | A | 125 | 28 | NA | 0 | DSMT3A | NM_022552:exon11:c.G1405T:p.E469X |
| 2 | 25,469,060 | NA | CT | C | 133 | 25 | NA | 0 | DSMT3A | NM_022552:exon11:c.1397_1398G |
| 2 | 25,469,080 | NA | T | C | 106 | 90 | NA | 0 | DSMT3A | NM_022552:exon11:c.A1378G:p.S460G |
| 2 | 23,469,100 | NA | G | A | 104 | 89 | NA | 0 | DSMT3A | NM_022552:exon11:c.C1358T:p.P453L |
| 2 | 23,469,100 | NA | G | A | 77 | 99 | NA | 0 | DSMT3A | NM_022552:exon11:c.C1358T:p.P453L |
| 2 | 25,469,139 | NA | C | T | 179 | 38 | NA | 0 | DSMT3A | NM_022552:exon11:c.G1319A:p.W440X |
| 2 | 25,469,142 | NA | A | G | 153 | 102 | NA | 0 | DSMT3A | NM_022552:exon11:c.T1316C:p.M439T |
| 2 | 25,469,142 | NA | A | G | 80 | 66 | NA | 0 | DSMT3A | NM_022552:exon11:c.T1316C:p.M439T |
| 2 | 25,469,174 | NA | CT | C | 167 | 24 | NA | 0 | DSMT3A | NM_022552:exon11:c.1283_1284G |
| 2 | 25,469,501 | NA | C | G | 52 | 70 | NA | 0 | DSMT3A | NM_022552:exon10:c.G1267C:p.E423Q |
| 2 | 25,469,614 | NA | G | A | 109 | 73 | NA | 0 | DSMT3A | NM_022552:exon10:c.C1154T:p.P385L |
| 2 | 25,469,614 | NA | G | A | 61 | 39 | NA | 0 | DSMT3A | NM_022552:exon10:c.C1154T:p.P385L |
| 2 | 25,469,614 | NA | G | A | 97 | 62 | NA | 0 | DSMT3A | NM_022552:exon10:c.C1154T:p.P385L |
| 2 | 25,469,633 | NA | G | A | 83 | 14 | NA | 0 | DSMT3A | NM_022552:exon10:c.C1135T:p.R379C |
| 2 | 25,469,647 | NA | T | G | 149 | 18 | NA | 0 | DSMT3A | NM_022552:exon11:c.1123-2A>C |
| 2 | 25,469,927 | NA | A | G | 23 | 14 | NA | 0 | DSMT3A | NM_022552:exon9:c.T1115C:p.V372A |
| 2 | 25,469,928 | rs371677904 | C | T | 21 | 20 | NA | 0 | DSMT3A | NM_022552:exon9:c.G1114A:p.V372I |
| 2 | 25,469,951 | NA | A | G | 30 | 17 | NA | 0 | DSMT3A | NM_022552:exon9:c.T1091C:p.M364T |
| 2 | 25,464,987 | rs139053291 | C | T | 24 | 11 | 133129 | 1 | DSMT3A | NM_022552:exon9:c.G1055A:p.S352N |
| 2 | 25,469,988 | NA | TGC | TT | 53 | 9 | NA | 0 | DSMT3A | NM_022552:exon9:c.1052_1054AA |
| 2 | 25,470,011 | NA | A | G | 17 | 6 | NA | 0 | DSMT3A | NM_022552:exon9:c.T1031C:p.L344P |
| 2 | 25,470,019 | NA | A | AAC | 23 | 9 | NA | 0 | DSMT3A | NM_022552:exon9:c.1023_1023delinsGTT |
| 2 | 25,470,028 | NA | CT | C | 21 | 6 | NA | 0 | DSMT3A | NM_022552:exon10:c.1015_splice |

TABLE S3-continued

List of candidate driver somatic mutations detected in the cohort.

| Chromosome | Position (GRCh37) | dbSNP 138 ID | Reference Allele | Alternate Allele | Reference Count | Alternate Count | COSMIC ID | COSMIC Count | Gene | Annotation |
|---|---|---|---|---|---|---|---|---|---|---|
| 2 | 25,470,479 | NA | C | T | 147 | 30 | 477212 | 0 | DSMT3A | NM_022552:exon8:c.G995A:p.G332E |
| 2 | 25,470,480 | NA | C | T | 102 | 48 | NA | 0 | DSMT3A | NM_022552:exon8:c.G994A:p.G332R |
| 2 | 25,470,484 | NA | C | T | 150 | 21 | 249799 | 1 | DSMT3A | NM_022552:exon8:c.G990A:p.W330X |
| 2 | 25,470,484 | NA | C | T | 72 | 11 | 249799 | 1 | DSMT3A | NM_022552:exon8:c.G990A:p.W330X |
| 2 | 25,470,498 | NA | G | A | 90 | 17 | NA | 0 | DSMT3A | NM_022552:exon8:c.C976T:p.R326C |
| 2 | 25,470,516 | NA | G | A | 108 | 17 | 1318922 133721 133724 | 4 | DSMT3A | NM_022552:exon8:c.C958T:p.R320X |
| 2 | 25,470,516 | NA | G | A | 98 | 16 | 1318922 133721 133724 | 4 | DSMT3A | NM_022552:exon8:c.C958T:p.R320X |
| 2 | 25,470,532 | NA | C | T | 83 | 30 | NA | 0 | DSMT3A | NM_022552:exon8:c.G942A:p.W314X |
| 2 | 25,470,554 | NA | G | A | 77 | 16 | NA | 0 | DSMT3A | NM_022552:exon8:c.C920T:p.P307L |
| 2 | 25,470,554 | NA | G | C | 51 | 6 | 221579 | 1 | DSMT3A | NM_022552:exon8:c.C920G:p.P307R |
| 2 | 25,470,554 | NA | G | C | 86 | 18 | 221579 | 1 | DSMT3A | NM_022552:exon8:c.C920G:p.P307R |
| 2 | 25,470,556 | NA | C | T | 60 | 10 | NA | 0 | DSMT3A | NM_022552:exon8:c.G918A:p.W306X |
| 2 | 25,470,588 | NA | C | T | 60 | 13 | NA | 0 | DSMT3A | NM_022552:exon8:c.G886A:p.V296M |
| 2 | 25,470,588 | NA | C | T | 83 | 15 | NA | 0 | DSMT3A | NM_022552:exon8:c.G886A:p.V296M |
| 2 | 25,470,588 | NA | C | T | 86 | 18 | NA | 0 | DSMT3A | NM_022552:exon8:c.G886A:p.V296M |
| 2 | 25,470,591 | NA | G | C | 48 | 10 | NA | 0 | DSMT3A | NM_022552:exon8:c.C883G:p.L295V |
| 2 | 25,470,599 | NA | A | G | 70 | 19 | NA | 0 | DSMT3A | NM_022552:exon8:c.T875C:p.I292T |
| 2 | 25,470,599 | NA | A | G | 99 | 17 | NA | 0 | DSMT3A | NM_022552:exon8:c.T875C:p.I292T |
| 2 | 25,471,024 | NA | G | GC | 71 | 18 | NA | 0 | DSMT3A | NM_022552:exon7:c.737_737delinsGC |
| 2 | 25,471,064 | NA | GC | G | 58 | 22 | NA | 0 | DSMT3A | NM_022552:exon7:c.696_697C |
| 2 | 198,266,834 | NA | T | C | 148 | 16 | 84677 | 230 | SFB31 | NM_12433:exon15:c.A2098G:p.K700E |
| 2 | 198,266,834 | NA | T | C | 50 | 12 | 84677 | 230 | SFB31 | NM_12433:exon15:c.A2098G:p.K700E |

TABLE S3-continued

List of candidate driver somatic mutations detected in the cohort.

| Chromosome | Position (GRCh37) | dbSNP 138 ID | Reference Allele | Altenate Allele | Reference Count | Alternate Count | COSMIC ID | COSMIC Count | Gene | Annotation |
|---|---|---|---|---|---|---|---|---|---|---|
| 2 | 198,266,834 | NA | T | C | 50 | 16 | 84677 | 230 | SFB31 | NM_12433:exon15:c.A2098G:p.K700E |
| 2 | 198,266,834 | NA | T | C | 53 | 6 | 84677 | 230 | SFB31 | NM_12433:exon15:c.A2098G:p.K700E |
| 2 | 198,266,834 | NA | T | C | 60 | 17 | 84677 | 230 | SFB31 | NM_12433:exon15:c.A2098G:p.K700E |
| 2 | 198,266,834 | NA | T | C | 66 | 10 | 84677 | 230 | SFB31 | NM_12433:exon15:c.A2098G:p.K700E |
| 2 | 198,266,834 | NA | T | C | 79 | 14 | 84677 | 230 | SFB31 | NM_12433:exon15:c.A2098G:p.K700E |
| 2 | 198,266,834 | NA | T | C | 91 | 8 | 84677 | 230 | SFB31 | NM_12433:exon15:c.A2098G:p.K700E |
| 2 | 198,266,834 | NA | T | C | 97 | 11 | 84677 | 230 | SFB31 | NM_12433:exon15:c.A2098G:p.K700E |
| 2 | 198,267,359 | rs377023736 | C | A | 207 | 27 | 131557 | 13 | SFB31 | NM_12433:exon14:c.G1998T:p.K666N |
| 2 | 198,267,359 | rs377023736 | C | G | 66 | 22 | 132937 | 9 | SFB31 | NM_12433:exon14:c.G1998T:p.K666N |
| 2 | 198,267,360 | NA | T | G | 61 | 11 | 131556 | 8 | SFB31 | NM_12433:exon14:c.A1997C:p.K666T |
| 2 | 197,267,491 | NA | C | G | 106 | 15 | 132938 | 7 | SFB31 | NM_12433:exon14:c.G1866C:p.E622D |
| 3 | 38,182,641 | rs387907272 | T | C | 91 | 21 | 85990 | 1027 | MYD38 | NM_002468:exon5:c.7941T>C:p.L265P |
| 4 | 106,155,544 | NA | G | T | 29 | 14 | 3428018 3428019 | 0 | TET2 | NM_017628:exon3:p.E149X |
| 4 | 106,155,915 | NA | GC | G | 24 | 12 | NA | 0 | TET2 | NM_017628:exon3:c.816_817G |
| 4 | 106,156,079 | NA | C | G | 97 | 18 | NA | 0 | TET2 | NM_017628:exon3:c.C980G:p.S327X |
| 4 | 106,156,409 | NA | A | AC | 73 | 12 | NA | 0 | TET2 | NM_017628:exon3:c.1310_1310delinsAC |
| 4 | 106,156,441 | NA | G | T | 38 | 9 | NA | 0 | TET2 | NM_017628:exon3:c.G1342T:p.E448X |
| 4 | 106,156,564 | NA | GA | G | 106 | 23 | NA | 0 | TET2 | NM_017628:exon3:c.1465_1466G |
| 4 | 106,156,623 | NA | GT | G | 50 | 11 | NA | 0 | TET2 | NM_017628:exon3:c.1524_1525G |
| 4 | 106,156,747 | NA | C | T | 119 | 13 | 1318629 41644 | 26 | TET2 | NM_017628:exon3:c.C1678T:p.R550X |
| 4 | 106,156,758 | NA | G | GC | 152 | 31 | 43490 | 3 | TET2 | NM_017628:exon3:c.1659_1659delinsGC |
| 4 | 106,157,162 | NA | A | AT | 105 | 16 | NA | 0 | TET2 | NM_017628:exon3:c.2063_20639delinsAT |
| 4 | 106,157,332 | NA | CAG | C | 39 | 28 | NA | 0 | TET2 | NM_017628:exon3:c.2233_2235C |

TABLE S3-continued

List of candidate driver somatic mutations detected in the cohort.

| Chromosome | Position (GRCh37) | dbSNP 138 ID | Reference Allele | Altenate Allele | Reference Count | Alternate Count | COSMIC ID | COSMIC Count | Gene | Annotation |
|---|---|---|---|---|---|---|---|---|---|---|
| 4 | 106,157,335 | NA | C | T | 53 | 10 | 87099 | 1 | TET2 | NM_017628:exon3:c.C2236T:p.Q746X |
| 4 | 106,157,367 | NA | AC | A | 75 | 39 | NA | 0 | TET2 | NM_017628:exon3:c.2268_2269A |
| 4 | 106,157,467 | NA | C | T | 53 | 10 | 43416 | 1 | TET2 | NM_017628:exon3:c.C2368T:p.Q790X |
| 4 | 106,157,503 | NA | GT | G | 66 | 14 | NA | 0 | TET2 | NM_017628:exon3:c.2404_2405G |
| 4 | 106,157,525 | NA | TA | T | 68 | 11 | NA | 0 | TET2 | NM_017628:exon3:c.2426_2477T |
| 4 | 106,157,542 | NA | A | T | 55 | 22 | NA | 0 | TET2 | NM_017628:exon3:c.A2443T:p.R815X |
| 4 | 106,157,608 | NA | AAT | A | 53 | 20 | NA | 0 | TET2 | NM_017628:exon3:c.2509_2511A |
| 4 | 106,157,638 | NA | C | T | 38 | 8 | NA | 0 | TET2 | NM_017628:exon3:c.C2539T:p.Q847X |
| 4 | 106,157,761 | NA | C | T | 54 | 11 | NA | 0 | TET2 | NM_017628:exon3:c.C2662T:p.Q888X |
| 4 | 106,157,842 | NA | G | GCT | 31 | 10 | NA | 0 | TET2 | NM_017628:exon3:c.2743_2743delinsGCT |
| 4 | 106,158,224 | NA | AC | A | 97 | 19 | NA | 0 | TET2 | NM_017628:exon3:c.3125_3126A |
| 4 | 106,158,349 | NA | CA | C | 77 | 12 | NA | 0 | TET2 | NM_017628:exon3:c.3250_3251C |
| 4 | 106,158,359 | NA | CTT | C | 42 | 10 | NA | 0 | TET2 | NM_017628:exon3:c.3260_3262C |
| 4 | 106,158,378 | NA | C | CA | 18 | 3 | NA | 0 | TET2 | NM_017628:exon3:c.3279_3279delinsCA |
| 4 | 106,158,378 | NA | C | CA | 40 | 9 | NA | 0 | TET2 | NM_017628:exon3:c.3279_3279delinsCA |
| 4 | 106,158,442 | NA | C | CT | 55 | 17 | NA | 0 | TET2 | NM_017628:exon3:c.3343_3343delinsCT |
| 4 | 106,158,485 | NA | AT | A | 69 | 22 | NA | 0 | TET2 | NM_017628:exon3:c.3386_3387A |
| 4 | 106,159,509 | NA | G | A | 75 | 24 | 87117 | 1 | TET2 | NM_001127208:exon3:c.3409+1G>2A |
| 4 | 106,158,579 | NA | A | AT | 32 | 23 | NA | 0 | TET2 | NM_017628:exon3:c.3480_3480delinsAT |
| 4 | 106,158,595 | NA | T | A | 54 | 22 | NA | 0 | TET2 | NM_017628:exon3:c.T3496A:p.X1166K |
| 9 | 5,073,770 | rs386626619 | G | T | 101 | 20 | 12600 | 30,687 | JAK2 | NM_004972:exon14:c.G1849T:p.V617F |
| 9 | 5,073,770 | rs386626619 | G | T | 115 | 14 | 12600 | 30,637 | JAK2 | NM_004972:exon14:c.G1849T:p.V617F |
| 9 | 5,073,770 | rs386626619 | G | T | 117 | 18 | 12600 | 30,687 | JAK2 | NM_004972:exon14:c.G1849T:p.V617F |
| 9 | 5,073,170 | rs386626619 | G | T | 125 | 11 | 12600 | 30,687 | JAK2 | NM_004972:exon14:c.G1849T:p.V617F |

TABLE S3-continued

List of candidate driver somatic mutations detected in the cohort.

| Chromosome | Position (GRCh37) | dbSNP 138 ID | Reference Allele | Alternate Allele | Reference Count | Alternate Count | COSMIC ID | COSMIC Count | Gene | Annotation |
|---|---|---|---|---|---|---|---|---|---|---|
| 9 | 5,073,170 | rs386626619 | G | T | 126 | 14 | 12600 | 30,687 | JAK2 | NM_004972:exon14:c.G1849T:p.V617F |
| 9 | 5,073,170 | rs386626619 | G | T | 126 | 21 | 12600 | 30,687 | JAK2 | NM_004972:exon14:c.G1849T:p.V617F |
| 9 | 5,073,170 | rs386626619 | G | T | 175 | 16 | 12600 | 30,687 | JAK2 | NM_004972:exon14:c.G1849T:p.V617F |
| 9 | 5,073,170 | rs386626619 | G | T | 31 | 59 | 12600 | 30,687 | JAK2 | NM_004972:exon14:c.G1849T:p.V617F |
| 9 | 5,073,170 | rs386626619 | G | T | 45 | 56 | 12600 | 30,687 | JAK2 | NM_004972:exon14:c.G1849T:p.V617F |
| 9 | 5,073,170 | rs386626619 | G | T | 47 | 73 | 12600 | 30,687 | JAK2 | NM_004972:exon14:c.G1849T:p.V617F |
| 9 | 5,073,170 | rs386626619 | G | T | 49 | 57 | 12600 | 30,687 | JAK2 | NM_004972:exon14:c.G1849T:p.V617F |
| 9 | 5,073,170 | rs386626619 | G | T | 63 | 53 | 12600 | 30,687 | JAK2 | NM_004972:exon14:c.G1849T:p.V617F |
| 9 | 5,073,170 | rs386626619 | G | T | 64 | 17 | 12600 | 30,687 | JAK2 | NM_004972:exon14:c.G1849T:p.V617F |
| 9 | 5,073,170 | rs386626619 | G | T | 66 | 23 | 12600 | 30,687 | JAK2 | NM_004972:exon14:c.G1849T:p.V617F |
| 9 | 5,073,170 | rs386626619 | G | T | 69 | 15 | 12600 | 30,687 | JAK2 | NM_004972:exon14:c.G1849T:p.V617F |
| 9 | 5,073,170 | rs386626619 | G | T | 70 | 9 | 12600 | 30,687 | JAK2 | NM_004972:exon14:c.G1849T:p.V617F |
| 9 | 5,073,170 | rs386626619 | G | T | 73 | 10 | 12600 | 30,687 | JAK2 | NM_004972:exon14:c.G1849T:p.V617F |
| 9 | 5,073,170 | rs386626619 | G | T | 79 | 9 | 12600 | 30,687 | JAK2 | NM_004972:exon14:c.G1849T:p.V617F |
| 9 | 5,073,170 | rs386626619 | G | T | 81 | 7 | 12600 | 30,687 | JAK2 | NM_004972:exon14:c.G1849T:p.V617F |
| 9 | 5,073,170 | rs386626619 | G | T | 81 | 9 | 12600 | 30,687 | JAK2 | NM_004972:exon14:c.G1849T:p.V617F |
| 9 | 5,073,170 | rs386626619 | G | T | 84 | 13 | 12600 | 30,687 | JAK2 | NM_004972:exon14:c.G1849T:p.V617F |
| 9 | 5,073,170 | rs386626619 | G | T | 87 | 19 | 12600 | 30,687 | JAK2 | NM_004972:exon14:c.G1849T:p.V617F |
| 9 | 5,073,170 | rs386626619 | G | T | 88 | 28 | 12600 | 30,687 | JAK2 | NM_004972:exon14:c.G1849T:p.V617F |
| 9 | 5,073,170 | rs386626619 | G | T | 88 | 42 | 12600 | 30,687 | JAK2 | NM_004972:exon14:c.G1849T:p.V617F |
| 11 | 108,236,087 | NA | G | A | 81 | 7 | 1139601121626 | 8 | ATM | NM_000051:exon63:c.G9023A:p.R3008H |
| 11 | 119,148,891 | rs267606706 | T | C | 30 | 8 | 34052 | 24 | CBL | NM_005188:exon8:c.T1111C:p.Y371H |
| 11 | 119,149,251 | rs267606708 | G | A | 109 | 18 | 34077 | 11 | CBL | NM_005188:exon9:c.G1259A:p.R420Q |

TABLE S3-continued

List of candidate driver somatic mutations detected in the cohort.

| Chromosome | Position (GRCh37) | dbSNP 138 ID | Reference Allele | Alternate Allele | Reference Count | Alternate Count | COSMIC ID | COSMIC Count | Gene | Annotation |
|---|---|---|---|---|---|---|---|---|---|---|
| 11 | 119,349,251 | rs267606708 | G | A | 125 | 13 | 34077 | 11 | CBL | NM_005188:exon9:c.G1259A:p.R420Q |
| 15 | 90,631,935 | NA | G | A | 81 | 11 | 41877 | 10 | IDH2 | NM_002188:exon4:c.C418T:p.R140W |
| 17 | 7,577,538 | rs11540652 | C | T | 79 | 25 | 10662 1640830 3356964 99020 99021 99602 | 71 | TP53 | NM_000546:exon7:c.G743A:p.R248Q |
| 17 | 7,577,538 | rs11540652 | C | T | 83 | 15 | 10662 1640830 3356964 99020 99021 99602 | 71 | TP53 | NM_000546:exon7:c.G743A:p.R248Q |
| 17 | 7,577,568 | NA | C | T | 63 | 29 | 11059 1649400 179811 179812 179813 3388191 | 8 | TP53 | NM_000546:exon7:c.G713A:p.C238Y |
| 17 | 7,578,190 | NA | T | C | 26 | 17 | 10758 1644277 3355993 99718 99719 99720 | 23 | TP53 | NM_000546:exon6:c.A659G:p.Y220C |
| 17 | 40,474,482 | NA | T | A | 188 | 18 | 1155243 | 45 | STAT3 | NM_003150:exon21:c.A1919T:p.Y640F |
| 17 | 58,678,121 | NA | G | GC | 11 | 5 | NA | 0 | PPM1D | NM_003620:exon1:c.346_346delinsGC |
| 17 | 58,725,309 | NA | GAC | G | 37 | 41 | NA | 0 | PPM1D | NM_003620:exon4:c.883_885G |
| 17 | 58,734,163 | NA | T | A | 68 | 31 | NA | 0 | PPM1D | NM_003620:exon5:c.T1221A:p.C407X |
| 17 | 58,740,374 | NA | TG | T | 106 | 22 | NA | 0 | PPM1D | NM_003620:exon6:c.1279_1280T |
| 17 | 58,740,467 | NA | C | T | 42 | 37 | NA | 0 | PPM1D | NM_003620:exon6:c.C1372T:p.R458X |
| 17 | 58,740,467 | NA | C | T | 73 | 55 | NA | 0 | PPM1D | NM_003620:exon6:c.C1372T:p.R458X |
| 17 | 58,740,507 | NA | CA | C | 98 | 31 | NA | 0 | PPM1D | NM_003620:exon6:c.1412_1413C |

TABLE S3-continued

List of candidate driver somatic mutations detected in the cohort.

| Chromosome | Position (GRCh37) | dbSNP 138 ID | Reference Allele | Altenate Allele | Reference Count | Alternate Count | COSMIC ID | COSMIC Count | Gene | Annotation |
|---|---|---|---|---|---|---|---|---|---|---|
| 17 | 58,740,525 | NA | AT | A | 82 | 32 | NA | 0 | PPM1D | NM_003620:exon6:c.1430_1431A |
| 17 | 58,740,532 | NA | T | TA | 40 | 66 | NA | 3 | PPM1D | NM_003620:exon6:c.1437_1437delinsTA |
| 17 | 58,740,543 | NA | C | CT | 97 | 31 | NA | 0 | PPM1D | NM_003620:exon6:c.1448_1448delinsCT |
| 17 | 58,749,560 | NA | TC | T | 79 | 18 | NA | 0 | PPM1D | NM_003620:exon6:c.1465_1466T |
| 17 | 58,740,623 | NA | C | CA | 71 | 21 | NA | 0 | PPM1D | NM_003620:exon6:c.1528_1528delinsCA |
| 17 | 58,740,668 | NA | G | T | 62 | 19 | 982224 | 0 | PPM1D | NM_003620:exon6:c.G1573T:p.E525X |
| 17 | 58,740,713 | NA | G | T | 47 | 12 | NA | 0 | PPM1D | NM_003620:exon6:c.G1618T:p.E540X |
| 17 | 58,740,809 | NA | C | T | 60 | 10 | NA | 0 | PPM1D | NM_003620:exon6:c.C1714T:p.R572X |
| 17 | 74,732,935 | NA | CGGCGGCTGTGGTGTGAGTCCGGGG | C | 30 | 6 | 1318446 146289 | 23 | SRSF2 | NM_003016:exon1:c.284_308G |
| 17 | 74,732,935 | NA | CGGCGGCTGTGGTGTGAGTCCGGGG | C | 86 | 9 | 1318446 146289 | 23 | SRSF2 | NM_003016:exon1:c.284_308G |
| 17 | 74,732,959 | NA | G | C | 41 | 22 | 211661 | 30 | SRSF2 | NM_003016:exon1:c.C284G:p.P95R |
| 17 | 74,732,959 | NA | G | C | 48 | 19 | 211661 | 30 | SRSF2 | NM_003016:exon1:c.C284G:p.P95R |
| 17 | 74,732,959 | NA | G | C | 50 | 19 | 211661 | 30 | SRSF2 | NM_003016:exon1:c.C284G:p.P95R |
| 17 | 74,732,959 | NA | G | T | 34 | 15 | 211029 211504 211505 | 84 | SRSF2 | NM_003016:exon1:c.C284A:p.P95H |
| 17 | 74,732,959 | NA | G | T | 37 | 10 | 211029 211504 211505 | 84 | SRSF2 | NM_003016:exon1:c.C284A:p.P95H |
| 20 | 31,019,423 | NA | CA | C | 35 | 30 | NA | 0 | ASXL1 | NM_015338:exon9:c.920_921C |
| 20 | 31,021,158 | NA | T | A | 52 | 14 | NA | 0 | ASXL1 | NM_015338:exon11:c.T1157A:p.L386X |
| 20 | 31,021,295 | NA | C | T | 71 | 21 | NA | 0 | ASXL1 | NM_015338:exon11:c.C1294T:p.Q432X |
| 20 | 31,021,542 | NA | CTG | C | 194 | 33 | NA | 0 | ASXL1 | NM_015338:exon11:c.1541_1543C |

TABLE S3-continued

List of candidate driver somatic mutations detected in the cohort.

| Chromosome | Position (GRCh37) | dbSNP 138 ID | Reference Allele | Alternate Allele | Reference Count | Alternate Count | COSMIC ID | COSMIC Count | Gene | Annotation |
|---|---|---|---|---|---|---|---|---|---|---|
| 20 | 31,021,565 | NA | C | T | 160 | 104 | NA | 0 | ASXL1 | NM_015338:exon11:c.C1564T:p.Q522Y |
| 20 | 31,021,622 | NA | C | CGGCT | 170 | 25 | NA | 0 | ASXL1 | NM_015338:exon11:c.1621_1621delinsCGGCT |
| 20 | 31,022,286 | NA | T | TA | 74 | 15 | 36166 | 9 | ASXL1 | NM_015338:exon12:c.1771_1771delinsTA |
| 20 | 31,022,402 | NA | TCACCACTGCCATAGAGAGGCGGC | T | 12 | 6 | 36165 41597 51200 | 61 | ASXL1 | NM_015338:exon12:c.1887_1910T |
| 20 | 31,022,402 | NA | TCACCACTGCCATAGAGAGGCGGC | T | 13 | 7 | 36165 41597 51200 | 61 | ASXL1 | NM_015338:exon12:c.1887_1910T |
| 20 | 31,022,402 | NA | TCACCACTGCCATAGAGAGGCGGC | T | 16 | 8 | 36165 41597 51200 | 61 | ASXL1 | NM_015338:exon12:c.1887_1910T |
| 20 | 31,022,402 | NA | TCACCACTGCCATAGAGAGGCGGC | T | 29 | 3 | 36165 41597 51200 | 61 | ASXL1 | NM_015338:exon12:c.1887_1910T |
| 20 | 31,022,402 | NA | TCACCACTGCCATAGAGAGGCGGC | T | 29 | 3 | 36165 41597 51200 | 61 | ASXL1 | NM_015338:exon12:c.1887_1910T |
| 20 | 31,022,402 | NA | TCACCACTGCCATAGAGAGGCGGC | T | 30 | 5 | 36165 41597 51200 | 61 | ASXL1 | NM_015338:exon12:c.1887_1910T |
| 20 | 31,022,402 | NA | TCACCACTGCCATAGAGAGGCGGC | T | 39 | 8 | 36165 41597 51200 | 61 | ASXL1 | NM_015338:exon12:c.1887_1910T |
| 20 | 31,022,414 | NA | TAG | T | 14 | 6 | NA | 0 | ASXL1 | NM_015338:exon12:c.1899_1901T |
| 20 | 31,022,485 | NA | A | AG | 7 | 4 | NA | 0 | ASXL1 | NM_015338:exon12:c.1970_1970delinsAG |
| 20 | 31,022,572 | NA | AGT | A | 35 | 9 | 146261 | 2 | ASXL1 | NM_015338:exon12:c.2057_2059A |
| 20 | 31,022,592 | rs373221034 | C | T | 30 | 5 | 51388 | 11 | ASXL1 | NM_015338:exon12:c.C2077T:p.693X |
| 20 | 31,022,592 | rs373221034 | C | T | 38 | 5 | 51388 | 11 | ASXL1 | NM_015338:exon12:c.c2077T:p.693X |
| 20 | 31,022,624 | NA | TG | T | 43 | 11 | 266052 | 0 | ASXL1 | NM_015338:exon12:c.2110T |
| 20 | 31,022,624 | NA | T | TC | 60 | 14 | 1155825 | 1 | ASXL1 | NM_015338:exon12:c.2109_2109delinsTC |

TABLE S3-continued

List of candidate driver somatic mutations detected in the cohort.

| Chromosome | Position (GRCh37) | dbSNP 138 ID | Reference Allele | Alternate Allele | Reference Count | Alternate Count | COSMIC ID | COSMIC Count | Gene | Annotation |
|---|---|---|---|---|---|---|---|---|---|---|
| 20 | 31,022,688 | NA | A | T | 24 | 8 | NA | 0 | ASXL1 | NM_015338:exon12:c.A2173T:p.R725X |
| 20 | 31,022,708 | NA | AC | A | 30 | 10 | NA | 0 | ASXL1 | NM_015338:exon12:c.2193_2194A |
| 20 | 31,022,898 | NA | TC | T | 39 | 11 | 1716903 34212 | 4 | ASXL1 | NM_015338:exon12:c.2383_2384T |
| 20 | 31,022,922 | NA | C | T | 84 | 19 | 96380 | 1 | ASXL1 | NM_015338:exon12:c.C2407T:p.Q803X |
| 20 | 31,022,981 | NA | AT | A | 96 | 71 | NA | 0 | ASXL1 | NM_015338:exon12:c.2466_2467A |
| 20 | 31,022,991 | NA | G | T | 117 | 18 | NA | 0 | ASXL1 | NM_015338:exon12:c.G2476T:p.G826X |
| 20 | 31,023,045 | NA | A | AC | 247 | 47 | 1411087 41712 | 1 | ASXL1 | NM_015338:exon12:c.2530_2530delinsAC |
| 20 | 31,023,083 | NA | C | A | 306 | 65 | NA | 0 | ASXL1 | NM_015338:exon12:c.C2568A:p.C856X |
| 20 | 31,023,209 | NA | G | A | 50 | 13 | NA | 0 | ASXL1 | NM_015338:exon12:c.G2694A:p.W898X |
| 20 | 31,023,408 | NA | C | T | 52 | 14 | 267971 | 3 | ASXL1 | NM_015338:exon12:c.C2893T:p.R965X |
| 20 | 31,023,473 | NA | C | CGT | 92 | 20 | NA | 0 | ASXL1 | NM_015338:exon12:c.2958_2958delinsCGT |
| 20 | 31,023,717 | NA | C | T | 92 | 26 | 41715 | 4 | ASXL1 | NM_015338:exon12:c.C3202T:p.R1068X |
| 20 | 31,024,273 | NA | G | GC | 40 | 38 | NA | 0 | ASXL1 | NM_015338:exon12:c.3758_3758delinsGC |
| 20 | 31,025,057 | NA | CAT | C | 60 | 49 | NA | 0 | ASXL1 | NM_015338:exon12:c.4542_4544C |
| 21 | 44,524,456 | rs371769427 | G | A | 26 | 5 | 1142948 166866 | 33 | U2AF1 | NM_006758:exon2:c.C101T:p.S34F |

TABLE S4

Cysteine mutations in the DNMT3A gene. DNMT3A mutations leading to the formation of new cysteine residues and predicted de novo disulfide bond formation.

| Mutation | Number of subjects | Disulfide bonds | Disulfide Bond Score* |
|---|---|---|---|
| G543C | 1 | 524-543 | 0.99676 |
| S714C | 3 | 541-714 | 0.99651 |
| F732C | 1 | 497-732 | 0.97115 |
| Y735C | 4 | 520-735 | 0.30687 |
| R736C | 1 | 520-736 | 0.99095 |
| R749C | 2 | 749-818 | 0.99843 |
| F751C | 1 | 524-751 | 0.99811 |
| W753C | 1 | 554-753 | 0.72528 |
| R882C | 6 | 494-882 | 0.8412 |
| L889C | 1 | 818-889 | 0.99797 |

*DiANNA: unified software for Cysteine state and Disulfide Bond partner predition Note: Catalytic ADD-Domain amino acids 472-610

TABLE S5

Counts for subjects with one putative somatic mutation and no candidate drivers (one mut.), subjects with exactly two putative somatic mutations and no candidate drivers (two muts.), subjects with clonal hematopoiesis with unknown drivers (CH-UD), subjects with clonal hematopoiesis with candidate drivers (CH-CD), and subjects with clonal hematopoiesis with candidate or unknown drivers (CH). Subjects were counted across all individuals for whom both age at sampling information and sequencing data of sufficient quality for detection of putative somatic mutations were available, with the exception of subject with CH-CD for whom only age at sampling information was required.

| Age | one mut. | two muts. | CH-UD | CH-CD | CH |
|---|---|---|---|---|---|
| 19-30 | 18/174 | 1/174 | 0/174 | 1/196 | 1/174 |
| 11-35 | 36/349 | 5/349 | 2/349 | 2/371 | 3/349 |
| 36-40 | 48/661 | 13/661 | 1/661 | 5/708 | 5/661 |
| 41-45 | 93/1081 | 15/1081 | 5/1081 | 6/1154 | 9/1081 |
| 46-50 | 120/1303 | 12/1303 | 5/1303 | 18/1378 | 22/1303 |
| 51-55 | 148/1597 | 28/1597 | 10/1597 | 76/1695 | 32/1597 |
| 56-60 | 190/1725 | 41/1725 | 19/1725 | 41/1815 | 58/1725 |
| 61-65 | 187/1608 | 40/1608 | 35/1608 | 56/1659 | 88/1608 |
| 66-70 | 141/1105 | 36/1105 | 32/1105 | 44/1140 | 76/1105 |
| 71-75 | 77/600 | 29/600 | 29/600 | 48/619 | 75/600 |
| 76-80 | 57/355 | 15/355 | 32/355 | 25/356 | 58/355 |
| 81-93 | 13/73 | 5/73 | 5/73 | 7/73 | 12/73 |

TABLE S6

Subjects with clonal hematopoiesis and a diagnosis of hematologic malignancy after DNA sampling. There were 37 subjects diagnosed with hematologic malignancies after DNA sampling. Of these, 15 had showed clonal hematopoiesis in their initial DNA sample. Diagnoses of hematologic malignancies in these subjects followed DNA sampling by an average of 17 months (range: 2-36 months). Subjects with additional sequence generated to identify the malignancy are highlighted in bold.

| Subject | | | Mutations | | Months | First diagnosis |
|---|---|---|---|---|---|---|
| Sex | Age | Died | Candidate drivers | Passengers | after | Type |
| Male | 62 | Yes | NA | 3 | 32 | Unspecified B-cell lymphoma, unspecified site |
| Male | 64 | No | NA | 3 | 7 | Multiple myeloma |
| Male | 70 | Yes | SF3B1 p.K700E | 3 | 20 | Chronic lymphocytic leukemia of B-cell type |
| Female | 63 | No | NA | 3 | 11 | Chronic lymphocytic leukemia of B-cell type |
| Male | 63 | No | NA | 10 | 9 | Chronic lymphocytic leukemia of B-cell type |
| Female | 72 | Yes | TP53 p.R248Q | 3 | 34 | Acute myeloblastic leukemia[3] |
| Male | 73 | Yes | SRSF2 p.P95H | 6 | 21 | Acute myeloblastic leukemia |
| Female | 71 | No | SRSF2 p.P95H | 1 | 9 | Chronic myelomonocytic leukemia |
| Male | 64 | No | NA | 3 | 2 | Acute leukemia of unspecified cell type[2] |
| Female | 73 | Yes | DNMT3A p.V372A | 0 | 36 | Chronic leukemia of unspecified cell type |
| Female | 61 | Yes | DNMT3A p.P904L | 1 | 11 | Other myelodysplastic syndromes |
| Male | 85 | Yes | SRSF2 p.P95H | 13 | 2 | Other myelodysplastic syndromes[1] |
| Male | 69 | No | JAK2 p.V617F | 2 | 35 | Chronic myeloproliferative disease |
| Female | 76 | No | JAK2 p.V617F | 4 | 13 | Chronic myeloproliferative disease |
| Male | 57 | No | DNMT3A p.H613D | 0 | 14 | Monoclonal gammopathy |

[1]Subject #1

[2]Subject #2 (later progressed to acute myeloblastic leukemia)

[3]Subject #3

TABLE S7

Subjects with clonal hematopoiesis and a diagnosis of hematologic malignancy before DNA sampling. There were 55 subjects with a previous diagnosis of hematologic malignancy up to 12 years before DNA sampling. Of these, 14 showed clonal hematopoiesis. Previous history of hematologic malignancy was a strong risk factor for clonal hematopoiesis (OR = 6.0; 95% CI 3.1 to 12; P < 0.001, adjusting for age and sex using a linear regression model).

| Subject | | | Mutations | | First diagnosis | |
|---|---|---|---|---|---|---|
| Sex | Age | Died | Candidate drivers | Passengers | Months before | Type |
| Female | 64 | No | NA | 6 | 95 | Hodgkin lymphoma, unspecified |
| Female | 72 | Yes | NA | 18 | 148 | Hodgkin lymphoma, unspecified |
| Female | 72 | No | DNMT3A p.R556G | 2 | 17 | Follicular lymphoma, unspecified |
| Male | 63 | No | DNMT3A p.R597W | 0 | 12 | Diffuse large B-cell lymphoma |
| Male | 76 | Yes | NA | 3 | 52 | Other non-follicular lymphoma, unspecified site |
| Male | 61 | No | DNMT3A p.E907K PPM1D frameshift | 0 | 13 | Other specified types of non-Hodgkin lymphoma |
| Female | 61 | No | DNMT3A p.G543C | 2 | 145 | Acute leukemia of unspecified cell type |
| Male | 57 | No | NA | 3 | 1 | Polycythemia vera |
| Male | 51 | No | JAK2 p.V617F | 3 | 49 | Polycythemia vera |
| Male | 70 | No | JAK2 p.V617F | 1 | 46 | Polycythemia vera |
| Male | 61 | No | JAK2 p.V617F | 1 | 25 | Polycythemia vera |
| Male | 77 | Yes | CBL p.Y371H U2AF1 p.S34F | 9 | 46 | Other myelodysplastic syndromes |
| Male | 57 | No | JAK2 p.V617F | 5 | 4 | Chronic myeloproliferative disease |
| Female | 56 | No | JAK2 P.V617F | 0 | 20 | Essential (hemorrhagic) thrombocythemia |

TABLE S8

Subjects with clonal hematopoiesis at DNA sampling who died during follow-up. Subjects with additional sequence generated to identify the malignancy are highlighted in bold.

| Subject | | Mutations | | Death | |
|---|---|---|---|---|---|
| Sex | Age | Candidate Drivers | Passengers | Months after | Cause |
| Male | 73 | NA | 3 | 7 | Malignant neoplasm of sigmoid colon |
| Male | 67 | DNMT3A p.Y908C | 0 | 65 | Malignant neoplasm of prostate |
| Male | 74 | ASXL1 p.Q803X | 1 | 30 | Malignant neoplasm of prostate |
| Male | 76 | NA | 3 | 17 | Unspecified B-cell lymphoma |
| Female | 72 | NA | 18 | 3 | Unspecified Non-Hodgkin lymphoma |
| Female | 61 | DNMT3A p.P904L | 1 | 18 | Acute myeloblastic leukaemia [AML] |
| Female | 72 | TP53 p.R248Q | 3 | 36 | Acute myeloblastic leukaemia [AML] |
| Male | 73 | SRSF2 p.P95R | 6 | 26 | Acute myeloblastic leukaemia [AML] |
| Male | 85 | SRSF2 p.P95H | 13 | 16 | Unspecified leukemia |
| Male | 77 | CBL p.Y371H U2AF1 p.S34F | 9 | 16 | Myelodysplastic syndrome, unspecified |
| Male | 78 | NA | 3 | 19 | Anemia, unspecified |
| Male | 63 | DNMT3A frameshift | 0 | 6 | Haemophagocytic syndrome, infection-associated |
| Male | 68 | NA | 4 | 14 | Diabetes mellitus type 2 with renal complications |
| Male | 76 | NA | 5 | 6 | Unspecified diabetes mellitus without complications |
| Male | 59 | ASXL1 frameshift | 0 | 6 | Unspecified diabetes mellitus without complications |
| Male | 72 | PPM1D p.E540X | 5 | 4 | Parkinson disease |
| Male | 66 | NA | 3 | 5 | Anoxic brain damage, not elsewhere classified |
| Female | 64 | JAK2 p.V617F | 4 | 45 | Acute myocardial infarction, unspecified |
| Female | 82 | NA | 5 | 37 | Acute myocardial infarction, unspecified |
| Male | 59 | DNMT3A p.E599D | 0 | 30 | Acute myocardial infarction, unspecified |
| Female | 74 | NA | 3 | 9 | Atherosclerotic heart disease |
| Female | 64 | DNMT3A p.F751C | 2 | 40 | Pulmonary heart disease, unspecified |

TABLE S8-continued

Subjects with clonal hematopoiesis at DNA sampling who died during follow-up. Subjects with additional sequence generated to identify the malignancy are highlighted in bold.

| Subject | | | Mutations | | Death | |
|---|---|---|---|---|---|---|
| Sex | Age | Candidate Drivers | Passengers | Months after | Cause | |
| Male | 73 | SF3B1 p.K666T TET2 frameshift | 8 | 12 | Acute and subacute infective endocarditis | |
| Male | 77 | NA | 5 | 10 | Endocarditis, valve unspecified | |
| Male | 77 | NA | 7 | 27 | Heart failure, unspecified | |
| Female | 80 | NA | 4 | 10 | Heart failure, unspecified | |
| Female | 65 | PPM1D p.R458X | 0 | 10 | Cardiomegaly | |
| Female | 75 | TET2 frameshift | 2 | 19 | Subarachnoid haemorrhage unspecified | |
| Female | 88 | ASXL1 p.R965X | 3 | 7 | intracerebral haemorrhage, unspecified | |
| Male | 67 | NA | 4 | 34 | Stroke, not specified as haemorrhage or infarction | |
| Female | 64 | DNMT3A p.C520X | 3 | 24 | Other specified cerebrovascular diseases | |
| Male | 81 | DNMT3A p.L344P | 0 | 42 | Sequelae of other and unspecified cerebrovascular diseases | |
| Female | 70 | DNMT3A p.R882H | 0 | 48 | Generalized and unspecified atherosclerosis | |
| Male | 54 | NA | 3 | 39 | Generalized and unspecified atherosclerosis | |
| Male | 66 | DNMT3A p.I681M | 4 | 32 | Generalized and unspecified atherosclerosis | |
| Female | 75 | DNMT3A p.Q816X | 0 | 7 | Unspecified chronic bronchitis | |
| Male | 68 | NA | 3 | 11 | Chronic obstructive pulmonary disease, unspecified | |
| Female | 62 | ASXL1 frameshift | 2 | 57 | Chronic obstructive pulmonary disease, unspecified | |
| Male | 74 | NA | 5 | 39 | Chronic obstructive pulmonary disease, unspecified | |
| Female | 65 | DNMT3A p.E733G JAK2 p.V617F | 7 | 26 | Chromc obstructive pulmonary disease, unspecificd | |
| Male | 57 | NA | 3 | 34 | Gastro-oesophageal reflux disease with oesophagitis | |
| Male | 51 | DNMT3A p.M761V | 6 | 28 | Other ill-defined and unspecified causes of mortality | |
| Female | 65 | TET2 frameshift | 3 | 15 | Other ill-defined and unspecified causes of mortality | |
| Male | 77 | NA | 4 | 26 | Unspecified drowning and submersion | |
| Female | 74 | DNMT3A p.P307R | 3 | 44 | Unknown | |
| Male | 64 | SF3B1 p.K666N | 7 | 48 | Unknown | |
| Male | 70 | NA | 3 | 52 | Unknown | |
| Male | 62 | NA | 3 | 43 | Unknown | |
| Male | 70 | SF3B1 p.K700E | 3 | 43 | Unknown | |
| Male | 74 | ASXL1 frameshift | 4 | 41 | Unknown | |
| Female | 73 | DNMT3A p.V372A | 0 | 42 | Unknown | |
| Male | 67 | JAK2 p.V617F | 4 | 44 | Unknown | |
| Male | 72 | 1DH2 p.R140W SRSF2 frameshift | 2 | 37 | Unknown | |
| Female | 75 | DNMT3A p.Y735C | 0 | 27 | Unknown | |

TABLE S9

Somatic mutations for Subject #1. List of putative somatic mutations and candidate driver somatic mutations from whole-exome sequencing (WES) data and high coverage whole-genome sequencing (WGS) data of blood. Candidate driver somatic mutations are highlighted in bold.
Subject #1 (diagnosed with myeloid malignancy 2 months after DNA sampling)

| Chromosome | Position (GRCh37) | dbSNP 138 or COSMIC ID | Refence Allele | Alternate Allele | Reference Count (WES blood) | Alternate Count (WES blood) | Reference Count (WGS blood) |
|---|---|---|---|---|---|---|---|
| 1 | 197,070,852 | NA | A | G | 82 | 23 | 115 |
| 2 | 242,178,077 | NA | T | G | 196 | 79 | 109 |
| 3 | 38,519,942 | NA | G | A | 65 | 18 | 107 |
| 3 | 46,306,703 | NA | T | A | 52 | 8 | 126 |
| 3 | 52,437,754 | rs150524807 | G | A | 52 | 8 | 124 |

TABLE S9-continued

Somatic mutations for Subject #1. List of putative somatic mutations and candidate driver somatic mutations from whole-exome sequencing (WES) data and high coverage whole-genome sequencing (WGS) data of blood. Candidate driver somatic mutations are highlighted in bold.
Subject #1 (diagnosed with myeloid malignancy 2 months after DNA sampling)

| | | | | | | | |
|---|---|---|---|---|---|---|---|
| 4 | 106,162,527 | NA | T | TTA | 0 | 0 | 111 |
| 4 | 106,164,929 | NA | A | G | 0 | 0 | 126 |
| 4 | 158,284,236 | NA | C | T | 79 | 21 | 107 |
| 5 | 54,404,054 | NA | G | A | 74 | 10 | 108 |
| 6 | 50,696,983 | COSM3354285 | C | T | 160 | 44 | 105 |
| 11 | 67,265,009 | NA | C | T | 198 | 25 | 146 |
| 13 | 23,909,533 | rs9552930 | T | C | 75 | 17 | 107 |
| 14 | 92,472,207 | NA | G | C | 154 | 30 | 118 |
| 15 | 43,668,387 | NA | A | T | 110 | 32 | 139 |
| 17 | 74,732,959 | COSM211029 | G | T | 37 | 30 | 100 |
| | | COSM211504 | | | | | |
| | | COSM211505 | | | | | |
| 20 | 1,107,965 | NA | A | G | 196 | 29 | 103 |
| 20 | 31,022,441 | COSM34210 | A | AG | 10 | 3 | 89 |
| | | COSM1411076 | | | | | |
| | | COSM1658769 | | | | | |
| 21 | 36,259,198 | COSM24719 | AG | A | 57 | 3 | 127 |
| | | COSM24728 | | | | | |
| X | 123,191,828 | NA | G | A | 28 | 2 | 33 |

| Chromosome | Alternate Count (WGS blood) | Gene | Annotation |
|---|---|---|---|
| 1 | 19 | ASPM | NM_018136:exon18:c.T7529C:p.I2510T |
| 2 | 33 | HDLBP | NM_005336:exon20:c.A2736C:p.R912S |
| 3 | 35 | ACPR2B | NM_001106:exon5:c.G599A:p.R200H |
| 3 | 21 | CCR3 | NM_001837:exon3:c.T54A:p.D18H |
| 3 | 31 | BAP1 | NM_004656:exon13:c.C1407T:p.S469S |
| 4 | 17 | TET2 | NM_001127208:exon4: |
| | | | c.3441_3441delinsTTA |
| 4 | 22 | TET2 | NM_001127208:exon6:c.A3797G: |
| | | | p.N1266S |
| 4 | 22 | GRIA2 | NA |
| 5 | 23 | GZMA | NN_006144:exon4:c.G459A:p.W153X |
| 6 | 28 | TFAF2D | NM_172233:exon5:c.C841T:p.R281W |
| 11 | 18 | PITPNM1 | NM_004910:exon13:c.G1924A:p.E642K |
| 13 | 38 | SACS | NM_014363:exon10:c.A8482G:p.S2828G |
| 14 | 16 | TRIP11 | NM_004239:exon11:c.C2113G:p.L705V |
| 15 | 31 | TUBGCP4 | NM_014444:exon2:c.A170T:p.E57V |
| 17 | 20 | SRSF2 | NM_003016:exon1:c.C284A:p.P95H |
| 20 | 20 | PSMF1 | NA |
| 20 | 31 | ASXL1 | NM_015338:exon12: |
| | | | c.1926_1926delinsAG |
| 21 | 17 | RUNX1 | NM_001754:exon4:c.292_293T |
| X | 12 | STAG2 | NM_001042750:exon15:c.1416+1G>A |

TABLE S10

Somatic mutations for Subject #2. List of putative somatic mutations and candidate driver somatic mutations from whole-exome sequencing (WES) data of blood, high coverage whole-genome sequencing (WGS) data of blood, and whole-exome sequencing data for bone marrow biopsy at the time of first diagnosis. Candidate driver somatic mutations are highlighted in bold.
Table S10 discloses SEQ ID NO: 4 in the alternate allele column and SEQ ID NO: 5 in the annotation column.
Subject #2 (diagnosed with AML 2 months after DNA sampling)

| Chromosome | Position (GRCh37) | dbSNP 138 or COSMIC ID | Reference Allele | Alternate Allele | Reference Count (WES blood) | Alternate Count (WES blood) | Reference Count (WGS blood) | Alternate Count (WGS blood) | Reference Count (WES bone marrow) | Alternate Count (WES bone marrow) | Gene | Annotation |
|---|---|---|---|---|---|---|---|---|---|---|---|---|
| 11 | 123,811,251 | NA | G | A | 91 | 20 | 150 | 11 | 36 | 14 | OR5D5 | NM_001001965: exon1: c.G928A: p.G310S |

TABLE S10-continued

Somatic mutations for Subject #2. List of putative somatic mutations and candidate driver somatic mutations from whole-exome sequencing (WES) data of blood, high coverage whole-genome sequencing (WGS) data of blood, and whole-exome sequencing data for bone marrow biopsy at the time of first diagnosis. Candidate driver somatic mutations are highlighted in bold. Table S10 discloses SEQ ID NO: 4 in the alternate allele column and SEQ ID NO: 5 in the annotation column.

Subject #2 (diagnosed with AML 2 months after DNA sampling)

| Chromosome | Position (GRCh37) | dbSNP 138 or COSMIC ID | Reference Allele | Alternate Allele | Reference Count (WES blood) | Alternate Count (WES blood) | Reference Count (WGS blood) | Alternate Count (WGS blood) | Reference Count (WES bone marrow) | Alternate Count (WES bone marrow) | Gene | Annotation |
|---|---|---|---|---|---|---|---|---|---|---|---|---|
| 19 | 10,090,052 | NA | G | A | 182 | 52 | 149 | 14 | 140 | 38 | COL5A3 | NM_05719: exon38: c.C2754T: p.V918V |
| 19 | 33,792,380 | COSM27466 | A | ACCTTCTGCTGCGTCTCCACGTTGCGCTGCTTGG | 42 | 0* | 55 | 13* | 85 | 7^ | CEBPA | NM_004364: exon1: c.941_941 delins CCAAGCAGCGCAACGTGGAGACGCAGCAGAAGGT |
| 19 | 33,793,111 | COSM18539 COSM29127 COSM29220 | CG | C | 0 | 0 | 92 | 7^ | 26 | 3* | CEBPA | NM_004364: exon1: c.210_211G |
| 20 | 43,129,883 | NA | C | T | 109 | 18 | 136 | 16 | 110 | 22 | SERINC3 | NM_006811: exon9: c.G1114A: p.V372I |

*due to the size of this insertion, alternate allele count is dependent on sequencing reads length, 76 for WES blood, 151 for WGS blood, and 101 for WES bone marrow
^this mutation was not automatically genotyped by Haplotype Caller from the Genome Analysis Toolkit due to low allelic count

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

The invention claimed is:

1. A method of detecting DNMT3A mis-sense mutations in hematopoietic stem cells (HSCs), the method comprising the steps of:
   (a) obtaining a blood sample from a human subject
   (b) isolating HSCs from the blood sample;
   (c) sequencing DNMT3A nucleic acids from one or more of the isolated HSCs;
   (d) detecting the presence of a mis-sense mutation in the sequenced DNMT3A nucleic acids, wherein the mis-sense mutation is G543C, F732C, Y735C, R749C, F751C, W753C, or L889C; and
   (e) reducing the incidence of HSCs comprising said mutations in the subject and administering to the subject HSCs in which the mutations are absent.

2. The method of claim 1, wherein the subject is at least 50 years of age.

3. The method of claim 1, wherein the subject is or has been exposed to a human carcinogen in sufficient amount and/or frequency for such carcinogen to be a potential cause of hematological malignancy.

4. The method of claim 3, wherein the carcinogen comprises a tobacco product, an organic solvent, a virus, a compound found in grilled red meat, ionizing radiation, a heavy metal or compound thereof, or any combination thereof.

5. The method of claim 1, wherein the HSCs in which the mutations are absent are administered in a bone marrow transplantation.

6. The method of claim 1, wherein the HSCs in which the mutations are absent are administered in a blood transfusion.

7. A method of determining whether a subject is predisposed to a hematological malignancy, the method comprising the steps of:
   (a) obtaining a blood sample from a human subject
   (b) isolating hematopoietic stem cells (HSCs) from the blood sample;
   (c) sequencing DNMT3A nucleic acids from one or more of the isolated HSCs;
   (d) detecting the presence of a mis-sense mutation in the sequenced DNMT3A nucleic acids, wherein the mis-sense mutation is G543C, F732C, Y735C, R749C, F751C, W753C, or L889C;
   (e) determining that the subject is predisposed to a hematological malignancy if the mis-sense mutation is detected; and
   (f) reducing the incidence of HSCs comprising said mutations in the subject and administering to the subject HSCs in which the mutations are absent.

8. The method of claim 7, wherein the hematological malignancy is a myeloproliferative neoplasm, a myelodysplastic syndrome, acute myeloid leukemia or chronic lymphocytic leukemia.

9. The method of claim 7, wherein the human subject is at least 50 years of age.

10. The method of claim 7, wherein the human subject has been exposed to a human carcinogen in sufficient amount and/or frequency for such carcinogen to be a potential cause of hematological malignancy.

11. The method of claim 10, wherein the carcinogen comprises a tobacco product, an organic solvent, a virus, a compound found in grilled red meat, ionizing radiation, a heavy metal or compound thereof, or any combination thereof.

12. The method of claim 7, wherein the HSCs in which the mutations are absent are administered in a bone marrow transplantation.

13. The method of claim 7, wherein the HSCs in which the mutations are absent are administered in a blood transfusion.

14. A method of selecting hematopoietic cells for transplantation, the method comprising the steps of:
   (a) obtaining a sample comprising hematopoietic cells from a human subject;
   (b) sequencing DNMT3A nucleic acids from one or more of the hematopoietic cells;
   (c) detecting the absence of G543C, F732C, Y735C, R749C, F751C, W753C, and L889C mis-sense mutations in the sequenced DNMT3A nucleic acids; and
   (d) collecting the remaining hematopoietic cells in the sample for transplantation.

15. The method of claim 14, wherein the hematopoietic cells are collected for autologous transplantation.

16. The method of claim 14, wherein the hematopoietic cells are collected for allogenic transplantation.

17. The method of claim 14, wherein the sample is obtained from the human subject prior to diagnosis of a hematological malignancy.

18. The method of 14, wherein the sample is derived from cord blood.

\* \* \* \* \*